US011821111B2

(12) United States Patent
Bloom et al.

(10) Patent No.: US 11,821,111 B2
(45) Date of Patent: Nov. 21, 2023

(54) BARCODED INFLUENZA VIRUSES AND DEEP MUTATIONAL SCANNING LIBRARIES INCLUDING THE SAME

(71) Applicants: FRED HUTCHINSON CANCER CENTER, Seattle, WA (US); University of Washington, Seattle, WA (US)

(72) Inventors: Jesse Bloom, Seattle, WA (US); Allison Greaney, Seattle, WA (US); Andrea Loes, Seattle, WA (US); Adam S. Dingens, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 298 days.

(21) Appl. No.: 17/097,853

(22) Filed: Nov. 13, 2020

(65) Prior Publication Data

US 2021/0147832 A1 May 20, 2021

Related U.S. Application Data

(60) Provisional application No. 62/935,954, filed on Nov. 15, 2019.

(51) Int. Cl.
*C40B 50/06* (2006.01)
*C12N 15/10* (2006.01)
*C12N 7/00* (2006.01)
(52) U.S. Cl.
CPC ............... *C40B 50/06* (2013.01); *C12N 7/00* (2013.01); *C12N 15/1065* (2013.01); *C12N 2760/16021* (2013.01)

(58) Field of Classification Search
None
See application file for complete search history.

(56) References Cited

U.S. PATENT DOCUMENTS 5,994,515 A 11/1999 Hoxie
8,383,345 B2 2/2013 Shendure et al.
(Continued)

FOREIGN PATENT DOCUMENTS

WO WO2008147427 A2 12/2008
WO WO2009027057 A1 3/2009
(Continued)

OTHER PUBLICATIONS

Lee et al. (Aug. 13, 2018) PNAS USA vol. 115 pp. E8276 to E8285 supplementary information pp. 1 to 15.*
(Continued)

*Primary Examiner* — Christian C Boesen
(74) *Attorney, Agent, or Firm* — C. Rachal Winger; Chrystal Quisenberry; Lee & Hayes PC

(57) ABSTRACT

Methods to create barcoded influenza viruses without disrupting the function of the viral proteins and the proper packaging of the viral genome segments are described. The barcoded influenza viruses can be used within deep mutational scanning libraries to map influenza resistance mutations to therapeutic treatments. The libraries can also be used to predict influenza strains that may become resistant to therapeutic treatments and/or more easily evolve to infect new species. The libraries include features that allow efficient collection and assessment of informative data, obviating bottlenecks of previous approaches.

7 Claims, 28 Drawing Sheets
Specification includes a Sequence Listing.

(56) References Cited

U.S. PATENT DOCUMENTS

| | | | |
|---|---|---|---|
| 9,259,433 | B2 | 2/2016 | Huang et al. |
| 2009/0214510 | A1 | 8/2009 | Nabel et al. |
| 2016/0145603 | A1 | 5/2016 | Bloom |
| 2017/0157190 | A1 | 6/2017 | Lamb et al. |

FOREIGN PATENT DOCUMENTS

| | | |
|---|---|---|
| WO | WO2009151313 A1 | 12/2009 |
| WO | WO2012006596 A2 | 1/2013 |
| WO | WO2013006795 A2 | 1/2013 |
| WO | WO2013072917 A2 | 5/2013 |
| WO | WO2014062892 A1 | 4/2014 |

OTHER PUBLICATIONS

Dos et al. (2005) Virology vol. 341 pp. 34 to 46.*
Bedform, et al., "Global circulation patterns of seasonal influenza viruses vary with antigenic drift," Nature, vol. 523, No. 7559, 2015, pp. 217-220.
Bloom, "An experimentally determined evolutionary model dramatically improves phylogenetic fit," Molecular Biology and Evolution, vol. 31, No. 8, 2014, pp. 1956-1978.
Bloom, "Software for the analysis and visualization of deep mutational scanning data," BMC Bioinformatics, vol. 16, No. 168, 2015, 13 pages.
Chin, et al., "Nonhybrid, finished microbial genome assemblies from long-read SMRT sequencing data," Nature Methods, vol. 10, No. 6, 2013, pp. 563-569.
Cox & Subbarao, "Global epidemiology of influenza: past and present," Annual Review of Medicine, vol. 51, 2000, pp. 407-421.
DePristo, et al., "A framework for variation discovery and genotyping using next-generation DNA sequencing data," Nature Genetics, vol. 43, No. 5, 2011, pp. 491-498.
Dingens, et al., "Comprehensive Mapping of HIV-1 Escape from a Broadly Neutralizing Antibody," Cell Host & Microbe, vol. 21, No. 6, 2017, pp. 777-787.
Diskin, et al., "Restricting HIV-1 pathways for escape using rationally designed anti-HIV-1 antibodies," Journal of Experimental Medicine, vol. 210, No. 6, 2013, pp. 1235-1249.
Doud & Bloom, "Accurate Measurement of the Effects of All Amino-Acid Mutations on Influenza Hemagglutinin," Viruses, vol. 8, No. 6, 2016, 17 pages.
Doud, et al., "Complete mapping of viral escape from neutralizing antibodies," PLOS Pathogens, vol. 13, No. 3, 2017, 20 pages.
Doud, et al., "Quantifying the ease of viral escape from broad and narrow antibodies to influenza hemagglutinin," bioRXiv, 2018, 39 pages.
Findlay, et al., "Saturation editing of genomic regions by multiplex homology-directed repair," Nature, vol. 513, No. 7516, 2014, pp. 120-123.
Firnberg & Ostermeier, "PFunkel: efficient, expansive, user-defined mutagenesis," PLoS One, vol. 7, No. 12, 2012, 10 pages.
Fowler & Fields, "Deep mutational scanning: a new style of protein science," Nature Methods, vol. 11, No. 8, 2014, pp. 801-807.
Fowler, et al., "Measuring the activity of protein variants on a large scale using deep mutational scanning," Nature Protocols, vol. 9, No. 9, 2014, pp. 2267-2284.
Gao & Palese, "Rewiring the RNAs of influenza virus to prevent reassortment," PNAS USA, vol. 106, No. 37, 2009, pp. 15891-15896.
Gao, et al., "The Influenza A Virus PB2, PA, NP, and M Segments Play a Pivotal Role during Genome Packaging," Journal of Virology, vol. 86, No. 13, 2012, pp. 7043-7051.
Gerber, et al., "Selective packaging of the influenza A genome and consequences for genetic reassortment," Trends in Microbiology, vol. 22, No. 8, 2014, pp. 446-455.
Gong, et al., "Stability-mediated epistasis constrains the evolution of an influenza protein," eLife, vol. 2, 2013, 19 pages.
Haddox, et al., "Experimental Estimation of the Effects of All Amino-Acid Mutations to HIV's Envelope Protein on Viral Replication in Cell Culture," PloS Pathogens, vol. 12, No. 12, 2016, 32 pages.
Haddox, et al., "Mapping mutational effects along the evolutionary landscape of HIV envelope," eLife, vol. 7, 2018, 29 pages.
Harding, et al., "Rationally Designed Influenza Virus Vaccines That Are Antigenically Stable during Growth in Eggs," mBio, vol. 8, No. 3, 2017, 16 pages.
Hay, et al., "The evolution of human influenza viruses," Phil. Trans. R. Soc. Lond. B, vol. 356, 2001, pp. 1861-1870.
Heaton, et al., "Genome-wide mutagenesis of influenza virus reveals unique plasticity of the hemagglutinin and NS1 proteins," PNAS USA, vol. 110, No. 50, 2013, pp. 20248-20253.
Hiatt, et al., "Parallel, tag-directed assembly of locally derived short sequence reads," Nature Methods, vol. 7, No. 2, 2010, pp. 119-122.
Hilton, et al., "phydms: software for phylogenetic analyses informed by deep mutational scanning," PeerJ, 2013, 20 pages.
Hoffmann, et al., "A Dna transfection system for generation of influenza A virus from eight plasmids," PNAS USA, vol. 97, No. 11, 2000, pp. 6108-6113.
Hopf, et al., "Mutation effects predicted from sequence co-variation," Nature Biotechnology, vol. 35, No. 2, 2017, pp. 128-135.
Hutchinson, et al., "Genome packaging in influenza A virus Open Access," Journal of General Virology, vol. 91, No. 2, 2010, pp. 313-328.
Jagger, et al., "An overlapping protein-coding region in influenza A virus segment 3 modulates the host response," Science, vol. 337, No. 6091, 2012, pp. 199-204.
Jain & Varadarajan, "A rapid, efficient, and economical inverse polymerase chain reaction-based method for generating a site saturation mutant library," Analytical Biochemistry, vol. 449, 2014, pp. 90-98.
Julien, et al., "Broadly neutralizing antibody PGT121 allosterically modulates CD4 binding via recognition of the HIV-1 gp120 V3 base and multiple surrounding glycans," PLoS Pathogens, vol. 9, No. 5, 2013, 15 pages.
Kitzman, et al., "Massively parallel single-amino-acid mutagenesis," Nature Methods, vol. 12, No. 3, 2015, pp. 203-206.
Koszalka, et al., "Influenza antivirals currently in late-phase clinical trial," Influenza and Other Respiratory Viruses, vol. 11, No. 3, 2017, pp. 240-246.
Krammer, "The human antibody response to influenza A virus infection and vaccination," Nat. Rev. Immunol., vol. 19, No. 6, 2019, pp. 383-397.
Larsen, et al., "The utility of PacBio circular consensus sequencing for characterizing complex gene families in non-model organisms," BMC Genomics, vol. 15, No. 720, 2014, 15 pages.
Laursen & Wilson, "Broadly neutralizing antibodies against influenza viruses," Antiviral Research, vol. 98, No. 3, 2013, pp. 476-483.
Lee, et al., "Deep mutational scanning of hemagglutinin helps predict evolutionary fates of human H3N2 influenza variants," PNAS USA, vol. 115, No. 35, 2018, pp. E8276-E8285.
Lee, et al., "Mapping person-to-person variation in viral mutations that escape polyclonal serum targeting influenza hemagglutinin," eLife, 2019, 28 pages.
Louie, et al., "Fitness landscape of the human immunodeficiency virus envelope protein that is targeted by antibodies," PNAS USA, vol. 115, No. 4, 2018, pp. E564-E573.
Luksza & Lassig, "A predictive fitness model for influenza," Nature, vol. 507, No. 7490, 2014, pp. 57-61.
Martinez-Sobrido & Garcia-Sastre, "Generation of Recombinant Influenza Virus from Plasmid DNA," Journal of Visualized Experiments, vol. 24, 2010, 5 pages.
Moncla, et al., "Influenza Evolution: New Insights into an Old Foe," Trends in Microbiology, vol. 25, No. 6, 2017, pp. 432-434.
Muramoto, et al., "Identification of Novel Influenza A Virus Proteins Translated from PA mRNA," Journal of Virology, vol. 87, No. 5, 2013, pp. 2455-2462.
Nakatsu, et al., "Influenza C and D Viruses Package Eight Organized Ribonucleoprotein Complexes," Journal of Virology, vol. 92, No. 6, 2018, 9 pages.

(56) References Cited

OTHER PUBLICATIONS

Nucleotide [Internet]. Bethesda (MD): National Library of Medicine (US), National Center for Biotechnology Information; [1988]—. Accession No. NC_002016.1, Influenza A virus (A/Puerto Rico/8/1934(H1N1)) segment 7, complete sequence; [cited Feb. 4, 2021]. Available from: https://www.ncbi.nlm.nih.gov/nuccore/NC_002016.1.

Nucleotide [Internet]. Bethesda (MD): National Library of Medicine (US), National Center for Biotechnology Information; [1988]—. Accession No. NC_002017.1, Influenza A virus (A/Puerto Rico/8/1934(H1N1)) segment 4, complete sequence; [cited Feb. 4, 2021]. Available from: https://www.ncbi.nlm.nih.gov/nuccore/NC_002017.1.

Nucleotide [Internet]. Bethesda (MD): National Library of Medicine (US), National Center for Biotechnology Information; [1988]—. Accession No. NC_002018.1, Influenza A virus (A/Puerto Rico/8/1934(H1N1)) segment 6, complete sequence, [cited Feb. 4, 2021]. Available from: https://www.ncbi.nlm.nih.gov/nuccore/NC_002018.1.

Nucleotide [Internet]. Bethesda (MD): National Library of Medicine (US), National Center for Biotechnology Information; [1988]—. Accession No. NC_002019.1, Influenza A virus (A/Puerto Rico/8/1934(H1N1)) segment 5, complete sequence; [cited Feb. 4, 2021]. Available from: https://www.ncbi.nlm.nih.gov/nuccore/NC_002019.1.

Nucleotide [Internet]. Bethesda (MD): National Library of Medicine (US), National Center for Biotechnology Information; [1988]—. Accession No. NC_002020.1, Influenza A virus (A/Puerto Rico/8/1934(H1N1)) segment 8, complete sequence; [cited Feb. 4, 2021]. Available from: https://www.ncbi.nlm.nih.gov/nuccore/NC_002020.1.

Nucleotide [Internet]. Bethesda (MD): National Library of Medicine (US), National Center for Biotechnology Information; [1988]—. Accession No. NC_002021.1, Influenza A virus (A/Puerto Rico/8/1934(H1N1)) segment 2, complete sequence; [cited Feb. 4, 2021]. Available from: https://www.ncbi.nlm.nih.gov/nuccore/NC_002021.1.

Nucleotide [Internet]. Bethesda (MD): National Library of Medicine (US), National Center for Biotechnology Information; [1988]—. Accession No. NC_002022.1, Influenza A virus (A/Puerto Rico/8/1934(H1N1)) segment 3, complete sequence; [cited Feb. 4, 2021]. Available from: https://www.ncbi.nlm.nih.gov/nuccore/NC_002022.1.

Nucleotide [Internet]. Bethesda (MD): National Library of Medicine (US), National Center for Biotechnology Information; [1988]—. Accession No. NC_002023.1, Influenza A virus (A/Puerto Rico/8/1934(H1N1)) segment 1, complete sequence, [cited Feb. 4, 2021]. Available from: https://www.ncbi.nlm.nih.gov/nuccore/NC_002023.1.

Nucleotide [Internet]. Bethesda (MD): National Library of Medicine (US), National Center for Biotechnology Information; [1988]—. Accession No. NC_002204.1, Influenza B virus RNA 1, complete sequence; [cited Feb. 4, 2021]. Available from: https://www.ncbi.nlm.nih.gov/nuccore/NC_002204.1.

Nucleotide [Internet]. Bethesda (MD): National Library of Medicine (US), National Center for Biotechnology Information; [1988]—. Accession No. NC_002205.1, Influenza B virus (B/Lee/1940) segment 2, complete sequence; [cited Feb. 4, 2021]. Available from: https://www.ncbi.nlm.nih.gov/nuccore/NC_002205.1.

Nucleotide [Internet]. Bethesda (MD): National Library of Medicine (US), National Center for Biotechnology Information; [1988]—. Accession No. NC_002206.1, Influenza B virus (B/Lee/1940) segment 3, complete sequence; [cited Feb. 4, 2021]. Available from: https://www.ncbi.nlm.nih.gov/nuccore/NC_002206.1.

Nucleotide [Internet]. Bethesda (MD): National Library of Medicine (US), National Center for Biotechnology Information; [1988]—. Accession No. NC_002207.1, Influenza B virus (B/Lee/1940) segment 4, complete sequence; [cited Feb. 4, 2021]. Available from: https://www.ncbi.nlm.nih.gov/nuccore/NC_002207.1.

Nucleotide [Internet]. Bethesda (MD): National Library of Medicine (US), National Center for Biotechnology Information; [1988]—. Accession No. NC_002208.1, Influenza B virus (B/Lee/1940) segment 5, complete sequence; [cited Feb. 4, 2021]. Available from: https://www.ncbi.nlm.nih.gov/nuccore/NC_002208.1.

Nucleotide [Internet]. Bethesda (MD): National Library of Medicine (US), National Center for Biotechnology Information; [1988]—. Accession No. NC_002209.1, Influenza B virus (B/Lee/1940) segment 6, complete sequence; [cited Feb. 4, 2021]. Available from: https://www.ncbi.nlm.nih.gov/nuccore/NC_002209.1.

Nucleotide [Internet]. Bethesda (MD): National Library of Medicine (US), National Center for Biotechnology Information; [1988]—. Accession No. NC_002210.1, Influenza B virus (B/Lee/1940) segment 7, complete sequence; [cited Feb. 4, 2021]. Available from: https://www.ncbi.nlm.nih.gov/nuccore/NC_002210.1.

Nucleotide [Internet]. Bethesda (MD): National Library of Medicine (US), National Center for Biotechnology Information; [1988]—. Accession No. NC_002211.1, Influenza B virus (B/Lee/1940) segment 8, complete sequence; [cited Feb. 4, 2021]. Available from: https://www.ncbi.nlm.nih.gov/nuccore/NC_002211.1.

Nucleotide [Internet]. Bethesda (MD): National Library of Medicine (US), National Center for Biotechnology Information; [1988]—. Accession No. NC_007357.1, Influenza A virus (A/Goose/Guangdong/1/96(H5N1)) polymerase (PB2) gene, complete cds; [cited Feb. 4, 2021]. Available from: https://www.ncbi.nlm.nih.gov/nuccore/NC_007357.1.

Nucleotide [Internet]. Bethesda (MD): National Library of Medicine (US), National Center for Biotechnology Information; [1988]—. Accession No. NC_007358.1, Influenza A virus (A/goose/Guangdong/1/1996(H5N1)) polymerase (PB1) and PB1-F2 protein (PB1-F2) genes, complete cds; [cited Feb. 4, 2021]. Available from: https://www.ncbi.nlm.nih.gov/nuccore/NC_007358.1.

Nucleotide [Internet]. Bethesda (MD): National Library of Medicine (US), National Center for Biotechnology Information; [1988]—. Accession No. NC_007359.1, Influenza A virus (A/goose/Guangdong/1/1996(H5N1)) polymerase (PA) and PA-X protein (PA-X) genes, complete cds; [cited Feb. 4, 2021]. Available from: https://www.ncbi.nlm.nih.gov/nuccore/NC_007359.1.

Nucleotide [Internet]. Bethesda (MD): National Library of Medicine (US), National Center for Biotechnology Information; [1988]—. Accession No. NC_007360.1, Influenza A virus (A/Goose/Guangdong/1/96(H5N1)) nucleocapsid protein (NP) gene, complete cds; [cited Feb. 4, 2021]. Available from: https://www.ncbi.nlm.nih.gov/nuccore/NC_007360.1.

Nucleotide [Internet]. Bethesda (MD): National Library of Medicine (US), National Center for Biotechnology Information; [1988]—. Accession No. NC_007361.1, Influenza A virus (A/goose/Guangdong/1/96(H5N1)) neuraminidase (NA) gene, complete cds; [cited Feb. 4, 2021]. Available from: https://www.ncbi.nlm.nih.gov/nuccore/NC_007361.1.

Nucleotide [Internet]. Bethesda (MD): National Library of Medicine (US), National Center for Biotechnology Information; [1988]—. Accession No. NC_007362.1, Influenza A virus (A/goose/Guangdong/1/1996(H5N1)) hemagglutinin (HA) gene, complete cds; [cited Feb. 4, 2021]. Available from: https://www.ncbi.nlm.nih.gov/nuccore/NC_007362.1.

Nucleotide [Internet]. Bethesda (MD): National Library of Medicine (US), National Center for Biotechnology Information; [1988]—. Accession No. NC_007363.1, Influenza A virus (A/goose/Guangdong/1/1996(H5N1)) segment 7, complete sequence; [cited Feb. 4, 2021]. Available from: https://www.ncbi.nlm.nih.gov/nuccore/NC_007363.1.

Nucleotide [Internet]. Bethesda (MD): National Library of Medicine (US), National Center for Biotechnology Information; [1988]—. Accession No. NC_007364.1, Influenza A virus (A/goose/Guangdong/1/1996(H5N1)) segment 8, complete sequence; [cited Feb. 4, 2021]. Available from: https://www.ncbi.nlm.nih.gov/nuccore/NC_007364.1.

Nucleotide [Internet]. Bethesda (MD): National Library of Medicine (US), National Center for Biotechnology Information; [1988]—. Accession No. NC_007366.1, Influenza A virus (A/New York/392/

(56) References Cited

OTHER PUBLICATIONS

2004(H3N2)) segment 4, complete sequence; [cited Feb. 4, 2021]. Available from: https://www.ncbi.nlm.nih.gov/nuccore/NC_007366. 1.

Nucleotide [Internet]. Bethesda (MD): National Library of Medicine (US), National Center for Biotechnology Information; [1988]—. Accession No. NC_007367.1, Influenza A virus (A/New York/392/ 2004(H3N2)) segment 7, complete sequence; [cited Feb. 4, 2021]. Available from: https://www.ncbi.nlm.nih.gov/nuccore/NC_007367. 1.

Nucleotide [Internet]. Bethesda (MD): National Library of Medicine (US), National Center for Biotechnology Information; [1988]—. Accession No. NC_NC_007368.1, Influenza A virus (A/New York/ 392/2004(H3N2)) segment 6, complete sequence; [cited Feb. 4, 2021]. Available from: https://www.ncbi.nlm.nih.gov/nuccore/NC_ 007368.1.

Nucleotide [Internet]. Bethesda (MD): National Library of Medicine (US), National Center for Biotechnology Information; [1988]—. Accession No. NC_007369.1, Influenza A virus (A/New York/392/ 2004(H3N2)) segment 5, complete sequence; [cited Feb. 4, 2021]. Available from: https://www.ncbi.nlm.nih.gov/nuccore/NC_007369. 1.

Nucleotide [Internet]. Bethesda (MD): National Library of Medicine (US), National Center for Biotechnology Information; [1988]—. Accession No. NC_007370.1, Influenza A virus (A/New York/392/ 2004(H3N2)) segment 8, complete sequence; [cited Feb. 4, 2021]. Available from: https://www.ncbi.nlm.nih.gov/nuccore/NC_007370. 1.

Nucleotide [Internet]. Bethesda (MD): National Library of Medicine (US), National Center for Biotechnology Information; [1988]—. Accession No. NC_007371.1, Influenza A virus (A/New York/392/ 2004(H3N2)) segment 3, complete sequence; [cited Feb. 4, 2021]. Available from: https://www.ncbi.nlm.nih.gov/nuccore/NC_007371. 1.

Nucleotide [Internet]. Bethesda (MD): National Library of Medicine (US), National Center for Biotechnology Information; [1988]—. Accession No. NC_007372.1, Influenza A virus (A/New York/392/ 2004(H3N2)) segment 2, complete sequence; [cited Feb. 4, 2021]. Available from: https://www.ncbi.nlm.nih.gov/nuccore/NC_007372. 1.

Nucleotide [Internet]. Bethesda (MD): National Library of Medicine (US), National Center for Biotechnology Information; [1988]—. Accession No. NC_007373.1, Influenza A virus (A/New York/392/ 2004(H3N2)) segment 1, complete sequence; [cited Feb. 4, 2021]. Available from: https://www.ncbi.nlm.nih.gov/nuccore/NC_007373. 1.

Nobusawa, et al., "Comparison of complete amino acid sequences and receptor-binding properties among 13 serotypes of hemagglutinins of influenza A viruses," Virology, vol. 182, No. 2, 1991, pp. 475-485.

Norrander, et al., "Construction of improved M13 vectors using oligodeoxynucleotide-directed mutagenesis," Gene, vol. 26, No. 1, 1983, pp. 101-106.

Ozawa, et al., "Contributions of Two Nuclear Localization Signals of Influenza A Virus Nucleoprotein to Viral Replication," Journal of Virology, vol. 81, No. 1, 2007, pp. 30-41.

Pelegrin, et al., "Antiviral Monoclonal Antibodies: Can They Be More Than Simple Neutralizing Agents?," Trends in Microbiology, vol. 23, No. 10, 2015, pp. 653-665.

Poelwijk, et al., "Learning the pattern of epistasis linking genotype and phenotype in a protein," Nature Communications, vol. 10, No. 1, 2019, 11 pages.

Pond & Muse, "HyPhy: Chapter 6: Hypothesis Testing Using Phylogenies," New York, NY, United States of America, 2005, 57 pages.

Roberts, et al., "The advantages of SMRT sequencing," Genome Biology, vol. 14, No. 405, 2013, 4 pages.

Russell, et al., "Science Forum: Improving pandemic influenza risk assessment," eLife, 2013, 12 pages.

Sailer & Harms, "Detecting High-Order Epistasis in Nonlinear Genotype-Phenotype Maps," Genetics, vol. 205, No. 3, 2017, pp. 1079-1088.

Sailer & Harms, "High-order epistasis shapes evolutionary trajectories," PLoS Computational Biology, vol. 13, No. 5, 2017, 16 pages.

Scheid, et al., "HIV-1 antibody 3BNC117 suppresses viral rebound in humans during treatment interruption," Nature, vol. 535, No. 7613, 2016, pp. 556-560.

Schutze, et al., "A streamlined protocol for emulsion polymerase chain reaction and subsequent purification," Analytical Biochemistry, vol. 410, No. 1, 2011, pp. 155-157.

Shao, et al., "Evolution of Influenza A Virus by Mutation and Re-Assortment," International Journal of Molecular Sciences, vol. 18, No. 8, 2017, 13 pages.

Smith, et al., "Rapid Sequencing of Complete env Genes from Primary HIV-1 Samples," Virus Evolution, vol. 2, No. 2, 2016, 8 pages.

Starita, et al., "A Multiplex Homology-Directed DNA Repair Assay Reveals the Impact of More Than 1,000 BRCA1 Missense Substitution Variants on Protein Function," American Journal of Human Genetics, vol. 103, No. 4, 2018, pp. 498-508.

Starita, et al., "Massively Parallel Functional Analysis of BRCA1 Ring Domain Variants," Genetics, vol. 200, No. 2, 2015, pp. 413-422.

Travers, et al., A flexible and efficient template format for circular consensus sequencing and SNP detection, Nucleic Acids Research, vol. 38, No. 15, 2010, 8 pages.

Varble, et al., "Influenza A Virus Transmission Bottlenecks Are Defined by Infection Route and Recipient Host," Cell Host & Microbe, vol. 16, No. 5, 2014, pp. 691-700.

Whitehead, et al., "Nicking Mutagenesis: comprehensive single-site saturation mutagenesis," Protocol Exchange, 2016, 9 pages.

Wrenbeck, et al., "Plasmid-based one-pot saturation mutagenesis," Nature Methods, vol. 13, No. 11, 2016, pp. 928-930.

Wu, et al., "High-Throughput Identification of Loss-of-Function Mutations for Anti-Interferon Activity in the Influenza A Virus NS Segment," Journal of Virology, vol. 88, No. 17, 2014, pp. 10157-10164.

Wu, et al., High-throughput profiling of influenza A virus hemagglutinin gene at single-nucleotide resolution, Scientific Reports, vol. 4, 2014, 8 pages.

* cited by examiner

FIG. 2A

3' packaging signal — influenza ORF — 5' packaging signal

STOP codon position in transcribed mRNA

Copy of 5' packaging signal to insert influenza ORF-Δpackaging ← Barcode

STOP codon position in transcribed mRNA

3' packaging signal — influenza ORF-Δpackaging — Inserted copy of 5' packaging signal Barcode

(prior art)

Let $f_{r,x}^{start}$ be the true frequency of character $x$ at site $r$ in the starting library, and let $f_{r,x}^{s1}$ and $f_{r,x}^{s2}$ be the frequencies after selections $s1$ and $s2$, respectively. The differential preference $\Delta\pi_{r,x}$ for $x$ at $r$ in by $s2$ versus $s1$ is defined by:

$$f_{r,x}^{s1} = \left(\pi_{r,x}^{s1} \times f_{r,x}^{start}\right) \div \left(\pi_{r,y}^{s1} \times \sum_y f_{r,y}^{start}\right)$$

$$f_{r,x}^{s2} = \left[\left(\pi_{r,x}^{s1} + \Delta\pi_{r,x}\right) \times f_{r,x}^{start}\right] \div \left[\left(\pi_{r,y}^{s1} + \Delta\pi_{r,y}\right) \times \sum_y f_{r,y}^{start}\right]$$

where $\pi_{r,x}^{s1}$ is the "control preference" and is treated as a nuisance parameter, and constraints include $$\sum_x \Delta\pi_{r,x} = 0$$

$$1 \geq \Delta\pi_{r,x} + \pi_{r,x}^{s1} \geq 0$$

If there is no difference in the effect of $x$ at $r$ between selections $s1$ and $s2$, then $\Delta\pi_{r,x} = 0$. If $x$ at $r$ is more preferred by $s2$ than $s1$, then $\Delta\pi_{r,x} > 0$; conversely if $x$ at $r$ is more preferred by $s1$ than $s2$, then $\Delta\pi_{r,x} < 0$.

FIG. 9

Packaging Signal at 5' end for Influenza A virus Segment 4
AGCAAAAGCAGGGGAAAATAAAAACAACCAAATTGAAGGCAAACCTACTGGTCCTGTTAAG
TGCACTTGCAGCTGCAGTTGCAGACACAATTTGTATAG (SEQ ID NO: 1)

Packaging Signal at 3' end for Influenza A virus Segment 4
ATCTACTCAACTGTCGCCAGTTCACTGGTGCTTTTGGTCTCCCTGGGGGCAATCAGTTTCT
GGATGTGTTCTAATGGATCTTTGCAGTGCAGAATATGCATCTGAGATTAGAATTTCAGAAAT
ATGAGGAAAACACCCTTGTTTCTACT (SEQ ID NO: 2)

Packaging Signal at 5' end for Influenza A virus Segment 6
AGCGAAAGCAGGGGTTTAAATTGAATCCAAATCAGAAAATAACAACCATTGGATCAATCTGT
CTGGTAGTCGGACTAATTAGCCTAATATTGCAAATAGGGAATATAATCTCAATTTGGATTAG
CCATTCAATTCAAACTGGAAGTCAAAACCATACTGGAATTTGCAACCAA (SEQ ID NO: 3)

Packaging Signal at 3' end for Influenza A virus Segment 6
TGAGCTAACAGGGCTAGACTGTATGAGGCCGTGCTTCTGGGTTGAATTAATCAGGGGACG
ACCTAAAGAAAAACAATCTGGACTAGTGCGAGCAGCATTTCTTTTTGTGGCGTGAATAGT
GATACTGTAGATTGGTCTTGGCCAGACGGTGCTGAGTTGCCATTCAGCATTGACAAGTAGT
CTGTTCAAAAAACTCCTTGTTTCTACT (SEQ ID NO: 4)

Influenza A virus (A/Puerto Rico/8/1934(H1N1)) segment 4 (NCBI Ref Seq: NC_002017.1)
AGCAAAAGCAGGGGAAAATAAAAACAACCAAAATGAAGGCAAACCTACTGGTCCTGTTATG
TGCACTTGCAGCTGCAGATGCAGACACAATATGTATAGGCTACCATGCGAACAATTCAACC
GACACTGTTGACACAGTGCTCGAGAAGAATGTGACAGTGACACACTCTGTTAACCTGCTCG
AAGACAGCCACAACGGAAAACTATGTAGATTAAAAGGAATAGCCCCACTACAATTGGGGAA
ATGTAACATCGCCGGATGGCTCTTGGGAAACCCAGAATGCGACCCACTGCTTCCAGTGAG
ATCATGGTCCTACATTGTAGAAACACCAAACTCTGAGAATGGAATATGTTATCCAGGAGATT
TCATCGACTATGAGGAGCTGAGGGAGCAATTGAGCTCAGTGTCATCATTCGAAAGATTCGA
AATATTTCCCAAAGAAAGCTCATGGCCCAACCACAACACAACCAAAGGAGTAACGGCAGCA
TGCTCCCATGCGGGGAAAAGCAGTTTTTACAGAAATTTGCTATGGCTGACGGAGAAGGAG
GGCTCATACCCAAAGCTGAAAAATTCTTATGTGAACAAGAAAGGGAAAGAAGTCCTTGTAC
TGTGGGGTATTCATCACCCGTCTAACAGTAAGGATCAACAGAATATCTATCAGAATGAAAAT
GCTTATGTCTCTGTAGTGACTTCAAATTATAACAGGAGATTTACCCCGGAAATAGCAGAAAG
ACCCAAAGTAAGAGATCAAGCTGGGAGGATGAACTATTACTGGACCTTGCTAAAACCCGGA
GACACAATAATATTTGAGGCAAATGGAAATCTAATAGCACCAAGGTATGCTTTCGCACTGA
GTAGAGGCTTTGGGTCCGGCATCATCACCTCAAACGCATCAATGCATGAGTGTAACACGAA
GTGTCAAACACCCCTGGGAGCTATAAACAGCAGTCTCCCTTTCCAGAATATACACCCAGTC
ACAATAGGAGAGTGCCCAAAATACGTCAGGAGTGCCAAATTGAGGATGGTTACAGGACTAA
GGAACATTCCGTCCATTCAATCCAGAGGTCTATTTGGAGCCATTGCCGGTTTTATTGAAGG
GGGATGGACTGGAATGATAGATGGATGGTACGGTTATCATCATCAGAATGAACAGGGATCA
GGCTATGCAGCGGATCAAAAAGCACACAAAATGCCATTAACGGGATTACAAACAAGGTGA
ACTCTGTTATCGAGAAAATGAACATTCAATTCACAGCTGTGGGTAAAGAATTCAACAAATTA
GAAAAAGGATGGAAAATTTAAATAAAAAGTTGATGATGGATTTCTGGACATTTGGACATA
TAATGCAGAATTGTTAGTTCTACTGGAAAATGAAAGGACTCTGGATTTCCATGACTCAAATG
TGAAGAATCTGTATGAGAAAGTAAAAGCCAATTAAAGAATAATGCCAAAGAAATCGGAAAT
GGATGTTTTGAGTTCTACCACAAGTGTGACAATGAATGCATGGAAGTGTAAGAAATGGGA
CTTATGATTATCCCAAATATTCAGAAGAGTCAAAGTTGAACAGGGAAAAGGTAGATGGAGT
GAAATTGGAATCAATGGGGATCTATCAGATTCTGGCGATCTACTCAACTGTCGCCAGTTCA
CTGGTGCTTTTGGTCTCCCTGGGGGCAATCAGTTTCTGGATGTGTTCTAATGGATCTTTGC

FIG. 9 (cont'd)

AGTGCAGAATATGCATCTGAGATTAGAATTTCAGAAATATGAGGAAAAACACCCTTGTTTCTACT (SEQ ID NO:5)

Influenza A virus (A/Puerto Rico/8/1934(H1N1)) segment 6 (NCBI Ref Seq: NC_002018.1)
AGCGAAAGCAGGGGTTTAAAATGAATCCAAATCAGAAAATAATAACCATTGGATCAATCTGT
CTGGTAGTCGGACTAATTAGCCTAATATTGCAAATAGGGAATATAATCTCAATATGGATTAG
CCATTCAATTCAAACTGGAAGTCAAAACCATACTGGAATATGCAACCAAAACATCATTACCT
ATAAAAATAGCACCTGGGTAAAGGACACAACTTCAGTGATATTAACCGGCAATTCATCTCTT
TGTCCCATCCGTGGGTGGGCTATATACAGCAAAGACAATAGCATAAGAATTGGTTCCAAAG
GAGACGTTTTTGTCATAAGAGAGCCCTTTATTTCATGTTCTCACTTGGAATGCAGGACCTTT
TTTCTGACCCAAGGTGCCTTACTGAATGACAGGCATTCAAATGGGACTGTTAAGGACAGAA
GCCCTTATAGGGCCTTAATGAGCTGCCCTGTCGGTGAAGCTCCGTCCCGTACAATTCAA
GATTTGAATCGGTTGCTTGGTCAGCAAGTGCATGTCATGATGGCATGGGCTGGCTAACAAT
CGGAATTTCAGGTCCAGATAATGGAGCAGTGGCTGTATTAAAATACAACGGCATAATAACT
GAAACCATAAAAGTTGGAGGAAGAAAATATTGAGGACACAAGAGTCTGAATGTGCCTGTG
TAAATGGTTCATGTTTTACTATAATGACTGATGGCCCGAGTGATGGGCTGGCCTCGTACAA
AATTTTCAAGATCGAAAAGGGGAAGGTTACTAAATCAATAGAGTTGAATGCACCTAATTCTC
ACTATGAGGAATGTTCCTGTTACCCTGATACCGGCAAAGTGATGTGTGTGCAGAGACAA
TTGGCATGGTTCGAACCGGCCATGGGTGTCTTTCGATCAAAACCTGGATTATCAAATAGGA
TACATCTGCAGTGGGGTTTTCGGTGACAACCCGCGTCCCAAAGATGGAACAGGCAGCTGT
GGTCCAGTGTATGTTGATGGAGCAAACGGAGTAAAGGGATTTTCATATAGGTATGGTAATG
GTGTTTGGATAGGAAGGACCAAAAGTCACAGTTCCAGACATGGGTTTGAGATGATTTGGGA
TCCTAATGGATGGACAGAGACTGATAGTAAGTTCTCTGTGAGGCAAGATGTTGTGGCAATG
ACTGATTGGTCAGGGTATAGCGGGAGTTTCGTTCAACATCCTGAGCTAACAGGGCTAGACT
GTATAAGGCCGTGCTTCTGGGTTGAATTAATCAGGGGACGACCTAAAGAAAAACAATCTG
GACTAGTGCGAGCAGCATTTCTTTTGTGGCGTGAATAGTGATACTGTAGATTGGTCTTGG
CCAGACGGTGCTGAGTTGCCATTCACCATTGACAAGTAGTCTGTTCAAAAAACTCCTTGTTT
CTACT (SEQ ID NO: 6)

Influenza A virus (A/New York/392/2004(H3N2)) segment (NCBI Ref Seq: NC_007366.1)
AGCAAAAGCAGGGGATAATTCTATTAACCATGAAGACTATCATTGCTTTGAGCTACATTCTA
TGTCTGGTTTTCGCTCAAAAACTTCCCGGAAATGACAACAGCACGGCAACGCTGTGCCTTG
GGCACCATGCAGTACCAAACGGAACGATAGTGAAAACAATCACGAATGACCAAATTGAAGT
CACTAATGCTACTGAACTGGTTCAGAGTTCCTCAACAGGTGGAATATGCGACAGTCCTCAT
CAGATCCTTGATGGAGAAAACTGCACACTAATAGATGCTCTATTGGGAGACCCTCAGTGTG
ATGGCTTCCAAAATAAGAAATGGGACCTTTTTGTTGAACGCAGCAAAGCCTACAGCAACTG
TTACCCTTATGATGTGCCGGATTATGCCTCCCTTAGGTCACTAGTTGCCTCATCCGGCACA
CTGGAGTTTAACAATGAAAGCTTCAATTGGACTGGAGTCACTCAAAATGGAACAAGCTCTG
CTTGCAAAAGGAGATCTAATAACAGTTTCTTTAGTAGATTGAATTGGTTGACCCACTTAAAA
TTCAAATACCCAGCATTGAACGTGACTATGCCAAACAATGAAAAATTTGACAAACTGTACAT
TTGGGGGGTTCACCACCCGGGTACGGACAATGACCAAATCAGCCTATATGCTCAAGCATC
AGGAAGAATCACAGTCTCTACCAAAAGAAGCCAACAAACCGTAATCCCGAGTATCGGATCT
AGACCCAGGATAAGGGATGTCCCCAGCAGAATAAGCATCTATTGGACAATAGTAAAACCGG
GAGACATACTTTTGATTAACAGCACAGGGAATCTAATTGCTCCTCGGGGTTACTTCAAAATA
CGAAGTGGGAAAAGCTCAATAATGAGATCAGATGCACCCATTGGCAAATGCAATTCTGAAT
GCATCACTCCAAATGGAAGCATTCCCAATGACAAACCATTTCAAAATGTAAACAGGATCACA
TATGGGGCCTGTCCCAGATATGTTAAGCAAAACACTCTGAAATTGGCAACAGGGATGCGAA
ATGTACCAGAGAAACAAACTAGAGGCATATTTGGCGCAATCGCGGGTTTCATAGAAAATGG
TTGGGAGGGAATGGTAGACGGTTGGTACGGTTTCAGGCATCAAAATTCTGAGGGAACAGG

FIG. 9 (cont'd)

ACAAGCAGCAGATCTCAAAAGCACTCAAGCAGCAATCAACCAAATCAATGGGAAGCTGAAT
AGGTTGATCGGGAAAACAAACGAGAAATTCCATCAGATTGAAAAGAATTCTCAGAAGTAG
AAGGGAGAATTCAGGACCTCGAGAAATATGTTGAGGACACTAAAATAGATCTCTGGTCATA
CAACGCGGAGCTTCTTGTGGCCCTGGAGAACCAACATACAATTGATCTAACTGACTCAGAA
ATGAACAAACTGTTTGAAAGAACAAAGAAGCAACTGAGGGAAAATGCTGAGGATATGGGCA
ATGGTTGTTTCAAAATATACCACAAATGTGACAATGCCTGCATAGGGTCAATCAGAAATGGA
ACTTATGACCATGATGTATACAGAGATGAAGCATTAAACAACCGGTTCCAGATCAAAGGTG
TTGAGTTGAAGTCAGGATACAAAGATTGGATCCTATGGATTTCCTTTGCCATATCATGTTTT
TTGCTTTGTGTTGCTTTGTTGGGGTTCATCATGTGGGCCTGCCAAAAAGGCAACATTAGGT
GCAACATTTGCATTTGAGTGCATTAATTAAAAACACCCTTGTTTCTACT (SEQ ID NO: 7)

Influenza A virus (A/New York/392/2004(H3N2)) segment 6 (NCBI Ref Seq: NC_007368.1)
AGCAAAAGCAGGAGTAAAGATGAATCCAAATCAAAAGATAATAACGATTGGCTCTGTTTCTC
TCACCATTTCCACAATATGCTTCTTCATGCAAATTGCCATCCTGATAACCACTGTAACATTG
CATTTCAAGCAATATGAATTCAACTCCCCCCCAAACAACCAAGTGATGCTGTGTGAACCAA
CAATAATAGAAAGAAACATAACAGAGATAGTGTATCTGACCAACACCACCATAGAGAAGGA
AATGTGCCCCAAACTAGCAGAATACAGAAATTGGTCAAAGCCGCAATGTGACATTACAGGA
TTTGCACCTTTTTCTAAGGACAATTCGATTAGGCTTTCCGCTGGTGGGGACATCTGGGTGA
CAAGAGAACCTTATGTGTCATGCGACCCTGACAAGTGTTACCAATTTGCCCTTGGACAGGG
AACAACACTAAACAACGTGCATTCAAATGACACAGTACATGATAGGACCCCTTATCGGACC
CTATTGATGAATGAATTAGGTGTTCCATTTCATCTGGGGACCAAGCAAGTGTGCATAGCAT
GGTCCAGCTCAAGTTGTCACGATGGAAAAGCATGGCTGCATGTTTGTGTAACGGGGGATG
ATAAAAATGCAACTGCTAGCTTCATTTACAATGGGAGGCTTGTAGATAGTATTGTTTCATGG
TCCAAAAAAATCCTCAGGACCCAGGAGTCAGAATGCGTTTGTATCAATGGAACTTGTACAG
TAGTAATGACTGATGGGAGTGCTTCAGGAAAAGCTGATACTAAAATACTATTCATTGAGGA
GGGGAAAATCATTCATACTAGCACATTGTCAGGAAGTGCTCAGCATGTCGAGGAGTGCTCC
TGCTATCCTCGATATCCTGGTGTCAGATGTGTCTGCAGAGACAACTGGAAAGGCTCCAATA
GGCCCATCGTAGATATAAACATAAAGGATTATAGCATTGTTTCCAGTTATGTGTGCTCAGGG
CTTGTTGGAGACACACCCAGAAAAACGACAGCTCCAGCAGTAGCCATTGCTTGGATCCTA
ACAATGAAGAAGGTGGTCATGGAGTGAAAGGCTGGGCCTTTGATGATGGAAATGACGTGT
GGATGGGAAGAACGATCAGCGAGAAGTTACGCTCAGGATATGAAACCTTCAAAGTCATTGA
AGGCTGGTCCAAACCTAATTCCAAATTGCAGATAAATAGGCAAGTCATAGTTGACAGAGGT
AATAGGTCCGGTTATTCTGGTATTTTCTCTGTTGAAGGCAAAAGCTGCATCAATCGGTGCTT
TTATGTGGAGTTGATAAGGGGAAGAAAAGAGGAAACTGAAGTCTTGTGGACCTCAAACAGT
ATTGTTGTGTTTTGTGGCACCTCAGGTACATATGGAACAGGCTCATGGCCTGATGGGGCG
GACATCAATCTCATGCCTATATAAGCTTTCGCAATTTTAGAAAAAACTCCTTGTTTCTACT
(SEQ ID NO: 8)

Influenza A virus (A/goose/Guangdong/1/1996(H5N1)) hemagglutinin (HA) gene (NCBI Ref Seq: NC_007362.1)
GCAGGGGTATAATCTGTCAAAATGGAGAAAATAGTGCTTCTTCTTGCAATAGTCAGTCTTGT
CAAAAGTGATCAGATTTGCATTGGTTACCATGCAAACAACTCGACAGAGCAGGTTGACACA
ATAATGGAAAAGAACGTTACTGTTACACATGCCCAAGACATACTGGAAAAGACACACAATG
GGAAGCTCTGCGATCTAAATGGAGTGAAGCCTCTCATTTTGAGAGATTGTAGTGTAGCTGG
ATGGCTCCTCGGAAACCCTATGTGTGACGAATTCATCAATGTGCCGGAATGGTCTTACATA
GTGGAGAAGGCCAGTCCAGCCAATGACCTCTGTTACCCAGGGGATTTCAACGACTATGAA
GAACTGAAACACCTATTGAGCAGAACAAACCATTTTGAGAAAATTCAGATCATCCCCAAAAG
TTCTTGGTCCAATCATGATGCCTCATCAGGGGTGAGCTCAGCATGTCCATACCATGGGAGG
TCCTCCTTTTTCAGAAATGTGGTATGGCTTATCAAAAGAACAGTGCATACCCAACAATAAA

FIG. 9 (cont'd)

GAGGAGCTACAATAATACCAACCAAGAAGATCTTTTAGTACTGTGGGGATTCACCATCCT
AATGATGCGGCAGAGCAGACAAAGCTCTATCAAAACCCAACCACTTACATTTCCGTTGGAA
CATCAACACTGAACCAGAGATTGGTTCCAGAAATAGCTACTAGACCCAAAGTAAACGGGCA
AAGTGGAAGAATGGAGTTCTTCTGGACAATTTTAAAGCCGAATGATGCCATCAATTTCGAG
AGTAATGGAAATTTCATTGCTCCAGAATATGCATACAAAATTGTCAAGAAGGGGACTCAGC
AATTATGAAAGTGAATTGGAATATGGTAACTGCAACACCAAGTGTCAAACTCCAATGGGG
GCGATAAACTCTAGTATGCCATTCCACAACATACACCCCTCACCATCGGGGAATGCCCCA
AATATGTGAAATCAAACAGATTAGTCCTTGCGACTGGACTCAGAAATACCCCTCAGAGAGA
GAGAAGAAGAAAAAGAGAGGACTATTTGGAGCTATAGCAGGTTTTATAGAGGGAGGATG
GCAGGGAATGGTAGATGGTTGGTATGGGTACCACCATAGCAATGAGCAGGGGAGTGGATA
CGCTGCAGACAAGAATCCACTCAAAAGGCAATAGATGGAGTCACCAATAAGGTCAACTCG
ATCATTGACAAAATGAACACTCAGTTTGAGGCCGTTGGAAGGGAATTTAATAACTTGGAAA
GGAGGATAGAGAATTTAAACAAGCAGATGGAAGACGGATTCCTAGATGTCTGGACTTATAA
TGCTGAACTTCTGGTTCTCATGGAAAATGAGAGAACTCTAGACTTTCATGACTCAAATGTCA
AGAACCTTTATGACAAGGTCCGACTACAGCTTAGGGATAATGCAAAGGAGCTGGGTAATGG
TTGTTTCGAGTTCTATCACAAATGTGATAATGAATGTATGGAAAGTGTAAAAAACGGAACGT
ATGACTACCCGCAGTATTCAGAAGAAGCAAGACTAAACAGAGAGGAAATAAGTGGAGTAAA
ATTGGAATCAATGGGAACTTACCAAATACTGTCAATTTATTCAACAGTGGCGAGTTCCCTAG
CACTGGCAATCATGGTAGCTGGTCTATCTTTATGGATGTGCTCCAATGGATCGTTACAATG
CAGAATTTGCATTTAAATTTGTGAGTTCAGATTGTAGTTAAAAACACC (SEQ ID NO: 9)

Influenza A virus (A/Goose/Guangdong/1/96(H5N1)) neuraminidase (NA) gene (NCBI Ref Seq: NC_007361.1)
AGCAAAAGCAGGAGATTAAAATGAATCCAAATCAGAAGATAATAACCATTGGATCAATCTGT
ATGGTAGTTGGGATAATTAGCTTGATGTTACAAATTGGGAACATAATCTCAATATGGGTCAG
TCATTCAATTCAGACAGGGAATCAACACCAAGCTGAACCATGCAATCAAAGCATTATTACTT
ATGAAAACAACACCTGGGTAAATCAAACATATGTCAACATCAGCAATACCAATTTTCTTACT
GAAAAAGCTGTGGCTTCAGTAACATTAGCGGGCAATTCATCTCTTTGCCCCATTAGCGGAT
GGGCTGTACACAGTAAGGACAACGGTATAAGAATCGGTTCCAAGGGGGATGTGTTTGTTAT
AAGAGAGCCGTTCATCTCATGCTCCCACTTGGAATGCAGAACTTTCTTTTTGACTCAGGGA
GCCTTGCTGAATGACAAGCACTCCAATGGGACCGTCAAAGACAGAAGCCCTCACAGAACA
TTGATGAGTTGTCCTGTGGGTGAGGCTCCCTCCCCATATAACTCAAGGTTTGAGTCTGTTG
CTTGGTCGGCAAGTGCTTGCCATGATGGCACCAGTTGGTTGACAATTGGAATTTCTGGCCC
AGACAATGGGGCTGTGGCTGTATTGAAATACAACGGCATAATAACAGACACTATCAAGAGT
TGGAGGAACAACATACTGAGAACTCAAGAGTCTGAATGTGCATGTGTAAATGGCTCTTGCT
TTACTGTAATGACTGACGGACCAAGTAATGGGCAGGCCTCATATAAGATCTTCAAAATGGA
AAAAGGGAAAGTAGTTAAATCAGTCGAATTGAATGCCCCTAATTATCACTATGAGGAGTGCT
CCTGTTATCCTGATGCTGGCGAAATCACATGTGTGCAGGGATAATTGGCATGGCTCAAA
TCGGCCATGGGTATCTTTCAATCAAAATTTGGAGTATCAAATAGGATATATGCAGTGGAG
TTTTCGGAGACAATCCACGCCCAATGATGGAACAGGCAGTTGTGGTCCGGTGTCCCCTA
ACGGGGCATATGGAGTAAAAGGGTTTTCATTTAAATACGGCAATGGTGTTTGGATCGGGAG
AACCAAAAGCACTAATTCCAGGAGCGGCTTTGAAATGATTTGGGATCCAAATGGGTGGACT
GGAACGGACAGTAGCTTCTCGGTGAAACAAGATATCGTAGCAATAACTGATTGGTCAGGAT
ATAGCGGGAGTTTTGTCCAGCATCCAGAACTGACAGGATTAGATTGCATAAGACCTTGTTT
CTGGGTTGAGCTAATCAGAGGGCGGCCCAAAGAGAGCACAATTTGGACTAGTGGGAGCAG
CATATCTTTTTGTGGTGTAAATAGTGACACTGTGGGTTGGTCTTGGCCAGACGATGCCGAG
TTGCCATTCACCATTGACAAGTAGTTTGTTCAAAAAACTCCTTGTTTCTACT (SEQ ID NO: 10)

FIG. 9 (cont'd)

Influenza B virus (B/Lee/1940) segment 4 (NCBI Ref Seq: NC_002207.1)
AGCAGAAGCGTTGCATTTTCTAATATCCACAAAATGAAGGCAATAATTGTACTACTCATGGT
AGTAACATCCAATGCAGATCGAATCTGCACTGGGATAACATCGTCAAACTCACCTCATGTG
GTTAAAACTGCCACTCAAGGGGAAGTCAATGTGACTGGTGTGATACCACTAACAACAACAC
CTACCAAATCTCATTTTGCAAATCTCAAAGGAACACAGACCAGAGGAAAACTATGCCCAAA
CTGTTTTAACTGCACAGATCTGGACGTGGCCCTAGGCAGACCAAAATGCATGGGGAACAC
ACCCTCCGCAAAAGTCTCAATACTCCATGAAGTCAAACCTGCTACATCTGGATGCTTTCCTA
TAATGCACGACAGAACAAAAATCAGACAACTACCTAATCTTCTCAGAGGATATGAAAACATC
AGGTTATCAACCAGTAATGTTATCAATACAGAGACGGCACCAGGAGGACCCTACAAGGTG
GGGACCTCAGGATCTTGCCCTAACGTTGCTAATGGGAACGGCTTCTTCAACACAATGGCTT
GGGTTATCCCAAAAGACAACAACAAGACAGCAATAAATCCAGTAACAGTAGAAGTACCATA
CATTTGTTCAGAAGGGGAAGACCAAATTACTGTTTGGGGGTTCCACTCTGATGACAAAACC
CAAATGGAAAGACTCTATGGAGACTCAAATCCTCAAAAGTTCACCTCATCTGCCAATGGAG
TAACCACACATTATGTTTCTCAGATTGGTGGCTTCCCAAATCAAACAGAAGACGAAGGGCT
AAAACAAAGCGGCAGAATTGTTGTTGATTACATGGTACAAAAACCTGGAAAAACAGGAACA
ATTGTTTATCAAAGAGGCATTTTATTGCCTCAAAAAGTGTGGTGCGCAAGTGGCAGGAGCA
AGGTAATAAAAGGGTCCTTGCCTTTAATTGGTGAAGCAGATTGCCTCCACGAAAGTACGG
TGGATTAAATAAAAGCAAGCCTTACTACACAGGAGAGCATGCAAAGGCCATAGGAAATTGC
CCAATATGGGTGAAAACACCCTTGAAGCTGGCCAATGGAACCAAATATAGACCGCCTGCAA
AACTATTAAAGGAAAGAGGTTTCTTCGGAGCTATTGCTGGTTTCTTGGAAGGAGGATGGGA
AGGAATGATTGCAGGTTGGCACGGATACACATCTCATGGAGCACATGGAGTGGCAGTGGC
AGCAGACCTTAAGAGTACACAAGAAGCTATAAACAAGATAACAAAAAATCTCAACTATTTAA
GTGAGCTAGAAGTAAAAAACCTTCAAAGACTAAGCGGAGCAATGAATGAGCTTCACGACGA
AATACTCGAGCTAGACGAAAAGTGGATGATCTAAGAGCTGATACAATAAGCTCACAAATA
GAGCTTGCAGTCTTGCTTTCCAACGAAGGGATAATAAACAGTGAAGATGAGCATCTCTTGG
CACTTGAAAGAAAACTGAAGAAAATGCTTGGCCCCTCTGCTGTAGAAATAGGGAATGGGTG
CTTTGAAACCAAACACAAATGCAACCAGACTTGCCTAGACAGGATAGCTGCTGGCACCTTT
AATGCAGGAGATTTTCTCTTCCCACTTTTGATTCATTAAACATTACTGCTGCATCTTTAAAT
GATGATGGCTTGGATAATCATACTATACTGCTCTACTACTCAACTGCTGCTTCTAGCTTGGC
TGTAACATTAATGATAGCTATCTTCATTGTCTACATGGTCTCCAGAGACAATGTTTCTTGTTC
CATCTGTCTGTGAGGGAGATTAAGCCCTGTGTTTTCCTTTACTGTAGTGCTCATTTGCTTGT
CACCATTACAAAGAAACGTTATTGAAAATGCTCTTGTTACTACT (SEQ ID NO:11)

Influenza B virus (B/Lee/1940) segment 6 (NCBI Ref Seq: NC_002209.1)
AGCAGAAGCAGAGCATATTCTTAGAACTGAAGTGAACAGGCCAAAA<u>ATGAACAATGCTACC</u>
<u>TTCAACTGTACAAACATTAACCCTATTACTCACATCAGGGGGAGTATTATTATCACTATATGT</u>
<u>GTCAGCCTCATTGTCATACTTATTGTATTCGGATGTATTGCTAAAATTTTCATCAACAAAAAC</u>
<u>AACTGCACCAACAATGTCATTAGAGTGCACAAACGCATCAAATGCCCAGACTGTGAACCAT</u>
<u>TCTGCAACAAAGAGATGACATTTCCACCCCAGAGCCGGAGTGGACATACCCTCGTTTAT</u>
<u>CTTGCCAGGGCTCAACCTTTCAGAAGGCACTCCTAATTAGCCCTCATAGGTTCGGAGAGAT</u>
<u>CAAAGGAAACTCAGCTCCCTTGATAATAAGAGAACCTTTTGTTGCTTGTGGACCAAAGAAT</u>
<u>GCAGACACTTTGCTCTGACCCATTATGCAGCTCAGCCGGGGGGATACTACAATGGAACAA</u>
<u>GAAAGGACAGAAACAAGCTGAGGCATCTAGTATCAGTCAAATTGGGAAAATCCCAACTGT</u>
<u>GGAAAACTCCATTTTCCACATGGCAGCTTGGAGCGGATCCGCATGCCATGATGGTAGAGA</u>
<u>ATGGACATATATCGGAGTTGATGGTCCTGACAATGATGCATTGGTCAAAATAAAATATGGA</u>
<u>GAAGCATATACTGACACATATCATTCCTATGCACACAACATCCTAAGAACACAAGAAAGTGC</u>
<u>CTGCAATTGCATCGGGGGAGATTGTTATCTTATGATAACAGACGGCTCAGCTTCAGGAATT</u>
<u>AGTAAATGCAGATTTCTTAAAATTAGAGAGGGTCGAATAATAAAGAAATACTTCCAACAGG</u>
<u>AAGAGTGGAGCACACTGAAGAGTGCACATGCGGGTTCGCCAGCAATAAAACCATAGAATG</u>

FIG. 9 (cont'd)

TGCCTGTAGAGACAACAGTTACACAGCAAAAGACCCTTTGTCAAATTAAATGTGGAAACT
GATACAGCTGAAATAAGATTGATGTGCACAAAGACTTATCTAGACACTCCCAGACCGGATG
ATGGAAGCATAGCAGGGCCTTGCGAATCTAATGGAGACAAGTGGCTTGGAGGCATCAAAG
GAGGATTCGTCCATCAAAGAATGGCATCTAAGATTGGAAGATGGTACTCCCGAACGATGTC
TAAAACTAACAGAATGGGGATGGAACTGTATGTAAAGTATGATGGTGACCCATGGACTGAC
AGTGATGCTCTTACTCTTAGTGGAGTAATGGTTTCCATAGAAGAACCTGGTTGGTATTCTTT
TGGCTTCGAAATAAAGGACAAGAAATGTGATGTCCCTTGTATTGGGATAGAGATGGTACAC
GATGGTGGAAAAGATACTTGGCATTCAGCTGCAACAGCCATTTACTGTTTGATGGGCTCAG
GACAATTGCTATGGGACACTGTCACAGGCGTTGATATGGCTTTATAATAGAGGAATGGTTG
GATCTGTTCTAAACCCTTTGTTCCTATTTTATTTGAACAGTTGTTCTTACTAGATTTAATTGTT
TCTGAAAAATGCTCTTGTTACTACT (SEQ ID NO:12)

Influenza A virus (A/Puerto Rico/8/1934(H1N1)) segment 1 (NCBI Ref Seq: NC_002023.1)
AGCGAAAGCAGGTCAATTATATTCAATATGGAAAGAATAAAAGAACTAAGAAATCTAATGTC
GCAGTCTCGCACCCGCGAGATACTCACAAAAACCACCGTGGACCATATGGCCATAATCAA
GAAGTACACATCAGGAAGACAGGAGAAGAACCCAGCACTTAGGATGAAATGGATGATGGC
AATGAAATATCCAATTACAGCAGACAAGAGGATAACGGAAATGATTCCTGAGAGAAATGAG
CAAGGACAAACTTTATGGAGTAAAATGAATGATGCCGGATCAGACCGAGTGATGGTATCAC
CTCTGGCTGTGACATGGTGGAATAGGAATGGACCAATGACAAATACAGTTCATTATCCAAA
AATCTACAAAACTTATTTTGAAAGAGTCGAAAGGCTAAAGCATGGAACCTTTGGCCCTGTCC
ATTTTAGAAACCAAGTCAAAATACGTCGGAGAGTTGACATAAATCCTGGTCATGCAGATCTC
AGTGCCAAGGAGGCACAGGATGTAATCATGGAAGTTGTTTTCCCTAACGAAGTGGGAGCC
AGGATACTAACATCGGAATCGCAACTAACGATAACCAAAGAGAAGAAAGAAGAACTCCAGG
ATTGCAAAATTTCTCCTTTGATGGTTGCATACATGTTGGAGAGAGAACTGGTCCGCAAAAC
GAGATTCCTCCCAGTGGCTGGTGGAACAAGCAGTGTGTACATTGAAGTGTTGCATTTGACT
CAAGGAACATGCTGGGAACAGATGTATACTCCAGGAGGGGAAGTGAAGAATGATGATGTT
GATCAAAGCTTGATTATTGCTGCTAGGAACATAGTGAGAAGAGCTGCAGTATCAGCAGACC
CACTAGCATCTTTATTGGAGATGTGCCACAGCACACAGATTGGTGGAATTAGGATGGTAGA
CATCCTTAAGCAGAACCCAACAGAAGAGCAAGCCGTGGGTATATGCAAGGCTGCAATGGG
ACTGAGAATTAGCTCATCCTTCAGTTTTGGTGGATTCACATTTAAGAGAACAAGCGGATCAT
CAGTCAAGAGAGAGGAAGAGGTGCTTACGGGCAATCTTCAAACATTGAAGATAAGAGTGC
ATGAGGGATATGAAGAGTTCACAATGGTTGGGAGAAGAGCAACAGCCATACTCAGAAAAG
CAACCAGGAGATTGATTCAGCTGATAGTGAGTGGGAGAGACGAACAGTCGATTGCCGAAG
CAATAATTGTGGCCATGGTATTTTCACAAGAGGATTGTATGATAAAAGCAGTTAGAGGTGAT
CTGAATTTCGTCAATAGGGCGAATCAGCGACTGAATCCTATGCATCAACTTTTAAGACATTT
TCAGAAGGATGCGAAAGTGCTTTTTCAAAATTGGGGAGTTGAACCTATCGACAATGTGATG
GGAATGATTGGGATATTGCCCGACATGACTCCAAGCATCGAGATGTCAATGAGAGGAGTG
AGAATCAGCAAAATGGGTGTAGATGAGTACTCCAGCACGGAGAGGGTAGTGGTGAGCATT
GACCGGTTCTTGAGAGTCCGGGACCAACGAGGAAATGTACTACTGTCTCCCGAGGAGGTC
AGTGAAACACAGGGAACAGAGAAACTGACAATAACTTACTCATCGTCAATGATGTGGGAGA
TTAATGGTCCTGAATCAGTGTTGGTCAATACCTATCAATGGATCATCAGAAACTGGGAAACT
GTTAAAATTCAGTGGTCCCAGAACCCTACAATGCTATACAATAAAATGGAATTTGAACCATT
TCAGTCTTTAGTACCTAAGGCCATTAGAGGCCAATACAGTGGGTTTGTGAGAACTCTGTTC
CAACAAATGAGGGATGTGCTTGGGACATTTGATACCGCACAGATAATAAAACTTCTTCCCTT
CGCAGCCGCTCCACCAAAGCAAAGTAGAATGCAGTTCTCCTCATTTACTGTGAATGTGAGG
GGATCAGGAATGAGAATACTTGTAAGGGGCAATTCTCCTGTATTCAACTACAACAAGGCCA
CGAAGAGACTCACAGTTCTCGGAAAGGATGCTGGCACTTTAACCGAAGACCCAGATGAAG
GCACAGCTGGAGTGGAGTCCGCTGTTCTGAGGGGATTCCTCATTCTGGGCAAAGAAGACA
GGAGATATGGGCCAGCATTAAGCATCAATGAACTGAGCAACCTTGCGAAAGGAGAGAAGG

FIG. 9 (cont'd)

CTAATGTGCTAATTGGGCAAGGAGACGTGGTGTTGGTAATGAAACGAAAACGGGACTCTA
GCATACTTACTGACAGCCAGACAGCGACCAAAAGAATTCGGATGGCCATCAATTAGTGTCG
AATAGTTTAAAAACGACCTTGTTTCTACT (SEQ ID NO: 13)

Influenza A virus (A/Puerto Rico/8/1934(H1N1)) segment 2 (NCBI Ref Seq: NC_002021.1)
AGCGAAAGCAGGCAAACCATTTGAATGGATGTCAATCCGACCTTACTTTTCTTAAAAGTGC
CAGCACAAAATGCTATAAGCACAACTTTCCCTTATACCGGAGACCCTCCTTACAGCC<u>ATGG
GACAGGAACAGGATACACCATGGATACTGTCAACAGGACACATCAGTACTCAGAAAAGGC
AAGATGGACAACAAACACCGAAACTGGAGCACCGCAACTCAACCCGATTGATGGGCCACT
GCCAGAAGACAATGAACCAAGTGGTTATGCCCAAACAGATTGTGTATTGGAAGCAATGGCT
TTCCTTGAGGAATCCCATCCTGGTATTTTTGAAAACTCGTGTATTGAACGATGGAGGTTGT
TCAGCAAACACGAGTAG</u>ACAAGCTGACACAAGGCCGACAGACCTATGACTGGACTTTAAAT
AGAAACCAGCCTGCTGCAACAGCATTGGCCAACACAATAGAAGTGTTCAGATCAAATGGCC
TCACGGCCAATGAGTCTGGAAGGCTCATAGACTTCCTTAAGGATGTAATGGAGTCAATGAA
AAAAGAAGAAATGGGGATCACAACTCATTTTCAGAGAAAGAGACGGGTGAGAGACAATATG
ACTAAGAAAATGATAACACAGAGAACAATAGGTAAAAGGAAACAGAGATTGAACAAAGGA
GTTATCTAATTAGAGCATTGACCCTGAACACAATGACCAAAGATGCTGAGAGAGGGAAGCT
AAAACGGAGAGCAATTGCAACCCCAGGGATGCAAATAAGGGGGTTTGTATACTTTGTTGAG
ACACTGGCAAGGAGTATATGTGAGAAACTTGAACAATCAGGGTTGCCAGTTGGAGGCAAT
GAGAAGAAAGCAAAGTTGGCAAATGTTGTAAGGAAGATGATGACCAATTCTCAGGACACCG
AACTTTCTTTGACCATCACTGGAGATAACACCAAATGGAACGAAAATCAGAATCCTCGGAT
GTTTTTGGCCATGATCACATATATGACCAGAAATCAGCCCGAATGGTTCAGAAATGTTCTAA
GTATTGCTCCAATAATGTTCTCAAACAAAATGGCGAGACTGGGAAAAGGGTATATGTTTGA
GAGCAAGAGTATGAAACTTAGAACTCAAATACCTGCAGAAATGCTAGCAAGCATTGATTTG
AAATATTTCAATGATTCAACAAGAAGGAAGATTGAAAAAATCCGACCGCTCTTAATAGAGGG
GACTGCATCATTGAGCCCTGGAATGATGATGGGCATGTTCAATATGTTAAGCACTGTATTA
GGCGTCTCCATCCTGAATCTTGGACAAAAGAGATACACCAAGACTACTTACTGGTGGGATG
GTCTTCAATCCTCTGACGATTTTGCTCTGATTGTGAATGCACCCAATCATGAAGGGATTCAA
GCCGGAGTCGACAGGTTTTATCGAACCTGTAAGCTACATGGAATCAATATGAGCAAGAAA
AGTCTTACATAAACAGAACAGGTACATTTGAATTCACAAGTTTTTCTATCGTTATGGGTTTG
TTGCCAATTTCAGCATGGAGCTTCCAGTTTTGGTGTGTCTGGGAGCAACGAGTCAGCGG
ACATGAGTATTGGAGTTACTGTCATCAAAAACAATATGATAAACAATGATCTTGGTCCAGCA
ACAGCTCAAATGGCCCTTCAGTTGTTCATCAAAGATTACAGGTACACGTACCGATGCCATA
GAGGTGACACACAAATACAAACCCGAAGATCATTTGAAATAAAGAAACTGTGGGAGCAAAC
CCGTTCCAAAGCTGGACTGCTGGTCTCCGACGGAGGCCCAAATTTATACAACATTAGAAAT
CTCCACATTCCTGAAGTCTGCCTAAAATGGGAATTGATGGATGAGGATTACCAGGGGCGTT
TATGCAACCCACTGAACCCATTTGTCAGCCATAAAGAAATTGAATCAATGAACAATGCAGTG
ATGATGCCAGCACATGGTCCAGCCAAAAACATGGAGTATGATGCTGTTGCAACAACACACT
CCTGGATCCCCAAAAGAAATCGATCCATCTTGAATACAAGTCAAAGAGGAGTACTTGAAGA
TGAACAAATGTACCAAAGGTGCTGCAATTTATTTGAAAAATTCTTCCCCAGCAGTTCATACA
GAAGACCAGTCGGGATATCCAGTATGGTGGAGGCTATGGTTTCCAGAGCCCGAATTGATG
CACGGATTGATTTCGAATCTGGAAGGATAAAGAAGAAGAGTTCACTGAGATCATGAAGAT
CTGTTCCACCATTGAAGAGCTCAGACGGCAAAAATAGTGAATTTAGCTTGTCCTTCATGAAA
AAATGCCTTGTTCCTACT (SEQ ID NO: 14)

FIG. 9 (cont'd)

Influenza A virus (A/Puerto Rico/8/1934(H1N1)) segment 3 (NCBI Ref Seq: NC_002022.1)
AGCGAAAGCAGGTACTGATCCAAAATGGAAGATTTTGTGCGACAATGCTTCAATCCGATGA
TTGTCGAGCTTGCGGAAAAAACAATGAAAGAGTATGGGGAGGACCTGAAAATCGAAACAAA
CAAATTTGCAGCAATATGCACTCACTTGGAAGTATGCTTCATGTATTCAGATTTCCACTTCA
TCAATGAGCAAGGCGAGTCAATAATCGTAGAACTTGGTGATCCTAATGCACTTTTGAAGCA
CAGATTTGAAATAATCGAGGGAAGAGATCGCACAATGGCCTGGACAGTAGTAAACAGTATT
TGCAACACTACAGGGGCTGAGAAACCAAAGTTTCTACCAGATTTGTATGATTACAAGGAAA
ATAGATTCATCGAAATTGGAGTAACAAGGAGAGAAGTTCACATATACTATCTGGAAAAGGC
CAATAAAATTAAATCTGAGAAAACACACATCCACATTTTCTCGTTCACTGGGGAAGAAATGG
CCACAAAGGCCGACTACACTCTCGATGAAGAAAGCAGGGCTAGGATCAAAACCAGGCTAT
TCACCATAAGACAAGAAATGGCCAGCAGAGGCCTCTGGGATTCCTTTCGTCAGTCCGAGA
GAGGAGAAGAGACAATTGAAGAAAGGTTTGAAATCACAGGAACAATGCGCAAGCTTGCCG
ACCAAAGTCTCCCGCCGAACTTCTCCAGCCTTGAAAATTTTAGAGCCTATGTGGATGGATT
CGAACCGAACGGCTACATTGAGGGCAAGCTGTCTCAAATGTCCAAAGAAGTAAATGCTAGA
ATTGAACCTTTTTTGAAAACAACACCACGACCACTTAGACTTCCGAATGGGCCTCCCTGTTC
TCAGCGGTCCAAATTCCTGCTGATGGATGCCTTAAAATTAAGCATTGAGGACCCAAGTCAT
GAAGGAGAGGGAATACCGCTATATGATGCAATCAAATGCATGAGAACATTCTTTGGATGGA
AGGAACCCAATGTTGTTAAACCACACGAAAAGGGAATAAATCCAAATTATCTTCTGTCATGG
AAGCAAGTACTGGCAGAACTGCAGGACATTGAGAATGAGGAGAAAATTCCAAAGACTAAAA
ATATGAAAAAAACAAGTCAGCTAAAGTGGGCACTTGGTGAGAACATGGCACCAGAAAAGGT
AGACTTTGACGACTGTAAAGATGTAGGTGATTTGAAGCAATATGATAGTGATGAACCAGAAT
TGAGGTCGCTTGCAAGTTGGATTCAGAATGAGTTCAACAAGGCATGCGAACTGACAGATTC
AAGCTGGATAGAGCTTGATGAGATTGGAGAAGATGTGGCTCCAATTGAACACATTGCAAGC
ATGAGAAGGAATTATTTCACATCAGAGGTGTCTCACTGCAGAGCCACAGAATACATAATGA
AGGGGGTGTACATCAATACTGCCTTACTTAATGCATCTTGTGCAGCAATGGATGATTTCCAA
TTAATTCCAATGATAAGCAAGTGTAGAACTAAGGAGGGAAGGCGAAAGACCAACTTGTATG
GTTTCATCATAAAAGGAAGATCCCACTTAAGGAATGACACCGACGTGGTAAACTTTGTGAG
CATGGAGTTTTCTCTCACTGACCCAAGACTTGAACCACACAAATGGGAGAAGTACTGTGTT
CTTGAGATAGGAGATATGCTTCTAAGAAGTGCCATAGGCCAGGTTTCAAGGCCCATGTTCT
TGTATGTGAGGACAAATGGAACCTCAAAAATTAAAATGAAATGGGGAATGGAGATGAGGCG
TTGTCTCCTCCAGTCACTTCAACAAATTGAGAGTATGATTGAAGCTGAGTCCTCTGTCAAAG
AGAAAGACATGACCAAAGAGTTCTTTGAGAACAAATCAGAAACATGGCCCATTGGAGAGTC
TCCCAAAGGAGTGGAGGAAAGTTCCATTGGGAAGGTCTGCAGGACTTTATTAGCAAAGTC
GGTATTTAACAGCTTGTATGCATCTCCACAACTAGAAGGATTTTCAGCTGAATCAAGAAAAC
TGCTTCTTATCGTTCAGGCTCTTAGGGACAATCTGGAACCTGGGACCTTTGATCTTGGGGG
GCTATATGAAGCAATTGAGGAGTGCCTAATTAATGATCCCTGGGTTTTGCTTAATGCTTCTT
GGTTCAACTCCTTCCTTACACATGCATTGAGTTAGTTGTGGCAGTGCTACTATTTGCTATCC
ATACTGTCCAAAAAAGTACCTTGTTTCTACT (SEQ ID NO: 15)

Influenza A virus (A/Puerto Rico/8/1934(H1N1)) segment 5 (NCBI Ref Seq: NC_002019.1)
AGCAAAAGCAGGGTAGATAATCACTCACTGAGTGACATCAAAATCATGGCGTCCCAAGGCA
CCAAACGGTCTTACGAACAGATGGAGACTGATGGAGAACGCCAGAATGCCACTGAAATCA
GAGCATCCGTCGGAAAAATGATTGGTGGAATTGGACGATTCTACATCCAAATGTGCACAGA
ACTTAAACTCAGTGATTATGAGGGACGGTTGATCCAAAACAGCTTAACAATAGAGAGAATG
GTGCTCTCTGCTTTTGACGAAGGAGAAATAAATACCTGGAAGAACATCCCAGTGCGGGGA
AGGATCCTAAGAAACTGGAGGACCTATATACAGAAGAGTAAACGGAAGTGGATGAGAG
AACTCATCCTTTATGACAAAGAAGAAATAAGGCGAATCTGGCGCCAAGCTAATAATGGTGA
CGATGCAACGGCTGGTCTGACTCACATGATGATCTGGCATTCCAATTTGAATGATGCAACT
TATCAGAGGACAAGGGCTCTTGTTCGCACCGGAATGGATCCCAGGATGTGCTCTCTGATG

FIG. 9 (cont'd)

CAAGGTTCAACTCTCCCTAGGAGGTCTGGAGCCGCAGGTGCTGCAGTCAAAGGAGTTGGA
ACAATGGTGATGGAATTGGTCAGGATGATCAAACGTGGGATCAATGATCGGAACTTCTGGA
GGGGTGAGAATGGACGAAAAACAAGAATTGCTTATGAAAGAATGTGCAACATTCTCAAAGG
GAAATTTCAAACTGCTGCACAAAAAGCAATGATGGATCAAGTGAGAGAGAGCCGGGACCC
AGGGAATGCTGAGTTCGAAGATCTCACTTTTCTAGCACGGTCTGCACTCATATTGAGAGGG
TCGGTTGCTCACAAGTCCTGCCTGCCTGCCTGTGTGTATGGACCTGCCGTAGCCAGTGGG
TACGACTTTGAAAGAGAGGGATACTCTCTAGTCGGAATAGACCCTTTCAGACTGCTTCAAA
ACAGCCAAGTGTACAGCCTAATCAGACCAAATGAGAATCCAGCACACAAGAGTCAACTGGT
GTGGATGGCATGCCATTCTGCCGCATTTGAAGATCTAAGAGTATTGAGCTTCATCAAAGGG
ACGAAGGTGGTCCCAAGAGGGAAGCTTTCCACTAGAGGAGTTCAAATTGCTTCCAATGAAA
ATATGGAGACTATGGAATCAAGTACACTTGAACTGAGAAGCAGGTACTGGGCCATAAGGAC
CAGAAGTGGAGGAAACACCAATCAACAGAGGGCATCTGCGGGCCAAATCAGCATACAACC
TACGTTCTCAGTACAGAGAAATCTCCCTTTTGACAGAACAACCGTTATGGCAGCATTCACTG
GGAATACAGAGGGGAGAACATCTGACATGAGGACCGAAATCATAAGGATGATGGAAAGTG
CAAGACCAGAAGATGTGTCTTTCCAGGGGCGGGGAGTCTTCGAGCTCTCGGACGAAAAGG
CAGCGAGCCCGATCGTGCCTTCCTTTGACATGAGTAATGAAGGATCTTATTTCTTCGGAGA
CAATGCAGAGGAGTACGACAATTAAAGAAAAATACCCTTGTTTCTACT (SEQ ID NO: 16)

Influenza A virus (A/Puerto Rico/8/1934(H1N1)) segment 7 (NCBI Ref Seq: NC_002016.1)
AGCGAAAGCAGGTAGATATTGAAAG<u>ATGAGTCTTCTAACCGAGGTCGAAACGTACGTTCTC
TCTATCATCCCGTCAGGCCCCCTCAAAGCCGAGATCGCACAGAGACTTGAAGATGTCTTTG
CAGGGAAGAACACCGATCTTGAGGTTCTCATGGAATGGCTAAAGACAAGACCAATCCTGTC
ACCTCTGACTAAGGGGATTTTAGGATTTGTGTTCACGCTCACCGTGCCCAGTGAGCGAGG
ACTGCAGCGTAGACGCTTTGTCCAAAATGCCCTTAATGGGAACGGGGATCCAAATAACATG
GACAAAGCAGTTAAACTGTATAGGAAGCTCAAGAGGGAGATAACATTCCATGGGGCCAAA
GAAATCTCACTCAGTTATTCTGCTGGTGCACTTGCCAGTTGTATGGGCCTCATATACAACA
GGATGGGGGCTGTGACCACTGAAGTGGCATTTGGCCTGGTATGTGCAACCTGTGAACAGA
TTGCTGACTCCCAGCATCGGTCTCATAGGCAAATGGTGACAACAACCAACCCACTAATCAG
ACATGAGAACAGAATGGTTTTAGCCAGCACTACAGCTAAGGCTATGGAGCAAATGGCTGGA
TCGAGTGAGCAAGCAGCAGAGGCCATGGAGGTTGCTAGTCAGGCTAGGCAAATGGTGCAA
GCGATGAGAACCATTGGGACTCATCCTAGCTCCAGTGCTGGTCTGAAAAATGATCTTCTTG
AAAATTTGCAGGCCTATCAGAAACGAATGGGGGTGCAGATGCAACGGTTCAAGTGATCCTC
TCGCTATTGCCGCAAATATCATTGGGATCTTGCACTTGATATTGTGGATTCTTGATCGTCTT
TTTTTCAAATGCATTTACCGTCGCTTTAAATACGGACTGAAAGGAGGGCCTTCTACGGAAG
GAGTGCCAAAGTCTATGAGGGAAGAATATCGAAAGGAACAGCAGAGTGCTGTGGATGCTG
ACGATGGTCATTTTGTCAGCATAGAGCTGGAGTAAAAAACTACCTTGTTTCTACT</u> (SEQ ID NO: 17)

Influenza A virus (A/Puerto Rico/8/1934(H1N1)) segment 8 (NCBI Ref Seq: NC_002020.1)
AGCAAAAGCAGGGTGACAAAGACATA<u>ATGGATCCAAACACTGTGTCAAGCTTTCAGGTAGA
TTGCTTTCTTTGGCATGTCCGCAAACGAGTTGCAGACCAAGAACTAGGTGATGCCCCATTC
CTTGATCGGCTTCGCCGAGATCAGAAATCCCTAAGAGGAAGGGGCAGCACTCTTGGTCTG
GACATCGAGACAGCCACACGTGCTGGAAAGCAGATAGTGGAGCGGATTCTGAAAGAAGAA
TCCGATGAGGCACTTAAAATGACCATGGCCTCTGTACCTGCGTCGCGTTACCTAACCGACA
TGACTCTTGAGGAAATGTCAAGGGAATGGTCCATGCTCATACCCAAGCAGAAAGTGGCAG
GCCCTCTTTGTATCAGAATGGACCAGGCGATCATGGATAAAAACATCATACTGAAAGCGAA
CTTCAGTGTGATTTTTGACCGGCTGGAGACTCTAATATTGCTAAGGGCTTTCACCGAAGAG
GGAGCAATTGTTGGCGAAATTTCACCATTGCCTTCTCTTCCAGGACATACTGCTGAGGATG
TCAAAAATGCAGTTGGAGTCCTCATCGGAGGACTTGAATGGAATGATAACACAGTTCGAGT</u>

FIG. 9 (cont'd)

CTCTGAAACTCTACAGAGATTCGCTTGGAGAAGCAGTAATGAGAATGGGAGACCTCCACTC
ACTCCAAAACAGAAACGAGAAATGGCGGGAACAATTAGGTCAGAAGTTTGAAGAAATAAGA
TGGTTGATTGAAGAAGTGAGACACAAACTGAAGGTAACAGAGAATAGTTTTGAGCAAATAA
CATTTATGCAAGCCTTACATCTATTGCTTGAAGTGGAGCAAGAGATAAGAACTTTCTCATTT
CAGCTTATTTAATAATAAAAAACACCCTTGTTTCTACT (SEQ ID NO: 18)

Influenza A virus (A/New York/392/2004(H3N2)) segment 1 (NCBI Ref Seq: NC_007373.1)
AGCAAAAGCAGGTCAATTATATTCAGTATGGAAAGAATAAAAGAACTACGGAACCTGATGT
CGCAGTCTCGCACTCGCGAGATACTGACAAAAACCACAGTGGACCATATGGCCATAATTAA
GAAGTACACATCGGGGAGACAGGAAAAGAACCCGTCACTTAGGATGAAATGGATGATGGC
AATGAAATACCCAATCACTGCTGACAAAAGGATAACAGAAATGGTTCCGGAGAGAAATGAA
CAAGGACAAACTCTATGGAGTAAAATGAGTGATGCTGGATCAGATCGAGTGATGGTATCAC
CTTTGGCTGTAACATGGTGGAATAGAAATGGACCCGTGGCAAGTACGGTCCATTACCCAAA
AGTATACAAGACTTATTTTGACAAAGTCGAAAGGTTAAAACATGGAACCTTTGGCCCTGTTC
ATTTTAGAAATCAAGTCAAGATACGCAGAAGAGTAGACATAAACCCTGGTCATGCAGACCT
CAGTGCCAAAGAGGCACAAGATGTAATTATGGAAGTTGTTTTTCCCAATGAAGTGGGAGCC
AGGATACTAACATCAGAATCGCAATTAACAATAACTAAAGAGAAAAAGAAGAACTCCGAGA
TTGCAAAATTTCTCCCTTGATGGTTGCATACATGTTAGAGAGAGAACTTGTCCGAAAACAA
GATTTCTCCCAGTTGCTGGCGGAACAAGCAGTATATACATTGAAGTCTTACATTTGACTCAA
GGAACGTGTTGGGAACAAATGTACACTCCAGGTGGAGAAGTGAGGAATGACGATGTTGAC
CAAAGCCTAATTATTGCGGCCAGGAACATAGTAAGAAGAGCTGCAGTATCAGCAGATCCAC
TAGCATCTTTATTGGAGATGTGCCACAGCACACAAATTGGCGGGACAAGGATGGTGGACAT
TCTTAGACAGAACCCGACTGAAGAACAAGCTGTGGATATATGCAAGGCTGCAATGGGATTG
AGAATCAGCTCATCCTTCAGCTTTGGTGGGTTTACATTTAAAAGAACAAGCGGGTCATCAG
TCAAAAAAGAGGAAGAAGTGCTTACAGGCAATCTCCAAACATTGAAGATAAGAGTACATGA
GGGGTATGAGGAGTTCACAATGGTGGGGAAAAGAGCAACAGCTATACTCAGAAAAGCAAC
CAGAAGATTGGTTCAGCTCATAGTGAGTGGAAGAGACGAACAGTCAATAGCCGAAGCAATA
ATCGTGGCCATGGTGTTTTCACAAGAGGATTGCATGATAAAAGCAGTTAGAGGTGACCTGA
ATTTCGTCAACAGAGCAAATCAACGGTTGAACCCCATGCATCAGCTTTTAAGGCATTTTCAG
AAAGATGCGAAAGTGCTTTTTCAAAATTGGGGAATTGAACACATCGACAGTGTGATGGGAA
TGGTTGGAGTATTACCAGATATGACTCCAAGCACAGAGATGTCAATGAGAGGAATAAGAGT
CAGCAAAATGGGTGTGGATGAATACTCCAGTACAGAGAGGGTGGTGGTTAGCATTGATCG
GTTTTTGAGAGTTCGAGACCAACGCGGGAATGTATTATTGTCTCCTGAGGAGGTCAGTGAA
ACACAGGGAACTGAAAGATTGACAATAACATATTCATCGTCGATGATGTGGGAGATTAACG
GTCCTGAGTCGGTTTTGGTCAATACCTATCAATGGATCATCAGAAATTGGGAAGCTGTCAA
AATTCAATGGTCTCAGAATCCTGCAATGTTGTACAACAAAATGGAATTTGAACCATTTCAAT
CTTTAGTCCCCAAGGCCATTAGAAGCCAATACAGTGGGTTTGTCAGAACTCTATTCCAACA
AATGAGAGACGTACTTGGGACATTTGACACCACCCAGATAATAAAGCTTCTCCCTTTTGCA
GCCGCTCCACCAAAGCAAAGCAGAATGCAGTTCTCTTCACTGACTGTAAATGTGAGGGGAT
CAGGGATGAGAATACTTGTAAGGGGCAATTCTCCTGTATTCAACTACAACAAGACCACTAA
AAGACTAACAATTCTCGGAAAGATGCCGGCACTTTAATTGAAGACCCAGATGAAAGCACA
TCCGGAGTGGAGTCCGCCGTCTTGAGAGGGTTTCTCATTATAGGTAAGGAAGACAGAAGA
TACGGACCAGCATTAAGCATCAATGAACTGAGTAACCTTGCAAAGGGGAAAGGCTAATG
TGCTAATCGGGCAAGGAGACGTGGTGTTGGTAATGAAACGAAACGGGACTCTAGCATAC
TTACTGACAGCCAGACAGCGACCAAAAGAATTCGGATGGCCATCAATTAATGTTGAATAGT
TTAAAAACGACCTTGTTTCTACT (SEQ ID NO: 19)

FIG. 9 (cont'd)

Influenza A virus (A/New York/392/2004(H3N2)) segment 2 (NCBI Ref Seq: NC_007372.1)
AGCAAAAGCAGGCAAACCATTTGAATGGATGTCAATCCGACTCTACTGTTCCTAAAGGTTC
CAGCGCAAAATGCCATAAGCACCACATTCCCTTATACTGGAGATCCTCCATACAGCCATGG
AACAGGAACAGGATACACCATGGACACAGTCAACAGAACACACCAATATTCAGAGAAGGG
GAAGTGGACGACAAATACAGAAACTGGGGCACCCCAACTCAACCCAATTGATGGACCACT
ACCTGAGGATAATGAGCCAAGTGGATATGCACAAACAGACTGTGTCCTGGAGGCTATGGC
CTTCCTTGAAGAATCCCACCCAGGTATCTTTGAGAACTCATGCCTTGAAACAATGGAAGTC
GTTCAACAAACAAGGGTGGACAAACTAACCCAAGGCCGCCAGACTTATGATTGGACATTAA
ACAGAAATCAACCGGCAGCAACTGCATTAGCCAACACCATAGAAGTTTTTAGATCGAATGG
ACTAACAGCCAATGAATCAGGAAGGCTAATAGATTTCCTCAAGGATGTGATGGAATCAATG
GATAAAGAGGAAATGGAGATAACAACACACTTTCAAAGAAAAGGAGAGTAAGAGACAACA
TGACCAAGAAAATGGTCACACAAGAACAATAGGGAAGAAAAACAAAGAGTGAATAAGAG
AGGCTATCTAATAAGAGCTTTGACATTGAACACGATGACCAAGATGCAGAGAGAGGTAAA
TTAAAAAGAAGGGCTATTGCAACACCCGGGATGCAAATTAGAGGGTTCGTGTACTTCGTTG
AAACTTTAGCTAGAAGCATTTGCGAAAGCTTGAACAGTCTGGACTTCCGGTTGGGGGTAA
TGAAAAGAAGGCCAAACTGGCAAATGTTGTGAGAAAATGATGACTAATTCACAAGACACT
GAGCTTTCTTTCACAATCACTGGGACAACACTAAGTGGAATGAAAATCAAAACCCTCGAA
TGTTTTTGGCGATGATTACATATATCACAAAAAATCAACCTGAGTGGTTCAGAAACATCCTG
AGCATCGCACCAATAATGTTCTCAAACAAAATGGCAAGACTAGGAAAAGGATACATGTTCG
AGAGTAAGAGAATGAAGCTCCGAACACAAATACCCGCAGAAATGCTAGCAAGCATTGACCT
GAAGTATTTCAATGAATCAACAAGGAAGAAAATTGAGAAAATAAGGCCTCTTCTAATAGATG
GCACAGCATCATTGAGCCCTGGGATGATGATGGGCATGTTCAACATGCTAAGTACGGTTTT
AGGAGTCTCGGTACTGAATCTTGGGCAAAAGAAATACACCAAGACAACATACTGGTGGGAT
GGGCTCCAATCCTCCGACGATTTTGCCCTCATAGTGAATGCACCAAATCATGAGGGAATAC
AAGCAGGAGTGGATAGATTCTACAGGACCTGCAAGTTAGTGGGAATCAACATGAGCAAAAA
GAAGTCCTATATAAATAAAACAGGGACATTTGAATTCACAAGCTTTTTTATCGATATGGATT
TGTGGCTAATTTTAGCATGGAGCTTCCCAGTTTTGGAGTGTCTGGAATAAACGAGTCAGCT
GATATGAGTATTGGAGTAACAGTGATAAAGAACAACATGATAAACAATGACCTTGGGCCAG
CAACAGCCCAGATGGCTCTCCAATTGTTCATCAAAGACTACAGATATACATATAGGTGCCAT
AGAGGAGACACACAAATTCAGACGAGAAGATCATTCGAGCTAAAGAAGCTGTGGGATCAAA
CCCAATCAAGGGCAGGACTATTGGTATCAGATGGGGACCAAACTTATACAATATCCGGAA
CCTTCACATCCCTGAAGTCTGCTTAAAGTGGGAGCTAATGGATGAGAATTATCGGGGAAGA
CTTTGTAACCCCCTGAATCCCTTTGTCAGCCATAAAGAAATTGAGTCTGTAAACAATGCTGT
AGTGATGCCAGCCCACGGTCCAGCCAAAAGTATGGAATATGATGCCGTTGCAACTACACA
CTCCTGGAATCCCAAGAGGAACCGCTCTATTCTAAACACTAGCCAAAGGGGAATTCTTGAG
GATGAACAGATGTACCAAAAGTGCTGCAACTTGTTCGAGAAATTTTTCCCTAGTAGTTCATA
TAGGAGACCGATTGGAATTTCTAGCATGGTGGAGGCCATGGTGTCTAGGGCCCGGATTGA
TGCCAGAATTGACTTCGAGTCTGGACGGATTAAGAAGGAAGAGTTCTCTGAGATCATGAAG
ATCTGTTCCACCATTGAAGAACTCAGACGGCAAAAATAATGAATTTAGCTTGTCCTTCATGA
AAAAATGCCTTGTTTCTACT (SEQ ID NO: 20)

Influenza A virus (A/New York/392/2004(H3N2)) segment 3 (NCBI Ref Seq: NC_007371.1)
AGCAAAAGCAGGTACTGATTCGAAATGGAAGATTTTGTGCGACAATGCTTCAACCCGATGA
TTGTCGAACTTGCAGAAAAAGCAATGAAAGAGTATGGAGAGGATCTGAAAATTGAAACAAA
CAAATTTGCAGCAATATGCACCCACTTGGAGGTATGTTTCATGTATTCAGATTTTCATTTCAT
CAATGAACAAGGCGAATCAATAGTGGTAGAACTTGATGATCCAAATGCACTGTTAAAGCAC
AGATTTGAAATAATCGAGGGGAGAGACAGAACAATGGCCTGGACAGTAGTAAACAGTATCT
GCAACACTACTGGAGCAGAAAAACCAAAGTTTCTACCAGATTTGTATGATTACAAGGAGAAT
AGATTCATCGAAATTGGAGTGACAAGAAGAGAAGTCCACATATATTACCTTGAAAAGGCCA

FIG. 9 (cont'd)

ATAAAATTAAATCTGAGAACACACACATTCACATCTTCTCATTCACTGGGGAGGAAATAGCC
ACAAAGGCAGACTACACTCTCGACGAGGAAAGCAGGGCTAGGATTAAAACCAGGCTATTTA
CCATAAGACAAGAAATGGCCAACAGAGGCCTCTGGGATTCCTTTCGTCAGTCCGAAAGAG
GCGAAGAAACAATTGAAGAAAAATTTGAAATCTCAGGAACTATGCGTAGGCTTGCCGACCA
AAGTCTCCCACCGAATTCTCCTGCCTTGAGAATTTTAGAGCCTATGTGGATGGATTCGAA
CCGAACGGCTGCATTGAGGGCAAGCTTTCTCAAATGTCCAAAGAAGTGAATGCCAAAATTG
AACCTTTTCTGAAGACAACACCAAGACCAATCAAACTTCCTAATGGACCTCCTTGTTATCAG
CGGTCCAAATTCCTCCTGATGGATGCTTTGAAATTGAGCATTGAAGACCCAAGTCATGAAG
GAGAAGGGATTCCATTATATGATGCGATCAAGTGCATAAAACATTCTTTGGATGGAAAGAA
CCTTATATAGTCAAACCACACGAAAGGGAATAAATTCAAATTACCTGCTGTCATGGAAGCA
AGTATTGTCAGAATTGCAGGACATTGAAATGAGGAGAAGATCCCAAGGACTAAAACATG
AAGAAAACGAGTCAACTAAAGTGGGCTCTTGGTGAAAACATGGCACCAGAGAAGTAGACT
TTGACAACTGCAGAGACATAAGCGATTTGAAGCAATATGATAGTGACGAACCTGAATTAAG
GTCACTTTCAAGCTGGATACAGAATGAGTTCAACAAGGCCTGCGAGCTAACTGATTCAATC
TGGATAGAGCTCGATGAAATTGGAGAGGACGTAGCCCCAATTGAGTACATTGCAAGCATGA
GGAGGAATTATTTCACAGCAGAGGTGTCCCATTGTAGAGCCACTGAGTACATAATGAAGGG
GGTATACATTAATACTGCCCTGCTCAATGCATCCTGTGCAGCAATGGACGATTTTCAACTAA
TTCCCATGATAAGCAAGTGCAGAACTAAAGAGGGAAGGCGAAAAACCAATTTATATGGATT
CATCATAAAGGGAAGATCTCATTTAAGGAATGACACAGATGTGGTAAACTTTGTGAGCATG
GAGTTTTCTCTCACTGACCCGAGACTTGAGCCACATAAATGGGAGAAATACTGTGTCCTTG
AGATAGGAGATATGTTACTAAGAAGTGCCATAGGCCAAATTTCAAGGCCTATGTTCTTGTAT
GTGAGGACAAACGGAACATCAAGGTCAAAATGAAATGGGGAATGGAGATGAGACGTTGC
CTCCTTCAGTCACTCCAGCAGATCGAGAGCATGATTGAAGCCGAGTCCTCGATTAAAGAGA
AAGACATGACCAAAGAGTTTTTTGAGAATAAATCAGAAGCATGGCCCATTGGGGAGTCCCC
CAAGGGAGTGGAAGAAGGTTCCATTGGGAAAGTCTGTAGGACTCTATTGGCTAAGTCAGT
GTTCAATAGCCTGTATGCATCACCACAATTGGAAGGATTTTCAGCGGAGTCAAGAAACTG
CTTCTTGTTGTTCAGGCTCTTAGGGACAACCTCGAACCTGGGACCTTTGATCTCGGGGGG
CTATATGAAGCAATTGAGGAGTGCCTGATTAATGATCCCTGGGTTTTGCTCAATGCATCTTG
GTTCAACTCCTTCCTGACACATGCATTAAAATAGTTATGGCAGTGCTACTATTTGTTATCCG
TACTGTCCAAAAAGTACCTTGTTTCTACT (SEQ ID NO: 21)

Influenza A virus (A/New York/392/2004(H3N2)) segment 5 (NCBI Ref Seq: NC_007369.1)
AGCAAAAGCAGGGTTAATAATCACTCACCGAGTGACATCAAAATCATGGCGTCCCAAGGCA
CCAAACGGTCTTATGAACAGATGGAAACTGATGGGGATCGCCAGAATGCAACTGAGATTAG
GGCATCCGTCGGGAAGATGATTGATGGAATTGGGAGATTCTACATCCAAATGTGCACTGAA
CTTAAACTCAGTGATCATGAAGGCGGTTGATCCAGAACAGCTTGACAATAGAGAAATGG
TGCTCTCTGCTTTTGATGAAAGAAGGAATAAATACCTGGAAGAACACCCCAGCGCGGGAA
AGATCCCAAGAAACTGGGGGGCCCATATACAGGAGAGTAGATGGAAATGGATGAGGGA
ACTCGTCCTTTATGACAAAGAAGAGATAAGGCGAATCTGGCGCCAAGCCAACAATGGTGA
GGATGCGACAGCTGGTCTAACTCACATAATGATCTGGCATTCCAATTTGAATGATGCAACA
TACCAGAGGACAAGAGCTCTTGTTCGAACTGGAATGGATCCAGAATGTGCTCTCTGATGC
AGGGCTCGACTCTCCCTAGAAGGTCCGGAGCTGCAGGTGCTGCAGTCAAAGGAATCGGG
ACAATGGTGATGGAACTGATCAGAATGGTCAAACGGGGATCAACGATCGAAATTTCTGGA
GAGGTGAGAATGGGCGGAAACAAGAAGTGCTTATGAGAATGTGCAACATTCTTAAAG
GAAAATTTCAAACAGCTGCACAAGAGCAATGGTGGATCAAGTGAGAGAAGTCGGAACC
CAGGAAATGCTGAGATCGAAGATCTCATATTTTGGCAAGATCTGCATTGATATTGAGAGG
GTCAGTTGCTCACAAATCTTGCCTACCTGCCTGTGCGTATGGACCTGCAGTATCCAGTGGG
TACGACTTCGAAAAGAGGGATATTCCTTGGTGGGAATAGACCCTTTCAAACTACTTCAAAA
TAGCCAAATATACAGCCTAATCAGACCTAACGAGAATCCAGCACACAAGAGTCAGCTGGTG

FIG. 9 (cont'd)

TGGATGGCATGCCATTCTGCTGCATTTGAAGATTTAAGATTGTTAAGCTTCATCAGAGGGA
CAAAAGTATCTCCGCGGGGGAAACTGTCAACTAGAGGAGTACAAATTGCTTCAAATGAGAA
CATGGATAATATGGGATCGAGCACTCTTGAACTGAGAAGCGGGTACTGGGCCATAAGGAC
CAGGAGTGGAGGAAACACTAATCAACAGAGGGCCTCCGCAGGCCAAACCAGTGTGCAACC
TACGTTTTCTGTACAAAGAAACCTCCCATTTGAAAAGTCAACCATCATGGCAGCATTCACTG
GAAATACGGAGGGAAGGACTTCAGACATGAGGGCAGAAATCATAAGAATGATGGAAGGTG
CAAAACCAGAAGAAGTGTCATTCCGGGGGAGGGGAGTTTTCGAGCTCTCAGACGAGAAGG
CAACGAACCCGATCGTGCCCTCTTTTGATATGAGTAATGAAGGATCTTATTTCTTCGGAGAC
AATGCAGAAGAGTACGACAATTAAGGAAAAAATACCCTTGTTTCTACT (SEQ ID NO: 22)

Influenza A virus (A/New York/392/2004(H3N2)) segment 7 (NCBI Ref Seq: NC_007367.1)
AGCAAAAGCAGGTAGATATTGAAAGATGAGCCTTCTAACCGAGGTCGAAACGTATGTTCTC
TCTATCGTTCCATCAGGCCCCCTCAAAGCCGAGATCGCGCAGAGACTTGAAGATGTCTTTG
CTGGGAAAAACACAGATCTTGAGGCTCTCATGGAATGGCTAAAGACAAGACCAATTCTGTC
ACCTCTGACTAAGGGGATTTTGGGGTTTGTGTTCACGCTCACCGTGCCCAGTGAGCGAGG
ACTGCAGCGTAGACGCTTTGTCCAAAATGCCCTCAATGGGAATGGAGATCCAAATAACATG
GACAAAGCAGTTAAACTGTATAGGAAACTTAAGAGGGAGATAACGTTCCATGGGGCCAAAG
AAATAGCTCTCAGTTATTCTGCTGGTGCACTTGCCAGTTGCATGGGCCTCATATACAATAG
GATGGGGGCTGTAACCACTGAAGTGGCATTTGGCCTGGTATGTGCAACATGTGAACAGAT
TGCTGACTCCCAGCACAGGTCTCATAGGCAAATGGTGGCAACAACCAATCCATTAATAAAA
CATGAGAACAGAATGGTTTTGGCCAGCACTACAGCTAAGGCTATGGAGCAAATGGCTGGA
TCAAGTGAGCAGGCAGCGGAGGCCATGGAAATTGCTAGTCAGGCCAGGCAAATGGTGCA
GGCAATGAGAGCCGTTGGGACTCATCCTAGCTCCAGTACTGGTCTAAGAGATGATCTTCTT
GAAAATTTGCAGACCTATCAGAAACGAATGGGGGTGCAGATGCAACGATTCAAGTGACCC
GCTTGTTGTTGCCGCGAGTATCATTGGGATCTTGCACTTGATATTGTGGATTCTTGATCGTC
TTTTTTTCAAATGCGTCTATCGACTCTTCAAACACGGCCTTAAAAGAGGCCCTTCTACGGAA
GGAGTACCTGAGTCTATGAGGGAAGAATATCGAAAGGAACAGCAGAATGCTGTGGATGCT
GACGACAGTCATTTTGTCAGCATAGAGTTGGAGTAAAAAACTACCTTGTTTCTACT (SEQ ID
NO: 23)

Influenza A virus (A/New York/392/2004(H3N2)) segment 8 (NCBI Ref Seq: NC_007370.1)
AGCAAAAGCAGGGTGACAAAGACATAATGGATTCCAACACTGTGTCAAGTTTCCAGGTAGA
TTGCTTTCTTTGGCATATCCGGAAACAAGTTGTAGACCAAGAACTGAGTGATGCCCCATTC
CTTGATCGGCTTCGCCGAGATCAGAGGTCCCTAAGGGGAAGAGGCAATACTCTCGGTCTA
GACATCAAAGCAGCCACCCATGTTGGAAAGCAAATTGTAGAAAAGATTCTGAAAGAAGAAT
CTGATGAGGCACTTAAAATGACCATGGTCTCCACACCTGCTTCGCGATACATAACTGACAT
GACTATTGAGGAATTGTCAAGAAACTGGTTCATGCTAATGCCCAAGCAGAAAGTGGAAGGA
CCTCTTTGCATCAGAATGGACCAGGCAATCATGGAGAAAAACATCATGTTGAAAGCGAATT
TCAGTGTGATTTTTGACCGACTAGAGACCATAGTATTACTAAGGGCTTTCACCGAAGAGGG
AGCAATTGTTGGCGAAATCTCACCATTGCCTTCTTTTCCAGGACATACTATTGAGGATGTCA
AAAATGCAATTGGGGTCCTCATCGGAGGACTTGAATGGAATGATAACACAGTTCGAGTCTC
TAAAAATCTACAGAGATTCGCTTGGAGAAGCAGTAATGAGAATGGGGACCTCCACTTACT
CCAAAACAGAAACGGAAAATGGCGAGAACAGCTAGGTCAAAAGTTTGAAGAGATAAGATG
GCTGATTGAAGAAGTGAGACACAGACTAAAAACAACTGAAAATAGCTTTGAACAAATAACAT
TCATGCAAGCATTACAACTGCTGTTTGAAGTGGAACAGGAGATAAGAACTTTCTCATTTCAG
CTTATTTAATGATAAAAAACACCCTTGTTTCTACT (SEQ ID NO: 24)

FIG. 9 (cont'd)

Influenza A virus (A/Goose/Guangdong/1/96(H5N1)) polymerase (PB2) gene (NCBI Ref Seq: NC_007357.1)
AGCAAAAGCAGGTCAATTATATTCAATATGGAAAGAATAAAAGAACTAAGAGATCTAATGTC
GCAGTCCCGCACTCGCGAGATACTAACAAAAACCACTGTGGATCATATGGCCATAATCAAG
AAATACACATCAGGAAGACAAGAGAAGAACCCTGCTCTCAGAATGAAATGGATGATGGCAA
TGAAATATCCAATCACAGCAGACAAGAGAATAATGGAGATGATTCCTGAAAGGAATGAGCA
AGGACAAACGCTTTGGAGCAAGACAAATGATGCTGGGTCGGACAGAGTGATGGTGTCTCC
CCTAGCTGTAACTTGGTGGAACAGGAATGGGCCGACAACAAGTACAGTCCATTATCCAAAG
GTTTACAAAACATACTTTGAGAAGGTTGAAAGGTTAAAACATGGAACCTTCGGTCCCGTTCA
TTTCCGAAACCAAGTTAAAATACGTCGCCGGGTGGATATAAACCCGGCCATGCAGATCTC
AGTGCTAAAGAAGCACAAGATGTTATCATGGAGGTCGTTTCCCAAATGAAGTGGGAGCTA
GAATATTGACATCAGAGTCGCAATTGACAATAACAAAAGAGAAGAAAGAAGAGCTCCAGGA
TTGTAAAATTGCTCCTTTAATGGTGGCATACATGTTGGAAAGAGAACTGGTCCGCAAAACC
AGATTTCTACCGGTAGCAGGCGGAACAAGCAGTGTGTACATTGAGGTATTGCATTTGACTC
AAGGGACCTGTTGGGAACAGATGTACACTCCCGGCGGAGAAGTAAGAAATGATGATGTTG
ACCAGAGTTTGATCATCGCTGCCAGAAACATTGTTAGGAGAGCAACAGTATCAGCGGACCC
ACTGGCATCACTCTTGGAGATGTGTCACAGCACACAAATTGGGGAATAAGGATGGTGGA
CATCCTTAGGCAAAACCCAACTGAGGAGCAAGCTGTGGATATATGCAAAGCAGCAATGGG
TTTGAGGATCAGTTCATCCTTTAGCTTTGGAGGCTTCACTTTCAAAAGAACAAATGGATCAT
CCGTCAAGAAGGAAGAGGAAGTGCTTACAGGCAACCTCCAAACATTGAAAATAAAAGTACA
TGAGGGGTATGAAGAATTCACAATGGTTGGGCGGAGAGCAACAGCTATCCTGAGGAAAGC
AACTAGAAGGCTGATTCAGTTGATAGTAAGTGGAAGAGATGAACAATCAATCGCTGAAGCG
ATCATTGTAGCAATGGTGTTCTCACAGGAGGATTGCATGATAAAGGCAGTCCGAGGCGATC
TGAATTTCGTGAACAGAGCAAACCAAAGATTGAACCCCATGCATCAACTCCTGAGGCACTT
CCAAAAAGATGCAAAAGTGCTGTTTCAGAACTGGGGAATTGAACCTATTGACAATGTCATG
GGGATGATCGGAATATTACCTGACATGACTCCAAGCGCAGAGATGTCACTGAGAGGAGTG
AGAGTTAGTAAGATGGGAGTAGATGAATATTCCAGCACGGAGAGAGTGGTGGTGAGTATT
GACCGTTTCTTGAGGGTCCGAGATCAGCAGGGGAACGTACTCTTATCTCCTGAAGAGGTTA
GTGAAACACAGGGAACAGAGAAGTTGACAATAACATATTCATCCTCAATGATGTGGGAAAT
CAACGGTCCTGAGTCAGTGCTTGTTAACACTTATCAATGGATCATCAGGAATTGGGAGACT
GTAAAGATTCAATGGTCTCAAGATCCCACAATGCTGTACAATAAGATGGAGTTTGAATCGTT
CCAATCCTTGGTGCCAAAGGCTGCCAGAAGCCAATATAGTGGATTTGTGAGAACACTATTC
CAACAGATGCGTGATGTTTGGGGACATTTGATACTGTCCAAATAATCAAGCTGCTACCATT
TGCAGCAGCCCCACCGGAGCCGAGCAGAATGCAGTTTTCTTCTAACTGTGAATGTGAG
AGGCTCAGGAATGAGAATACTCGTGAGGGGTAACTCCCCGTGTTCAACTACAACAAGGC
AACCAAAAGGCTTACAGTCCTCGGAAAGGACGCAGGTGCATTAACAGAAGATCCAGACGA
GGGAACAGCCGGGGTGGAATCTGCAGTATTGAGGGGATTCCTAATTCTAGGCAGAGAGGA
CAAAAGATATGGACCCGCATTGAGCATCAATGAACTGAGCAATCTTGCAAAAGGGGAGAAG
GCTAATGTATTGATAATGCAAGGAGACGTGGTGTTGGTAATGAAACGGAAACGGGACTTTA
GCATACTTACTGACAGCCAGACAGCGACCAAAAGAATTCGGATGGCCATCAATTAGTGTTG
AATAGTTTAAAAACGACCTTGTTTCTACT (SEQ ID NO: 25)

Influenza A virus (A/goose/Guangdong/1/1996(H5N1)) polymerase (PB1) and PB1-F2 protein (PB1-F2) genes (NCBI Ref Seq: NC_007358.1)
AGCAAAAGCAGGCAAACCATTTGAATGGATGTCAATCCGACTTTACTTTTCTTAAAAGTGCC
AGCGCAAAATGCTATAAGTACCACATTCCCTTATACTGGAGATCCTCCATACAGCC<u>ATGGA</u>
<u>ACAGGAACAGGATACACCATGGACACAGTCAACAGAACACATCAATATTCAGAAAGGGGA</u>
<u>AATGGACAACGAACACAGAGACTGGAGCACCCAACTCAATCCGATTGATGGACCACTAC</u>
<u>CTGAGGATAATGAGCCGAGTGGGTATGCACAAACAGATTGTGTATTGGAAGCAATGGCTTT</u>

FIG. 9 (cont'd)

CCTTGAAGAATCCCACCCAGGGATCTTTGAAAACTCGTGTCTTGAAACGATGGAAGTTGTT
CAGCAAACAAGAGTGGATAAGCTGACCCAAGGTCGCCAAACCTATGACTGGACATTGAAAA
GAAACCAGCCGGCTGCAACCGCTTTGGCCAACACTATAGAGGTCTTCAGATCGAATGGTC
TAACAGCCAATGAATCGGGAAGGCTAATAGATTTCCTCAAAGACGTGATGGAATCAATGGA
TAAGGGAGAAATGGAAATAATAACACATTTCCAGAGAAAGAGAAGAGTGAGGGACAACATG
ACCAAGAAATGGTCACACAAGAACAATAGGGAAGAAAAACAAAGGCTGAACAAAAGGA
GCTACCTAATAAGAGCACTGACACTGAACACAATGACAAAAGACGCAGAAAGAGGCAAATT
GAAGAGGCGGGCAATTGCAACACCCGGGATGCAAATCAGAGGATTCGTGTACTTTGTCGA
AACACTAGCGAGGAGTATCTGTGAGAAACTTGAGCAATCTGGACTCCCCGTCGGAGGGAA
TGAAAAGAAGGCTAAATTGGCAAATGTCGTGAGGAAGATGATGACTAACTCACAAGATACA
GAGCTCTCTTTTACAATTACTGGAGACAACACCAAATGGAATGAGAATCAGAACCCTCGGA
TGTTTCTAGCAATGATAACATACATCACAAGGAACCAACCTGAATGGTTTAGAAATGTCTTA
AGCATTGCTCCTATAATGTTCTCAAACAAGATGGCAAGATTAGGGAAAGGATACATGTTCG
AAAGTAAGAGCATGAAGCTACGGACACAAATACCAGCAGAAATGCTTGCAAGCATTGACTT
GAAATACTTCAACGAATCAACGAGAAAGAAAATCGAGAAAATAAGACCTCTACTAATAGATG
GCACAGCCTCATTGAGTCCTGGAATGATGATGGGCATGTTCAATATGCTGAGTACAGTCTT
AGGAGTTTCAATCCTGAATCTTGGGCAGAAGAGGTACACCAAAACCACATACTGGTGGGAC
GGACTCCAATCCTCTGATGATTTCGCTCTCATAGTGAATGCACCAAATCATGAGGGAATAG
AAGCAGGGGTGGATAGGTTCTATAGGACTTGCAAACTAGTTGGAATCAATATGACCAAGAA
GAAGTCTTACATAAATCGGACAGGAACATGTGAATTCACAAGCTTCTTCTACCGCTATGGG
TTCGTAGCCAACTTCAGTATGGAGCTGCCCAGCTTTGGAGTGTCTGGGATTAATGAATCGG
CTGACATGAGCATTGGTGTTACAGTGATAAAGAACAATATGATGGACAACGACCTTGGACC
AGCAACAGCTCAGATGGCTCTTCAGCTATTCATTAAGGACTACAGATACCCATACCGATGC
CACAGGGGGGATACACAAATCCAAACGAGGAGATCATTCGAGCTGAAGAAGCTGTGGGAG
CAGACCCGCTCAAAGGCAGGACTGTTGGTTTCAGATGGAGGACCAAACCCATACAATATC
CGGAATCTCCACATTCCGGAGGCTGGCTTGAAGTGGGAATTGATGGATGAAGACTACCAG
GGCAGACTGTGTAATCCTCTGAACCCGTTTGTTAGTCATAAGGAAATTGAGTCTGTCAACA
ATGCTGTGGTAATGCCAGCTCATGGCCCAGCCAAGAGCATGGAATATGATGCAGTTGCGA
CTACACATTCATGGATTCCCAAGAGGAATCGTTCCATTCTCAACACCAGCCAAAGGGGGAT
TCTTGAGGATGAACAGATGTATCAGAAGTGCTGCAATCTATTCGAGAAATTCTTCCCTAGCA
GTTCATATCGGAGGCCAGTTGGAATTTCCAGCATGGTGGAGGCCATGGTGTCTAGGGCCC
GAATTGATGCACGAATTGACTTCGAGTCTGGAAGGATTAAGAAAGAAGAGTTTGCTGAGAT
CATGAAGATCTGTTCCACCATTGAAGAGCTCGGACGGCAAAAATAGTGAATTTAGCTTGTC
CTTCATGAAAAAATGCCTTGTTTCTACT (SEQ ID NO: 26)

Influenza A virus (A/goose/Guangdong/1/1996(H5N1)) polymerase (PA) and PA-X protein (PA-X) genes (NCBI Ref Seq: NC_007359.1)
AGCAAAAGCAGGTACTGATCCAAAATGGAAGACTTTGTGCGACAATGCTTCAATCCAATGA
TTGTCGAGCTTGCGGAAAAGGCAATGAAAGAATATGGGGAAGATCCGAAAATCGAAACGA
ACAAATTTGCCGCAATATGCACGCACTTAGAAGTCTGTTTCATGTATTCAGATTTCCACTTT
ATTGATGAACGGGGCGAATCAACAATTATAGAATCTGGCGATCCAATGCATTATTGAAAC
ACCGGTTTGAAATAATCGAAGGGAGGGACCGAACAATGGCCTGGACAGTGGTAATAGTA
TCTGCAACACCACAGGAGTTGAGAAGCCTAAATTTCTCCCAGATTTGTATGACTACAAGGA
GAACCGATTTATTGAAATTGGAGTGACACGGAGGGAAGTTCACACATACTATCTAGAAAAA
GCCAACAAGATAAAATCTGAGAAGACACACATTCACATATTCTCATTCACTGGAGAGGAAAT
GGCCACCAAAGCGGACTACACCCTTGATGAAGAAGCAGGGCCCGAATCAAAACCAGGCT
GTTCACTATAAGGCAGGAAATGGCCAGTAGGGGTTTATGGGATTCCTTTCGTCAGTCCGAG
AGAGGCGAAGAGACAGTTGAAGAAAGATTTGAAATCACAGGGACTATGTGCAGGCTTGCC
GACCAAAGTCTCCCACCTAATTTCTCCAGCCTTGAAAAATTTAGAGCCTATGTGGATGGATT

FIG. 9 (cont'd)

CGAACCGAACGGCTGCATTGAGGGCAAGCTTTCTCAAATGTCGAAAGAAGTAAACGCCAG
AATTGAGCCATTTCTGAAGACAACACCACGCCCTCTTAGATTACCTGATGGGCCTCCCTGC
TCTCAGCGGTCGAAGTTTTGCTGATGGATGCCCTTAAATTAAGCATCGAAGACCCGAGTC
ATGAGGGGAGGGGATACCGCTATATGATGCAATCAAATGCATGAAAACATTTTCGGCTG
GAAAGAGCCCAACATTGTAAAACCACATGAAAAGGCATAAACCCCAATTACCTCCTGGCT
TGGAAGCAGGTGCTGGCAGAGCTCCAAGATATTGAAAACGAGGAGAAAATTCCAAAGACA
AAGAACATGAGGAAAACAAGCCAATTGAAGTGGGCACTTGGTGAGAATATGGCACCAGAG
AAAGTAGACTTTGAGGATTGCAAAGATGTTAGCGATCTAAGGCAGTATGACAGTGATGAAC
CAAAGCCTAGATCACTAGCAAGCTGGATCCAGAGTGAATTCAACAAGGCATGCGAATTGAC
AGATTCAAGTTGGATTGAACTTGATGAAATAGGGGAAGACGTTGCTCCAATTGAGCACATT
GCAAGTATGAGAAGGAACTATTTCACAGCGGAAGTATCCCATTGCAGGGCTACTGAATACA
TAATGAAGGGAGTGTACATAAACACAGCTTTGTTAATGCATCCTGTGCAGCCATGGATGA
CTTCCAACTGATCCCAATGATAAGCAAATGCAGAACCAAAGAAGGAAGACGGAAAACTAAC
CTGTATGGATTCCTTATAAAAGGAAGATCCCATTTGAGAAATGACACCGATGTGGTAAACTT
TGTGAGTATGGAATTCTCTCTTACTGATCCGAGGCTGGAGCCACACAGATGGGAAAAGTAC
TGCGTTCTTCGGATAGGAGACATGCTCTTACGGACTGAAATAGGCCAAGTGTCAAGGCCC
ATGTTTCTTTATGTGAGAACCAATGGAACCTCCAAGATCAAGATGAAATGGGGCATGGAAA
TGAGGCGATGCCCTTTTCAATCCCTTCAACAGATTGAGAGCATGATTGAGGCCGAGTCTTC
TGTCAAAGAAAAGACATGACTAAAGAATTCTTTGAAAACAAATCAGAAACATGGCCAATTG
GAGAATCACCCAAGGGAGTGGAGGAAGGCTCCATCGGGAAGGTGTGCAGAACCTTACTG
GCTAAATCTGTTTTCAACAGTCTATATGCATCTCCACAACTCGAGGGGTTTTCAGCTGAATC
AAGAAAATTGCTTCTCATTGTTCAGGCACTTAGGGACAACCTGGAACCTGGAACCTTCGAT
CTTGGGGGGCTATATGAAGCAATTGAGGAGTGCCTGATTAATGATCCCTGGGTTTTGCTTA
ATGCATCTTGGTTCAACTCCTTCCTCACACATGCACTAAGATAGTTGTGGCAATGCTACTAT
TTGCTATCCATACTGTCCAAAAAAGTACCTTGTTTCTACT (SEQ ID NO: 27)

Influenza A virus (A/Goose/Guangdong/1/96(H5N1)) nucleocapsid protein (NP) gene (NCBI Ref Seq: NC_007360.1)
AGCAAAAGCAGGGTAGATAATCACTCACTGAGTGACATCAACATCATGGCGTCTCAGGGCA
CCAAACGATCTTATGAACAGATGGAAACTGGTGGAGAACGCCAGAATGCTACTGAGATCAG
AGCATCTGTTGGAAGAATGGTTGGTGGAATTGGGAGGTTTTATATACAGATGTGCACTGAA
CTCAAACTCAGCGACTATGAAGGAAGGCTGATTCAGAACAGCATAACAATAGAGAGAATGG
TTCTCTCTGCATTTGATGAAAGGAGGAACAAATACCTGGAAGAACATCCCAGTGCGGGGAA
GGACCCAAAGAAAACTGGAGGTCCAATCTACCGAAGAAGAGACGGAAAATGGGTGAGAGA
GCTGATTCTGTATGACAAAGAGGAGATCAGGAGAATTTGGCGTCAAGCGAACAATGGAGA
AGATGCAACTGCTGGTCTCACTCACATGATGATCTGGCATTCCAATCTAAATGATGCCACAT
ACCAGAGAACAAGAGCTCTCGTGCGTACTGGGATGGACCCTAGAATGTGCTCTCTGATGC
AAGGATCAACTCTCCCGAGGAGATCTGGAGCTGCTGGTGCGGCAGTAAAGGGAGTCGGA
ACGATGGTGATGGAACTAATTCGGATGATAAAGCGAGGGATTAACGATCGGAATTTCTGGA
GAGGTGAAAATGGGCGAAGAACAAGAATTGCATATGAGAGAATGTGCAACATCCTCAAAG
GGAAATTCCAAACAGCAGCACAAAGAGCAATGATGGATCAGGTACGGGAAGCAGAAATC
CTGGGAATGCTGAGATTGAAGATCTCATATTTCTGGCACGGTCTGCACTCATCCTGAGAGG
ATCAGTGGCCCACAAGTCCTGCTTGCCTGCTTGTGTGTACGGCTTGCCGTGGCCAGTGG
ATATGACTTTGAGAGAGAAGGGTACTCTCTGGTCGGGATTGATCCTTTCCGTCTGCTGCAA
AACAGCCAGGTCTTTAGTCTAATTAGACCAAATGAGAATCCAGCACATAAAGTCAATTGGT
GTGGATGGCATGCCATTCTGCAGCATTTGAAGATCTGAGAGTCTCAAGCTTCATCAGAGGG
ACAAGAGTGGCCCCAAGGGGACAACTATCTACTAGAGGAGTTCAAATTGCTTCAAATGAGA
ACATGGAAACAATGGACTCCAGCACTCTTGAACTGAGAAGCAGATATTGGGCTATAAGGAC
CAGGAGTGGAGGAAACACCAACCAGCAGAGAGCATCTGCAGGACAAATCAGTGTGCAGCC

FIG. 9 (cont'd)

TACTTTCTCGGTACAGAGAAATCTTCCCTTCGAAAGAGCGACCATTATGGCGGCATTCACA
GGGAATACAGAGGGCAGAACATCTGACATGAGGACTGAAATCATAAGGATGATGGAAAGC
TCCAGACCAGAAGATGTGTCTTTCCAGGGGCGGGGAGTCTTCGAGCTCTCGGACGAAAAG
GCAACGAACCCGATCGTGCCTTCCTTTGACATGAGTAATGAAGGATCTTATTTCTTCGGAG
ACAATGCAGAGGAATATGACAATTGAAGAAAATACCCTTGTTTCTACT (SEQ ID NO: 28

Influenza A virus (A/goose/Guangdong/1/1996(H5N1)) segment 7 (NCBI Ref Seq: NC_007363.1)
AGCAAAAGCAGGTAGATATTGAAAAATGAGTCTTCTAACCGAGGTCGAAACGTACGTTCTC
TCTATCGTCCCGTCAGGCCCCCTCAAAGCCGAGATCGCGCAGAGACTTGAGGATGTCTTT
GCAGGAAAGAACACCGATCTCGAGGCTCTCATGGAATGGCTAAAGACAAGACCAATCCTG
TCACCTCTGACTAAAGGGATTTTAGGATTTGTGTTCACGCTCACCGTGCCCAGTGAGCGAG
GACTGCAGCGTAGACGCTTTGTCCAGAATGCCTTAAATGGAAATGGAGATCCAAACAATAT
GGATAGGGCAGTTAAGCTATACAAGAAGCTGAAAAGAGAAATAACATTCCATGGGGCTAAG
GAGGTCGCACTCAGCTACTCAACCGGTGCACTTGCCAGTTGTATGGGTCTCATATACAACA
GGATGGGAACGGTGACCACAGAAGTGGCTTTTGGCCTAGTGTGTGCCACTTGTGAGCAGA
TTGCAGATTCACAGCATCGGTCTCACAGACAGATGGCAACTACCACCAACCCACTAATCAG
GCATGAGAACAGAATGGTGCTGGCCAGCACTACAGCTAAGGCTATGGAGCAGATGGCTGG
ATCGAGTGAGCAGGCAGCGGAAGCCATGGAGGTTGCTAGTCAGGCTAGGCAGATGGTGC
AGGCAATGAGGACAATTGGGACTCATCCTAGCTCCAGTGCCGGTCTGAAAGATAATCTTCT
TGAAAATTTGCAGGCCTACCAAAACGAATGGGAGTGCAAATGCAGCGATTCAAGTGATCC
TCTTGTTGTTGCCGCAAGTATCATTGGGATACTGCACTTGATATTGTGGATTCTTGATCGTC
TTTTCTTCAAATGCATTTATCGTCGCCTTAAATACGGTTTGAAAAGAGGGCCTTCTACGGAA
GGGGTACCTGAGTCTATGAGGGAAGAGTATCGGCAGGAACAGCAGAGTGCTGTGGATGTT
GACGATGGTCATTTTGTCAACATAGAGCTGGAGTAAAAAACTACCTTGTTTCTACT (SEQ ID NO: 29)

Influenza A virus (A/goose/Guangdong/1/1996(H5N1)) segment 8 (NCBI Ref Seq: NC_007364.1)
GTGACAAAGACATAATGGATTCCAACACGATAACCTCGTTTCAGGTAGATTGTTATCTATGG
CACATAAGAAAGCTACTCAGTATGAGAGACATGTGTGATGCCCCTTTGATGACAGGCTCC
GAAGAGACCAAAAGGCATTAAAGGGAAGAGGCAGCACACTTGGACTCGATTTAAGAGTGG
CTACAATGGAGGGGAAAAAGATCGTTGAGGACATCCTGAAGAGTGAGACAAATGAAAACCT
CAAAATAGCCATTGCTTCCAGTCCTGCTCCTCGGTATATCACCGATATGAGCATAGAGGAG
ATGAGCCGAGAATGGTACATGCTGATGCCTAGGCAGAAAATAACTGGAGGCCTTATGGTG
AAAATGGACCAAGCCATAATGGATAAAGAATTATCCTTAAAGCAAATTTCTCAGTTCTATTT
GATCAACTAGAGACATTAGTCTCTCTGAGGGCATTCACAGAAAGTGGTGCTATTGTGGCTG
AAATATTTCCCATTCCCTCCGTACCAGGACATTTTACAGAGGATGTCAAAAATGCAATTGGA
ATCCTCATCGGTGGACTTGAATGGAATGATAACTCAATTCGAGCGTCTGAAAATATACAGA
GATTCGCTTGGGGAATCCATGATGAGAATGGGGGACCTTCACTCCTCCAAAACAGAAAC
GCTACATGGCGAAACGAGTTGAGTCAGAAGTTTGAAGAGATCAGATGGCTCATTGCTGAAT
GTAGAAATATACTGACAAAGACTGAAAATAGCTTTGAACAGATAACATTTTGCAAGCATTG
CAACTCTTACTTGAAGTTGAGAGTGAGATAAGGACCTTCTCTTTTCAGCTTATTTAATACTAA
AAAACAC (SEQ ID NO: 30)

Influenza B virus RNA 1 (NCBI Ref Seq: NC_002204.1)
AGCAGAAGCGGAGCTTTAAGATGAATATAAATCCATATTTTCTTTTCATAGATGTACCTATAC
AGGCAGCAATTTCAACAACATTCCCATACACCGGTGTTCCCCCTTATTCTCATGGAACGGG
AACAGGCTACACAATAGACACCGTGATTAGAACACACGAGTACTCAAACAAGGGAAAACAA

FIG. 9 (cont'd)

TACATTTCTGATGTTACAGGATGTGTAATGGTAGATCCAACAAATGGGCCATTACCCGAAG
ACAATGAACCGAGTGCCTATGCACAATTGGATTGTGTTCTGGAGGCTTTGGATAGAATGGA
TGAAGAACATCCAGGTCTGTTTCAAGCAGGGTCACAGAATGCCATGGAGGCACTAATGGT
CACAACAGTGGACAAATTGACTCAGGGGAGACAGACCTTTGATTGGACGGTGTGTAGAAA
CCAACCTGCTGCAACGGCACTGAACACAACAATAACCTCTTTTAGGTTGAATGATTTAAATG
GAGCCGACAAGGGTGGATTAGTGCCCTTTTGCCAAGATATCATTGATTCATTAGACAAACC
TGAAATGATTTTCTTCACAGTAAAGAATATAAAGAAAAAATTGCCTGCTAAAAACAGAAGG
GTTTCCTTATAAAAGAATACCTATGAAGGTAAAAGACAGAATAACAAGAGTGGAATACATC
AAAAGAGCATTATCATTAAACACAATGACTAAAGATGCTGAAAGAGGCAAACTAAAAGAAG
AGCAATTGCCACCGCTGGGATACAAATCAGAGGATTTGTATTAGTAGTTGAAAACTTGGCT
AAAAATATCTGTGAAATCTAGAGCAAAGTGGTTTACCCGTAGGTGGAAACGAAAGAAGG
CCAAACTATCAAATGCAGTGGCTAAAATGCTCAGTAATTGTCCACCAGGAGGGATCAGTAT
GACTGTGACAGGAGACAATACTAAATGGAATGAATGCTTAAATCCAAGAATCTTTTGGCTA
TGACTGAAAGAATAACCAGAGACAGCCCAATTTGGTTCCGGGATTTTGTAGTATAGCACC
GGTCTTGTTCTCCAATAAAATAGCTAGATTGGGAAAAGGGTTCATGATAACAAGTAAAACAA
AAAGACTAAAAGCTCAAATACCTTGTCCCGATCTGTTTAATATACCATTAGAAAGATATAATG
AAGAAACAAGGGCAAAACTGAAAAAGCTAAAACCTTTCTTCAATGAAGAAGGAACGGCATC
TCTTTCGCCAGGAATGATGATGGGAATGTTTAATATGCTATCTACAGTATTAGGAGTAGCCG
CACTAGGGATAAAAAACATTGGAAACAAAGAATACTTATGGGATGGACTGCAGTCTTCGGA
TGATTTTGCTCTGTTTGTTAATGCAAAAGATGAAGAGACATGTATGGAAGGAATAAACGATT
TTTACCGAACATGTAAGCTATTGGGAATAAACATGAGCAAAAGAAAAGTTACTGTAATGAA
ACTGGGATGTTTGAATTTACCAGCATGTTTTACAGAGATGGATTTGTATCTAATTTTGCAAT
GGAACTCCCTTCATTTGGAGTCGCTGGAGTGAATGAATCAGCAGACATGGCAATAGGAATG
ACAATAATAAAGAACAATATGATCAACAATGGGATGGGCCCAGCAACGGCACAAACAGCCA
TACAATTATCATAGCTGACTATAGATACACCTACAAATGCCACAGGGGAGATTCCAAAGTG
GAAGGGAAGAGAATGAAAATTATAAAGGAGCTATGGAAAACACTAAAGGAAGAGATGGTC
TATTAGTAGCAGATGGTGGGCCTAATCTTTACAATTTGAGAAACCTGCATATTCCAGAAATA
ATATTAAAATACAACATAATGGACCCTGAGTACAAAGGACGGTTACTGCATCCTCAAAATCC
CTTTGTAGGACATTTGTCTATTGAGGGTATCAAAGAAGCAGATATAACACCTGCACATGGC
CCAATAAAGAAAATGGACTACGATGCGGTATCTGGAACTCATAGTTGGAGAACCAAAAGGA
ACAGATCTATACTAAACACTGATCAGAGGAACATGATTCTTGAGGAACAATGCTACGCTAA
GTGTTGCAACCTTTTTGAGGCTTGCTTTAACAGTGCGTCATACAGGAAACCAGTAGGCCAG
CACAGCATGCTTGAAGCTATGGCCCACAGATTAAGAATGGATGCACGACTGGACTATGAGT
CAGGAAGGATGTCAAAAGAGGATTTCGAAAAAGCAATGGCTCACCTTGGTGAGATTGGGTA
CATGTAAGCTCCGGAAATGTCTATGGGGTTATTGGTCATCGTTGAATACATGCGGTGCACA
AATGATTAAAATGAAAAAAGGCTCGTGTTTCTACT (SEQ ID NO:31)

Influenza B virus (B/Lee/1940) segment 2 (NCBI Ref Seq: NC_002205.1)
ATGACGTTGGCTAAAATTGAACTACTAAAGCAGCTGTTAAGGGACAATGAAGCCAAAACGG
TGTTGAGACAGACAACGGTAGACCAATACAACATAATAAGAAAATTCAATACATCAAGAATT
GAAAAGAACCCTTCATTAAGAATGAAGTGGGCCATGTGTTCCAATTTTCCCTTAGCTCTGAC
CAAGGGTGATATGGCAAATCGAATCCCCTTGGAATACAAGGGAATACAACTTAAAACAAAT
GCTGAAGACATAGGAACTAAGGACAAATGTGTTCAATAGCAGCAGTTACCTGGTGGAATA
CATATGGGCCCATAGGGGATACTGAAGGGTTTGAAAAGGTCTACGAAGCTTTTTTCTCAG
AAAGATGAGACTTGACAATGCCACTTGGGGCCGAATAACCTTTGGCCCTGTTGAGAGAGTA
AGAAAAAGAGTACTACTAAACCCGCTCACCAAGGAAATGCCCCAGATGAAGCGAGCAAT
GTAATAATGGAAATATTATTCCCTAAAGAAGCAGGAATACCAAGAGAATCTACTTGGATACA
TAGAGAACTGATAAAAGAAAAAGAGAAAATTGAAGGGACGATGATAACTCCCATTGTA
CTGGCATACATGCTTGAGAGAGAACTAGTTGCCCGAAGAAGGTTCCTGCCAGTAGCAGGA

FIG. 9 (cont'd)

GCAACATCAGCAGAGTTCATAGAAATGCTACATTGCTTACAAGGTGAAAATTGGAGACAAA
TATATCATCCAGGAGGGAATAAACTAACTGAATCTAGATCTCAATCAATGATTGTAGCTTGC
AGGAAGATAATCAGAAGATCAATAGTTGCATCAAACCCACTAGAGCTAGCTGTAGAGATTG
CAAATAAGACTGTGATAGACACTGAACCTTTAAAATCATGTCTGGCAGCCCTGGATGGAGG
TGATGTAGCCTGTGACATAATAAGAGCTGCATTAGGATTAAAAATTAGACAAAGACAAAGAT
TTGGGAGACTTGAACTAAAGAGAATATCAGGAAGAGGATTCAAAAATGATGAAGAGATATT
AATCGGAAACGGAACAATACAAAAGATTGGAATATGGGACGGAGAAGAGGAATTCCATGTA
AGATGTGGCGAATGCAGGGGGATATTGAAAAAAGCCAAATGAGAATGGAAAAACTACTGA
TAAATTCAGCCAAAAGGAGGACATGAAAGATTTAATAATCTTATGCATGGTATTTCTCAA
GACACTAGGATGTTCCAAGGAGTGAGAGGAGAGATAAATTTCTTAATCGAGCAGGCCAAC
TTTTATCCCCATGTACCAACTCCAACGATACTTTCTGAATAGGAGCAATGACCTTTTGAT
CAATGGGGATATGAGGAATCACCTAAAGCAAGTGAGCTACATGGGATAAATGAATTAATGA
ATGCATCTGACTATACATTGAAAGGGGTTGTAGTAACAAAAATGTGATTGATGATTTAGT
TCTACTGAAACAGAAAAGTATCTATAACAAAAATCTTAGTTTAATAAAAAGGACTGGGGA
AGTTATAATGGGAGCCAATGACGTAAGTGAATTAGAATCACAAGCACAGCTAATGATAACG
TATGATACACCCAAGATGTGGGAAATGGGAACAACCAAAGAACTGGTACAAAACACTTACC
AATGGGTGCTTAAAAATTTAGTAACATTGAAGGCTCAGTTTCTTTGGGAAAAGAAGACATG
TTCCAATGGGATGCATTTGAAGCATTTGAAAGCATAATCCCTCAGAAGATGGCTGGTCAGT
ACAGTGGATTTGCAAGAGCAGTGCTCAAACAAATGAGAGACCAAGAGGTTATGAAAACTGA
CCAATTCATAAAATTGTTGCCTTTCTGTTTTTCGCCACCAAAATTAAGGAGCAATGGAGAGC
CTTATCAATTTTTGAGGCTTATGCTGAAAGGAGGAGGGGAAAATTTCATCGAAGTAAGGAA
AGGGTCCCCCTTGTTCTCCTACAATCCACAAACGGAAATCCTAACTATATGCGGCAGAATG
ATGTCATTAAAAGGAAAAATTGAGGATGAAGAAAGAAATAGATCAATGGGGAATGCAGTAC
TGGCAGGCTTTCTTGTTAGTGGCAAATATGACCCTGATCTTGGAGATTTCAAAACCATTGAG
GAACTTGAAAGACTAAAACCGGGAGAAAAAGCCAACATCTTACTTTACCAAGGAAAGCCCG
TTAAAGTAGTTAAAAGGAAAAGATATAGTGCTTTATCCAATGATATTTCACAAGGGATTAAG
AGACAAAGAATGACAGTTGAGTCCATGGGGTGGGCCTTGAGCTAA (SEQ ID NO:32)

Influenza B virus (B/Lee/1940) segment 3 (NCBI Ref Seq: NC_002206.1)
ATGGATACTTTTATTACAAAGAATTTCCAGACTACAATAATACAAAAGGCCAAAAACACAAT
GGCAGAATTTAGTGAAGATCCTGAATTACAGCCAGCAGTACTATTCAACATCTGCGTCCAT
CTGGAGGTCTGCTATGTAATAAGTGATATGAACTTTCTTGATGAGGAAGGAAAGACATATAC
AGCATTAGAAGGACAAGGAAAAGAGCAAAATTTGAGACCACAGTATGAAGTGATTGAGGGA
ATGCCAAGAAACATAGCATGGATGGTTCAAAGATCCTTAGCCCAAGAGCATGGAATAGAGA
CTCCAAGGTATCTGGCTGATTTATTTGATTATAAAACCAAGAGGTTTATCGAAGTCGGAATA
ACAAAGGGATTGGCTGATGATTACTTTTGGAAAAGAAAGAAAAGTTGGGGAATAGCATGG
AACTGATGATATTCAGCTACAATCAAGACTACTCGTTAAGTGATGAATCTTCATTGGATGAG
GAAGGAAAAGGGAGAGTGCTAAGCAGACTCACAGAACTTCAGGCTGAGTTAAGTTTGAAAA
ACCTATGGCAAGTTCTAATAGGGGAAGAAGAAATTGAAAAAGGAATTGACTTCAAACTTGG
ACAAACAATATCTAAACTGAGGAATATATCTGTTCCAGCTGGTTTCTCCAATTTTGAAGGGA
TGAGAAGTTACATAGACAACATAGACCCTAAGGAGCAATAGAGAGAAATCTAGCAAGGAT
GTCTCCCTTAGTATCAGTTACACCCAAAAAGTTGAAATGGGAGGACCTGAGACCCATAGGG
CCTCACATTTACAACCATGAGCTACCAGAAGTTCCATATAATGCCTTTCTCCTCATGTCTGA
TGAGTTGGGGCTGGCCAATATGACTGAAGGAAAGTCCAAGAAACCGAAGACCTTAGCTAA
GGAATGTCTAGAAAGGTATTCAACACTACGTGATCAAACTGACCCAATATTGATAATGAAAA
GCGAAAAAGCTAACGAAAACTTCTTATGGAGGTTATGGAGGGACTGTGTAAATACAATAAG
CAATGAGGAAACAGGCAACGAATTACAGAAAACCAATTATGCCAAGTGGGCCACAGGAGA
TGGACTAACATACCAAAAAATAATGAAAGAAGTAGCAATAGATGACGAAACGATGTACCAA
GAAGAACCCAAAATACCCAATAAATGTAGAGTGGCTGCTTGGGTTCAGGCAGAGATGAATC

FIG. 9 (cont'd)

TACTGAGTACTCTGACAAGTAAAAGGGCCCTGGATCTGCCAGAAATAGGGCCAGATGTAG
CACCCGTGGAGCATGTAGGGAGTGAAAGAAGGAAATACTTTGTTAATGAAATCAACTACTG
TAAAGCCTCTACAGTTATGATGAAGTATGTACTTTTTCACACTTCATTATTAAATGAAAGCAA
TGCTAGTATGGGAAAATATAAAGTAATACCAATCACCAACAGAGTGGTAAATGAAAAAGGG
GAAAGCTTTGACATGCTTTATGGTCTGGCGGTTAAGGGGCAATCTCATTTGCGGGGGGAC
ACGGATGTTGTAACAGTTGTGACTTTCGAGTTTAGTAGTACAGATCCTAGAGTGGACTCAG
GAAAGTGGCCAAAATATACTGTCTTTAAAATTGGCTCCCTATTTGTGAGTGGAAGAGAAAAA
CCTGTGTACCTATATTGCCGAGTGAATGGTACAAACAAAATCCAAATGAAATGGGGAATGG
AAGCTAGAAGATGTCTGCTTCAATCAATGCAACAAATGGAGGCAATTGTTGATCAAGAATCA
TCGATACAAGGGTATGATATGACCAAAGCTTGTTTCAAGGGAGACAGAGTGAATAATCCCA
AAACTTTCAGTATTGGGACTCAGGAAGGCAAACTAGTAAAAGGGTCCTTTGGGAAAGCACT
AAGAGTAATATTCACCAAATGTTTGATGCATTATGTATTTGGAAATGCTCAATTGGAGGGGT
TTAGTGCCGAATCTAGGAGACTTCTACTGTTAATTCAGGCATTAAAAGACAGGAAGGGCCC
TTGGGTATTTGACTTGGAGGGAATGTACTTTGGAGTAGAGGAATGTATTAGTAACAATCCTT
GGGTAATACAGAGTGCATACTGGTTTAATGAATGGTTGGGCATTGAAAAAGAAGGAAGTAA
AGTGTTAGAATCAATAGATGAAATAATGGATGAATGAACGAAGGGCATAGCGCTCAATTT
(SEQ ID NO:33)

Influenza B virus (B/Lee/1940) segment 5 (NCBI Ref Seq: NC_002208.1)
GGCAGAAGCACAGCATTTTCTTGTGAGCTTCGAGCACTAATAAAACTGAAAATCAAAATGTC
CAACATGGATATTGACAGTATAAATACCGGAACAATCGATAAAACACCAGAAGAACTGACT
CCCGGAACCAGTGGGGCAACCAGACCAATCATCAAGCCAGCAACCCTTGCTCCGCCAAGC
AACAAACGAACCCGAAATCCATCTCCAGAAAGGACAACCACAAGCAGTGAAACCGATATCG
GAAGGAAAATCCAAAAGAAACAAACCCCAACAGAGATAAAGAAGAGCGTCTACAAAATGGT
GGTAAAACTGGGTGAATTCTACAACCAGATGATGGTCAAAGCTGGACTTAATGATGACATG
GAAAGGAATCTAATTCAAAATGCACAAGCTGTGGAGAGAATCCTATTGGCTGCAACTGATG
ACAAGAAAACTGAATACCAAAAGAAAAGGAATGCCAGAGATGTCAAAGAAGGGAAGGAAG
AAATAGACCACAACAAGACAGGAGGCACCTTTTATAAGATGGTAAGAGATGATAAAACCAT
CTACTTCAGCCCTATAAAAATTACCTTTTTAAAAGAAGAGGTGAAAACAATGTACAAGACCA
CCATGGGGAGTGATGGTTTCAGTGGACTAAATCACATTATGATTGGACATTCACAGATGAA
CGATGTCTGTTTCCAAAGATCAAAGGGACTGAAAAGGGTTGGACTTGACCCTTCATTAATC
AGTACTTTTGCCGGAAGCACACTACCCAGAAGATCAGGTACAACTGGTGTTGCAATCAAAG
GAGGTGGAACTTTAGTGGATGAAGCCATCCGATTTATAGGAAGAGCAATGGCAGACAGAG
GGCTACTGAGAGACATCAAGGCCAAGACGGCCTATGAAAAGATTCTTCTGAATCTGAAAAA
CAAGTGCTCTGCGCCGCAACAAAAGGCTCTAGTTGATCAAGTGATCGGAAGTAGGAACCC
AGGGATTGCAGACATAGAAGACCTAACTCTGCTTGCCAGAAGCATGGTAGTTGTCAGACCC
TCTGTAGCGAGCAAAGTGGTGCTTCCCATAAGCATTTATGCTAAAATACCTCAACTAGGATT
CAATACCGAAGAATACTCTATGGTTGGGTATGAAGCCATGGCTCTTTATAATATGGCAACAC
CTGTTTCCATATTAAGAATGGGAGATGACGCAAAAGATAAATCTCAACTATTCTTCATGTCG
TGCTTCGGAGCTGCCTATGAAGATCTAAGAGTGTTATCTGCACTAACGGGCACCGAATTTA
AGCCTAGATCAGCACTAAAATGCAAGGGTTTCCATGTCCCGGCTAAGGAGCAAGTAGAAG
GAATGGGGGCAGCTCTGATGTCCATCAAGCTTCAGTTCTGGGCCCCAATGACCAGATCTG
GAGGGAATGAAGTAAGTGGAGAAGGAGGGTCTGGTCAAATAAGTTGCAGCCCTGTGTTTG
CAGTAGAAAGACCTATTGCTCTAAGCAAGCAAGCTGTAAGAAGAATGCTGTCAATGAACGT
TGAAGGACGTGATGCAGATGTCAAAGGAAATCTACTCAAAATGATGAATGATTCAATGGCA
AAGAAAACCAGTGGAAATGCTTTCATTGGGAAGAAAATGTTTCAAATATCAGACAAAAACAA
AGTCAATCCCATTGAGATTCCAATTAAGCAGACCATCCCCAATTTCTTCTTTGGGAGGGACA
CAGCAGAGGATTATGATGACCTCGATTATTAAAGCAATAAAATAGACACTATGGCTGTGACT

FIG. 9 (cont'd)

GTTTCAGTACGTTTGGGATGTGGGTGTTTACTCTTATTGAAATAAATGTAAAAAATGCTGTT
GTTTCTACT (SEQ ID NO:34)

Influenza B virus (B/Lee/1940) segment 7 (NCBI Ref Seq: NC_002210.1)
AGCAGAAGCACGCACTTTCTTAAAATGTCGCTGTTTGGAGACACAATTGCCTACCTGCTTT
CACTAATAGAAGATGGAGAAGGCAAAGCAGAACTAGCTGAAAAATTACACTGTTGGTTCGG
TGGGAAAGAATTTGACCTAGATTCTGCTTTGGAATGGATAAAAAACAAAAGGTGCCTAACT
GATATACAAAAAGCACTAATTGGTGCCTCTATATGCTTTTAAAACCCAAAGACCAAGAAAG
AAAAAGGAGATTCATCACAGAGCCCTGTCAGGAATGGGAACAACAGCAACAAGAAGAA
AGGCCTAATTCTAGCTGAGAGAAAAATGAGAAGATGTGTAAGCTTTCATGAAGCATTTGAAA
TAGCAGAAGGCCACGAAAGCTCAGCATTACTATATTGTCTTATGGTCATGTACCTAAACCCT
GAAAACTATTCAATGCAAGTAAAACTAGGAACGCTCTGTGCTTTATGCGAGAAACAAGCAT
CGCACTCGCATAGAGCCCATAGCAGAGCAGCAAGGTCTTCGGTACCTGGAGTAAGACGAG
AAATGCAGATGGTTTCAGCTATGAACACAGCAAAGACAATGAATGGAATGGGAAGGGAGA
AGACGTCCAAAAACTAGCAGAAGAGCTGCAAAACAACATTGGAGTGTTGAGATCTCTAGGA
GCAAGTCAAAAGAATGGAGAAGGAATTGCCAAAGATGTAATGGAAGTGCTAAAACAGAGCT
CTATGGGAAATTCAGCTCTTGTGAGGAAATACTTATAATGCTCGAACCACTTCAGATTCTTT
CAATTTGTTCTTTCATTTTATCAGCTCTCCATTTCATGGCTTGGACAATAGGGCATTTGAATC
AAATAAAAAGAGGGGTAAACTTGAAAATACAAATAAGGAATCCAAATAAGGAGGCAATAAAC
AGAGAGGTGTCAATTCTGAGACACAATTACCAAAAGGAAATCCAAGCCAAAGAAACAATGA
AGAAAATACTCTCTGACAACATGGAAGTATTGGGTGACCACATAGTAGTTGAAGGGCTTTC
AACTGATGAGATAATAAAAATGGGTGAAACAGTTTTGGAGGTGGAAGAATTGCAATGAGCC
CAATTTTCACTGTATTTCTTACTATGCATTTAAGCAAATTGTAATCAATGTCAGTGAATAAAA
CTGGAAAAGTGCGTTGTTTCTACT (SEQ ID NO:35)

Influenza B virus (B/Lee/1940) segment 8 (NCBI Ref Seq: NC_002211.1)
CGCAGAAGCAGAGGATTTATTTAGTCACTGGCAAACGGAAAGATGGCGGACAACATGACC
ACAACACAAATTGAGGTGGGTCCGGGAGCAACCAATGCCACTATAAACTTTGAAGCAGGAA
TTCTGGAGTGCTATGAAAGGTTTTCATGGCAAAGAGCCCTTGACTATCCTGGTCAAGACCG
CCTACACAGACTAAAACGAAAATTAGAATCAAGAATAAAGACTCACAACAAGAGTGAGCCT
GAGAATAAAAGGATGTCTCTTGAAGAGAGAAAAGCAATTGGGGTAAAAATGATGAAAGTGC
TTCTGTTTATGGATCCCTCTGCTGGAATTGAAGGGTTTGAGCCATACTGTGTGAAAAATCCC
TCAACTAGCAAATGTCCAAATTACGATTGGACCGATTACCCTCCAACCCCAGGAAAGTACC
TTGATGACATAGAAGAAGAGCCGGAAAATGTCGATCACCCAATTGAGGTAGTATTAAGGGA
CATGAACAATAAAGATGCACGACAAAGATAAAGGATGAAGTAAACACTCAGAAAGAGGGG
AAATTCCGTTTGACAATAAAAAGGGATATACGTAATGTGTTGTCCTTGAGAGTGTTGGTGAA
CGGAACCTTCCTCAAGCACCCTAATGGAGACAAGTCCTTATCAACTCTTCATAGATTGAATG
CATATGACCAGAATGGAGGGCTTGTTGCTAAACTTGTTGCTACTGATGATCGGACAGTGGA
GGATGAAAAGATGGCCATCGGATCCTCAACTCACTCTTCGAGCGTTTTGATGAAGGACAT
TCAAAGCCAATTCGAGCAGCTGAAACTGCGGTGGAGTCTTATCCCAATTTGGTCAAGAGC
ACCGATTATCACCAGAAGAGGGAGACAATTAGACTGGCCACGGAAGAACTTTATCTCTTGA
GTAAAAGAATTGATGATAGTATATTGTTCCACAAAACAGTAATAGCTAACAGCTCCATAATA
GCTGACATGATTGTATCATTATCATTACTGGAAACATTGTATGAAATGAAGGATGTGGTTGA
AGTGTACAGCAGGCAGTGCTTATGAATGTAAAATAAAAATCCTCTTGTTACTACT (SEQ ID
NO:36)

SEQUENCE LISTING

<160> NUMBER OF SEQ ID NOS: 40

<210> SEQ ID NO 1
<211> LENGTH: 99
<212> TYPE: DNA
<213> ORGANISM: Influenza A virus

<400> SEQUENCE: 1

| | | | | | |
|---|---|---|---|---|---|
| agcaaaagca | gggaaaata | aaaacaacca | aattgaaggc | aaacctactg | gtcctgttaa | 60 |
| gtgcacttgc | agctgcagtt | gcagacacaa | tttgtatag | | | 99 |

<210> SEQ ID NO 2
<211> LENGTH: 150
<212> TYPE: DNA
<213> ORGANISM: Influenza A virus

<400> SEQUENCE: 2

| | | | | | |
|---|---|---|---|---|---|
| atctactcaa | ctgtcgccag | ttcactggtg | cttttggtct | ccctgggggc | aatcagtttc | 60 |
| tggatgtgtt | ctaatggatc | tttgcagtgc | agaatatgca | tctgagatta | gaatttcaga | 120 |
| aatatgagga | aaacacccct | tgtttctact | | | | 150 |

<210> SEQ ID NO 3
<211> LENGTH: 173
<212> TYPE: DNA
<213> ORGANISM: Influenza A virus

<400> SEQUENCE: 3

| | | | | | |
|---|---|---|---|---|---|
| agcgaaagca | ggggtttaaa | ttgaatccaa | atcagaaaat | aacaaccatt | ggatcaatct | 60 |
| gtctggtagt | cggactaatt | agcctaatat | tgcaaatagg | gaatataatc | tcaatttgga | 120 |
| ttagccattc | aattcaaact | ggaagtcaaa | accatactgg | aatttgcaac | caa | 173 |

<210> SEQ ID NO 4
<211> LENGTH: 209
<212> TYPE: DNA
<213> ORGANISM: Influenza A virus

<400> SEQUENCE: 4

| | | | | | |
|---|---|---|---|---|---|
| tgagctaaca | gggctagact | gtatgaggcc | gtgcttctgg | gttgaattaa | tcaggggacg | 60 |
| acctaaagaa | aaaacaatct | ggactagtgc | gagcagcatt | tcttttttgtg | gcgtgaatag | 120 |
| tgatactgta | gattggtctt | ggccagacgg | tgctgagttg | ccattcagca | ttgacaagta | 180 |
| gtctgttcaa | aaaactcctt | gtttctact | | | | 209 |

<210> SEQ ID NO 5
<211> LENGTH: 1778
<212> TYPE: DNA
<213> ORGANISM: Influenza A virus

<400> SEQUENCE: 5

| | | | | | |
|---|---|---|---|---|---|
| agcaaaagca | gggaaaata | aaaacaacca | aaatgaaggc | aaacctactg | gtcctgttat | 60 |
| gtgcacttgc | agctgcagat | gcagacacaa | tatgtatagg | ctaccatgcg | aacaattcaa | 120 |
| ccgacactgt | tgacacagtg | ctcgagaaga | atgtgacagt | gacacactct | gttaacctgc | 180 |
| tcgaagacag | ccacaacgga | aaactatgta | gattaaaagg | aatagcccca | ctacaattgg | 240 |
| ggaaatgtaa | catcgccgga | tggctcttgg | gaaacccaga | atgcgaccca | ctgcttccag | 300 |
| tgagatcatg | gtcctacatt | gtagaaacac | caaactctga | gaatggaata | tgttatccag | 360 |
| gagatttcat | cgactatgag | gagctgaggg | agcaattgag | ctcagtgtca | tcattcgaaa | 420 |
| gattcgaaat | atttcccaaa | gaaagctcat | ggcccaacca | caacacaacc | aaaggagtaa | 480 |
| cggcagcatg | ctcccatgcg | gggaaaagca | gtttttacag | aaatttgcta | tggctgacgg | 540 |
| agaaggaggg | ctcatacccca | aagctgaaaa | attcttatgt | gaacaagaaa | gggaaagaag | 600 |

```
tccttgtact gtggggtatt catcacccgt ctaacagtaa ggatcaacag aatatctatc      660
agaatgaaaa tgcttatgtc tctgtagtga cttcaaatta taacaggaga tttaccccgg      720
aaatagcaga aagacccaaa gtaagagatc aagctgggag gatgaactat tactggacct      780
tgctaaaacc cggagacaca ataatatttg aggcaaatgg aaatctaata gcaccaaggt      840
atgctttcgc actgagtaga ggctttgggt ccggcatcat cacctcaaac gcatcaatgc      900
atgagtgtaa cacgaagtgt caaacacccc tgggagctat aaacagcagt ctccctttcc      960
agaatataca cccagtcaca ataggagagt gcccaaaata cgtcaggagt gccaaattga     1020
ggatggttac aggactaagg aacattccgt ccattcaatc agaggtctta tttggagcca     1080
ttgccggttt tattgaaggg ggatggactg gaatgataga tggatggtac ggttatcatc     1140
atcagaatga acagggatca ggctatgcag cggatcaaaa aagcacacaa aatgccatta     1200
acgggattac aaacaaggtg aactctgtta tcgagaaaat gaacattcaa ttcacagctg     1260
tgggtaaaga attcaacaaa ttagaaaaaa ggatggaaaa tttaaataaa aaagttgatg     1320
atgggtttct ggacatttgg acatataatg cagaattgtt agttctactg gaaaatgaaa     1380
ggactctgga tttccatgac tcaaatgtga gaatctgta tgagaaagta aaaagccaat     1440
taaagaataa tgccaaagaa atcggaaatg gatgttttga gttctaccac aagtgtgaca     1500
atgaatgcat ggaaagtgta agaaatggga cttatgatta tcccaaatat tcagaagagt     1560
caaagttgaa cagggaaaag gtagatggag tgaaattgga atcaatgggg atctatcaga     1620
ttctggcgat ctactcaact gtcgccagtt cactggtgct tttggtctcc ctgggggcaa     1680
tcagtttctg gatgtgttct aatggatctt tgcagtgcag aatatgcatc tgagattaga     1740
atttcagaaa tatgaggaaa acacccttg tttctact                              1778

<210> SEQ ID NO 6
<211> LENGTH: 1413
<212> TYPE: DNA
<213> ORGANISM: Influenza A virus

<400> SEQUENCE: 6
agcgaaagca ggggtttaaa atgaatccaa atcagaaaat aataaccatt ggatcaatct      60
gtctggtagt cggactaatt agcctaatat tgcaaatagg aatataatc tcaatatgga      120 ttagccattc aattcaaact ggaagtcaaa accatactgg aatatgcaac caaaacatca      180
ttacctataa aaatagcacc tgggtaaagg acacaacttc agtgatatta accggcaatt      240
catctctttg tccatccgt gggtgggcta tatacagcaa agacaatagc ataagaattg      300
gttccaaagg agacgttttt gtcataagag agccctttat ttcatgttct cacttggaat      360
gcaggacctt ttttctgacc caaggtgcct tactgaatga caggcattca atgggactg      420 ttaaggacag aagcccttat agggccttaa tgagctgccc tgtcggtgaa gctccgtccc      480
cgtacaattc aagatttgaa tcggttgctt ggtcagcaag tgcatgtcat gatggcatgg      540
gctggctaac aatcggaatt tcaggtccag ataatggagc agtggctgta ttaaaataca      600
acggcataat aactgaaacc ataaaaagtt ggaggaagaa atattgagg acacaagagt      660 ctgaatgtgc ctgtgtaaat ggttcatgtt ttactataat gactgatggc ccagtgatg      720 ggctggcctc gtacaaaatt ttcaagatcg aaaagggga ggttactaaa tcaatagagt      780
tgaatgcacc taattctcac tatgaggaat gttcctgtta ccctgatacc ggcaaagtga      840
tgtgtgtgtg cagagacaat tggcatggtt cgaaccggcc atgggtgtct ttcgatcaaa      900
acctggatta tcaaatagga tacatctgca gtgggtgttt cggtgacaac ccgcgtccca      960
```

```
aagatggaac aggcagctgt ggtccagtgt atgttgatgg agcaaacgga gtaaagggat    1020
tttcatatag gtatggtaat ggtgtttgga taggaaggac caaaagtcac agttccagac    1080 atggggtttga gatgatttgg gatcctaatg gatggacaga gactgatagt aagttctctg   1140
tgaggcaaga tgttgtggca atgactgatt ggtcagggta tagcgggagt ttcgttcaac    1200
atcctgagct aacagggcta gactgtataa ggccgtgctt ctgggttgaa ttaatcaggg    1260
gacgacctaa agaaaaaaca atctggacta gtgcgagcag catttctttt tgtggcgtga   1320
atagtgatac tgtagattgg tcttggccag acggtgctga gttgccattc accattgaca   1380
agtagtctgt tcaaaaaact ccttgtttct act                                1413
```

```
<210> SEQ ID NO 7
<211> LENGTH: 1762
<212> TYPE: DNA
<213> ORGANISM: Influenza A virus

<400> SEQUENCE: 7
```

```
agcaaaagca gggataatt ctattaacca tgaagactat cattgctttg agctacattc      60
tatgtctggt tttcgctcaa aaacttcccg gaaatgacaa cagcacggca acgctgtgcc    120
ttgggcacca tgcagtacca acggaacga tagtgaaaac aatcacgaat gaccaaattg     180
aagtcactaa tgctactgaa ctggttcaga gttcctcaac aggtggaata tgcgacagtc    240
ctcatcagat ccttgatgga gaaaactgca cactaataga tgctctattg ggagaccctc    300
agtgtgatgg cttccaaaat aagaaatggg accttttgt tgaacgcagc aaagcctaca    360
gcaactgtta cccttatgat gtgccggatt atgcctccct taggtcacta gttgcctcat    420
ccggcacact ggagtttaac aatgaaagct tcaattggac tggagtcact caaaatggaa    480
caagctctgc ttgcaaaagg agatctaata acagtttctt tagtagattg aattggttga    540
cccacttaaa attcaaatac ccagcattga acgtgactat gccaaacaat gaaaaatttg    600
acaaactgta catttggggg gttcaccacc cgggtacgga caatgaccaa atcagcctat    660
atgctcaagc atcaggaaga atcacagtct ctaccaaaag aagccaacaa accgtaatcc    720
cgagtatcgg atctagaccc aggataaggg atgtccccag cagaataagc atctattgga    780
caatagtaaa accgggagac atactttga ttaacagcac agggaatcta attgctcctc     840
ggggttactt caaaatacga agtgggaaaa gctcaataat gagatcagat gcacccattg   900
gcaaatgcaa ttctgaatgc atcactccaa atggaagcat tcccaatgac aaaccatttc   960
aaaatgtaaa caggatcaca tatgggcct gtcccagata tgttaagcaa acactctga    1020 aattggcaac agggatgcga atgtaccaga gaaacaaac tagaggcata tttggcgcaa   1080
tcgcgggttt catagaaaat ggttgggagg gaatggtaga cggttggtac ggtttcaggc    1140
atcaaaattc tgagggaaca ggacaagcag cagatctcaa aagcactcaa gcagcaatca   1200
accaaatcaa tgggaagctg aataggttga tcgggaaaac aaacgagaaa ttccatcaga    1260
ttgaaaaaga attctcagaa gtagaaggga gaattcagga cctcgagaaa tatgttgagg    1320
acactaaaat agatctctgg tcatacaacg cggagcttct tgtggccctg gagaaccaac    1380
atacaattga tctaactgac tcagaaatga acaaactgtt tgaaaagaca aagaagcaac    1440
tgagggaaaa tgctgaggat atgggcaatg gttgtttcaa aatataccac aaatgtgaca    1500
atgcctgcat agggtcaatc agaaatggaa cttatgacca tgatgtatac agagatgaag    1560
cattaaacaa ccggttccag atcaaaggtg ttgagttgaa gtcaggatac aaagattgga    1620
```

-continued

```
tcctatggat ttcctttgcc atatcatgtt ttttgctttg tgttgctttg ttggggttca   1680
tcatgtgggc ctgccaaaaa ggcaacatta ggtgcaacat ttgcatttga gtgcattaat   1740
taaaaacacc cttgtttcta ct                                            1762
```

<210> SEQ ID NO 8
<211> LENGTH: 1467
<212> TYPE: DNA
<213> ORGANISM: Influenza A virus

<400> SEQUENCE: 8

```
agcaaaagca ggagtaaaga tgaatccaaa tcaaaagata ataacgattg gctctgtttc     60
tctcaccatt tccacaatat gcttcttcat gcaaattgcc atcctgataa ccactgtaac    120
attgcatttc aagcaatatg aattcaactc ccccccaaac aaccaagtga tgctgtgtga    180
accaacaata atagaaagaa acataacaga gatagtgtat ctgaccaaca ccaccataga    240
gaaggaaatg tgccccaaac tagcagaata cagaaattgg tcaaagccgc aatgtgacat    300
tacaggattt gcaccttttt ctaaggacaa ttcgattagg ctttccgctg gtggggacat    360
ctgggtgaca agagaacctt atgtgtcatg cgaccctgac aagtgttacc aatttgccct    420
tggacaggga acaacactaa acaacgtgca ttcaaatgac acagtacatg ataggacccc    480
ttatcggacc ctattgatga atgaattagg tgttccattt catctgggga ccaagcaagt    540
gtgcatagca tggtccagct caagttgtca cgatggaaaa gcatggctgc atgtttgtgt    600
aacgggggat gataaaaatg caactgctag cttcatttac aatgggaggc ttgtagatag    660
tattgtttca tggtccaaaa aaatcctcag gacccaggag tcagaatgcg tttgtatcaa    720
tggaacttgt acagtagtaa tgactgatgg gagtgcttca ggaaaagctg atactaaaat    780
actattcatt gaggagggga aaatcattca tactagcaca ttgtcaggaa gtgctcagca    840
tgtcgaggag tgctcctgct atcctcgata tcctggtgtc agatgtgtct gcagagacaa    900
ctggaaaggc tccaataggc ccatcgtaga tataaacata aaggattata gcattgtttc    960
cagttatgtg tgctcagggc ttgttggaga cacacccaga aaaaacgaca gctccagcag   1020
tagccattgc ttggatccta acaatgaaga aggtggtcat ggagtgaaag gctgggcctt   1080
tgatgatgga aatgacgtgt ggatgggaag aacgatcagc gagaagttac gctcaggata   1140
tgaaaccttc aaagtcattg aaggctggtc caaacctaat tccaaattgc agataaatag   1200
gcaagtcata gttgacagag gtaataggtc cggttattct ggtattttct ctgttgaagg   1260
caaaagctgc atcaatcggt gcttttatgt ggagttgata aggggaagaa aagaggaaac   1320
tgaagtcttg tggacctcaa acagtattgt tgtgttttgt ggcacctcag gtacatatgg   1380
aacaggctca tggcctgatg ggcggacat caatctcatg cctatataag ctttcgcaat    1440
tttagaaaaa aactccttgt ttctact                                       1467
```

<210> SEQ ID NO 9
<211> LENGTH: 1760
<212> TYPE: DNA
<213> ORGANISM: Influenza A virus

<400> SEQUENCE: 9

```
gcaggggtat aatctgtcaa aatggagaaa atagtgcttc ttcttgcaat agtcagtctt     60
gtcaaaagtg atcagatttg cattggttac catgcaaaca actcgacaga gcaggttgac    120
acaataatgg aaaagaacgt tactgttaca catgcccaag acatactgga aaagacacac    180
aatgggaagc tctgcgatct aaatggagtg aagcctctca ttttgagaga ttgtagtgta    240
```
gctggatggc tcctcggaaa ccctatgtgt gacgaattca tcaatgtgcc ggaatggtct 300
tacatagtgg agaaggccag tccagccaat gacctctgtt acccagggga tttcaacgac 360
tatgaagaac tgaaacacct attgagcaga acaaaccatt ttgagaaaat tcagatcatc 420
cccaaaagtt cttggtccaa tcatgatgcc tcatcagggg tgagctcagc atgtccatac 480
catgggaggt cctccttttt cagaaatgtg gtatggctta tcaaaaagaa cagtgcatac 540
ccaacaataa agaggagcta caataatacc aaccaagaag atctttagt actgtggggg 600 attcaccatc ctaatgatgc ggcagagcag acaaagctct atcaaaaccc aaccacttac 660
atttccgttg gaacatcaac actgaaccag agattggttc cagaaatagc tactagaccc 720
aaagtaaacg ggcaaagtgg aagaatggag ttcttctgga caattttaaa gccgaatgat 780
gccatcaatt tcgagagtaa tggaaatttc attgctccag aatatgcata caaaattgtc 840
aagaaagggg actcagcaat tatgaaaagt gaattggaat atggtaactg caacaccaag 900
tgtcaaactc caatgggggc gataaactct agtatgccat tccacaacat acacccctc 960 accatcgggg aatgccccaa atatgtgaaa tcaaacagat tagtccttgc gactggactc 1020
agaaataccc ctcagagaga gagaagaaga aaaaagagag gactatttgg agctatagca 1080
ggttttatag agggaggatg gcagggaatg gtagatggtt ggtatgggta ccaccatagc 1140
aatgagcagg ggagtggata cgctgcagac aaagaatcca ctcaaaaggc aatagatgga 1200
gtcaccaata aggtcaactc gatcattgac aaaatgaaca ctcagtttga ggccgttgga 1260
agggaattta ataacttgga aaggaggata gagaatttaa acaagcagat ggaagacgga 1320
ttcctagatg tctggactta taatgctgaa cttctggttc tcatggaaaa tgagagaact 1380
ctagactttc atgactcaaa tgtcaagaac ctttatgaca aggtccgact acagcttagg 1440
gataatgcaa aggagctggg taatggttgt ttcgagttct atcacaaatg tgataatgaa 1500
tgtatggaaa gtgtaaaaaa cggaacgtat gactacccgc agtattcaga agaagcaaga 1560
ctaaacagag aggaaataag tggagtaaaa ttggaatcaa tgggaactta ccaaatactg 1620
tcaatttatt caacagtggc gagttcccta gcactggcaa tcatggtagc tggtctatct 1680
ttatggatgt gctccaatgg atcgttacaa tgcagaattt gcatttaaat ttgtgagttc 1740
agattgtagt taaaaacacc 1760

<210> SEQ ID NO 10
<211> LENGTH: 1458
<212> TYPE: DNA
<213> ORGANISM: Influenza A virus

<400> SEQUENCE: 10
agcaaaagca ggagattaaa atgaatccaa atcagaagat aataaccatt ggatcaatct 60
gtatggtagt tgggataatt agcttgatgt tacaaattgg gaacataatc tcaatatggg 120
tcagtcattc aattcagaca gggaatcaac accaagctga accatgcaat caaagcatta 180
ttacttatga aaacaacacc tgggtaaatc aaacatatgt caacatcagc aataccaatt 240
ttcttactga aaaagctgtg gcttcagtaa cattagcggg caattcatct ctttgcccca 300
ttagcggatg ggctgtacac agtaaggaca acggtataag aatcggttcc aagggggatg 360
tgtttgttat aagagagccg ttcatctcat gctcccactt ggaatgcaga actttctttt 420
tgactcaggg agccttgctg aatgacaagc actccaatgg gaccgtcaaa gacagaagcc 480
ctcacagaac attgatgagt tgtcctgtgg gtgaggctcc ctccccatat aactcaaggt 540

```
ttgagtctgt tgcttggtcg gcaagtgctt gccatgatgg caccagttgg ttgacaattg    600
gaatttctgg cccagacaat ggggctgtgg ctgtattgaa atacaacggc ataataacag    660
acactatcaa gagttggagg aacaacatac tgagaactca agagtctgaa tgtgcatgtg    720
taaatggctc ttgctttact gtaatgactg acggaccaag taatgggcag gcctcatata    780
agatcttcaa aatggaaaaa gggaaagtag ttaaatcagt cgaattgaat gcccctaatt    840
atcactatga ggagtgctcc tgttatcctg atgctggcga aatcacatgt gtgtgcaggg    900
ataattggca tggctcaaat cggccatggg tatctttcaa tcaaaatttg gagtatcaaa    960
taggatatat atgcagtgga gttttcggag acaatccacg ccccaatgat ggaacaggca   1020
gttgtggtcc ggtgtcccct aacggggcat atggagtaaa agggttttca tttaaatacg   1080
gcaatggtgt ttggatcggg agaaccaaaa gcactaattc caggagcggc tttgaaatga   1140
tttgggatcc aaatgggtgg actggaacgg acagtagctt ctcggtgaaa caagatatcg   1200
tagcaataac tgattggtca ggatatagcg gagttttgt ccagcatcca gaactgacag   1260
gattagattg cataagacct tgtttctggg ttgagctaat cagagggcgg cccaaagaga   1320
gcacaatttg gactagtggg agcagcatat cttttgtgg tgtaaatagt gacactgtgg   1380
gttggtcttg gccagacgat gccgagttgc cattcaccat tgacaagtag tttgttcaaa   1440
aaactccttg tttctact                                                  1458

<210> SEQ ID NO 11
<211> LENGTH: 1882
<212> TYPE: DNA
<213> ORGANISM: Influenza A virus

<400> SEQUENCE: 11
agcagaagcg ttgcattttc taatatccac aaaatgaagg caataattgt actactcatg     60
gtagtaacat ccaatgcaga tcgaatctgc actgggataa catcgtcaaa ctcacctcat    120
gtggttaaaa ctgccactca aggggaagtc aatgtgactg tgtgatacc actaacaaca    180 acacctacca atctcatttt gcaaatctc aaggaacac agaccagagg aaaactatgc    240
ccaaactgtt ttaactgcac agatctggac gtggccctag cagaccaaa atgcatgggg    300 aacacaccct ccgcaaaagt ctcaatactc catgaagtca aacctgctac atctggatgc    360
tttcctataa tgcacgacag aacaaaaatc agacaactac ctaatcttct cagaggatat    420
gaaaacatca ggttatcaac cagtaatgtt atcaatacag acggcacc aggaggaccc    480 tacaaggtgg ggacctcagg atcttgccct aacgttgcta atgggaacgg cttcttcaac    540
acaatggctt gggttatccc aaaagacaac aacaagacag caataaatcc agtaacagta    600
gaagtaccat acatttgttc agaaggggaa gaccaaatta ctgttttggg gttccactct    660
gatgacaaaa cccaaatgga aagactctat ggagactcaa atcctcaaaa gttcacctca    720
tctgccaatg gagtaaccac acattatgtt tctcagattg gtggcttccc aaatcaaaca    780
gaagacgaag gctaaaaca aagcggcaga attgttgttg attacatggt acaaaaacct    840
ggaaaaacag gaacaattgt ttatcaaaga ggcattttat tgcctcaaaa agtgtggtgc    900
gcaagtggca ggagcaaggt aataaaaggg tccttgcctt taattggtga agcagattgc    960
ctccacgaaa agtacggtgg attaaataaa agcaagcctt actacacagg agagcatgca   1020
aaggccatag gaaattgccc aatatgggtg aaaacacccct tgaagctggc caatggaacc   1080
aaatatagac cgcctgcaaa actattaaag gaaagaggtt tcttcggagc tattgctggt   1140
ttcttggaag gaggatggga aggaatgatt gcaggttggc acggatacac atctcatgga   1200
```

-continued

```
gcacatggag tggcagtggc agcagacctt aagagtacac aagaagctat aaacaagata    1260
acaaaaaatc tcaactattt aagtgagcta gaagtaaaaa accttcaaag actaagcgga    1320
gcaatgaatg agcttcacga cgaaatactc gagctagacg aaaaagtgga tgatctaaga    1380
gctgatacaa taagctcaca aatagagctt gcagtcttgc tttccaacga agggataata    1440
aacagtgaag atgagcatct cttggcactt gaaagaaaac tgaagaaaat gcttggcccc    1500
tctgctgtag aaatagggaa tgggtgcttt gaaaccaaac acaaatgcaa ccagacttgc    1560
ctagacagga tagctgctgg cacctttaat gcaggagatt tttctcttcc cacttttgat    1620
tcattaaaca ttactgctgc atctttaaat gatgatggct tggataatca tactatactg    1680
ctctactact caactgctgc ttctagcttg gctgtaacat taatgatagc tatcttcatt    1740
gtctacatgg tctccagaga caatgtttct tgttccatct gtctgtgagg gagattaagc    1800
cctgtgtttt cctttactgt agtgctcatt tgcttgtcac cattacaaag aaacgttatt    1860
gaaaaatgct cttgttacta ct                                             1882

<210> SEQ ID NO 12
<211> LENGTH: 1557
<212> TYPE: DNA
<213> ORGANISM: Influenza A virus

<400> SEQUENCE: 12
agcagaagca gagcatattc ttagaactga agtgaacagg ccaaaaatga acaatgctac      60
cttcaactgt acaaacatta accctattac tcacatcagg gggagtatta ttatcactat     120
atgtgtcagc ctcattgtca tacttattgt attcggatgt attgctaaaa ttttcatcaa     180
caaaaacaac tgcaccaaca atgtcattag agtgcacaaa cgcatcaaat gcccagactg     240
tgaaccattc tgcaacaaaa gagatgacat ttccaccccc agagccggag tggacatacc     300
ctcgtttatc ttgccagggc tcaaccttc agaaggcact cctaattagc cctcataggt     360
tcggagagat caaggaaac tcagctccct tgataataag agaaccttttt gttgcttgtg     420 gaccaaaaga atgcagacac tttgctctga cccattatgc agctcagccg gggggatact     480
acaatggaac aagaaaggac agaaacaagc tgaggcatct agtatcagtc aaattgggaa     540
aaatcccaac tgtggaaaac tccatttttcc acatggcagc ttggagcgga tccgcatgcc     600
atgatggtag agaatggaca tatatcggag ttgatggtcc tgacaatgat gcattggtca     660
aaataaaata tggagaagca tatactgaca catatcattc ctatgcacac aacatcctaa     720
gaacacaaga aagtgcctgc aattgcatcg ggggagattt atcttatg ataacagacg     780 gctcagcttc aggaattagt aaatgcagat tcttaaaaat tagagagggt cgaataataa     840
aagaaatact tccaacagga agagtggagc acactgaaga gtgcacatgc gggttcgcca     900
gcaataaaac catagaatgt gcctgtagag acaacagtta cacagcaaaa agacccttg     960 tcaaattaaa tgtggaaact gatacagctg aaataagatt gatgtgcaca aagacttatc    1020
tagacactcc cagaccggat gatggaagca tagcagggcc ttgcgaatct aatggagaca    1080
agtggcttgg aggcatcaaa ggaggattcg tccatcaaag aatggcatct aagattggaa    1140
gatggtactc ccgaacgatg tctaaaacta acagaatggg gatggaactg tatgtaaagt    1200
atgatggtga cccatggact gacagtgatg ctcttactct tagtggagta atggtttcca    1260
tagaagaacc tggttggtat tcttttggct tcgaaataaa ggacaagaaa tgtgatgtcc    1320
cttgtattgg gatagagatg gtacacgatg gtggaaaaga tacttggcat tcagctgcaa    1380
```

-continued

| | |
|---|---|
| cagccattta ctgtttgatg ggctcaggac aattgctatg ggacactgtc acaggcgttg | 1440 |
| atatggcttt ataatagagg aatggttgga tctgttctaa acctttgtt cctattttat | 1500 |
| ttgaacagtt gttcttacta gatttaattg tttctgaaaa atgctcttgt tactact | 1557 |

<210> SEQ ID NO 13
<211> LENGTH: 2341
<212> TYPE: DNA
<213> ORGANISM: Influenza A virus

<400> SEQUENCE: 13

| | |
|---|---|
| agcgaaagca ggtcaattat attcaatatg gaaagaataa agaactaag aaatctaatg | 60 |
| tcgcagtctc gcacccgcga gatactcaca aaaaccaccg tggaccatat ggccataatc | 120 |
| aagaagtaca catcaggaag acaggagaag acccagcac ttaggatgaa atggatgatg | 180 |
| gcaatgaaat atccaattac agcagacaag aggataacgg aaatgattcc tgagagaaat | 240 |
| gagcaaggac aaactttatg gagtaaaatg aatgatgccg atcagaccg agtgatggta | 300 |
| tcacctctgg ctgtgacatg gtggaatagg aatggaccaa tgacaaatac agttcattat | 360 |
| ccaaaaatct acaaaactta ttttgaaaga gtcgaaaggc taaagcatgg aacctttggc | 420 |
| cctgtccatt ttagaaacca agtcaaaata cgtcggagag ttgacataaa tcctggtcat | 480 |
| gcagatctca gtgccaagga ggcacaggat gtaatcatgg aagttgtttt ccctaacgaa | 540 |
| gtgggagcca ggatactaac atcggaatcg caactaacga taaccaaaga gaagaaagaa | 600 |
| gaactccagg attgcaaaat ttctcctttg atggttgcat acatgttgga gagagaactg | 660 |
| gtccgcaaaa cgagattcct cccagtggct ggtggaacaa gcagtgtgta cattgaagtg | 720 |
| ttgcatttga ctcaaggaac atgctgggaa cagatgtata ctccaggagg ggaagtgaag | 780 |
| aatgatgatg ttgatcaaag cttgattatt gctgctagga acatagtgag aagagctgca | 840 |
| gtatcagcag acccactagc atctttattg gagatgtgcc acagcacaca gattggtgga | 900 |
| attaggatgt tagacatcct taagcagaac ccaacagaag agcaagccgt gggtatatgc | 960 |
| aaggctgcaa tgggactgag aattagctca tccttcagtt ttggtggatt cacatttaag | 1020 |
| agaacaagcg gatcatcagt caagagagag gaagaggtgc ttacgggcaa tcttcaaaca | 1080 |
| ttgaagataa gagtgcatga gggatatgaa gagttcacaa tggttgggag aagagcaaca | 1140 |
| gccatactca gaaaagcaac caggagattg attcagctga tagtgagtgg gagagacgaa | 1200 |
| cagtcgattg ccgaagcaat aattgtggcc atggtatttt cacaagagga ttgtatgata | 1260 |
| aaagcagtta gaggtgatct gaatttcgtc aatagggcga atcagcgact gaatcctatg | 1320 |
| catcaacttt taagacattt tcagaaggat gcgaaagtgc ttttttcaaaa ttggggagtt | 1380 |
| gaacctatcg acaatgtgat gggaatgatt gggatattgc ccgacatgac tccaagcatc | 1440 |
| gagatgtcaa tgagaggagt gagaatcagc aaaatgggtg tagatgagta ctccagcacg | 1500 |
| gagagggtag tggtgagcat tgaccggttc ttgagagtcc gggaccaacg aggaaatgta | 1560 |
| ctactgtctc ccgaggaggt cagtgaaaca caggaacag agaaactgac aataacttac | 1620 |
| tcatcgtcaa tgatgtggga gattaatggt cctgaatcag tgttggtcaa tacctatcaa | 1680 |
| tggatcatca gaaactggga aactgttaaa attcagtggt cccagaaccc tacaatgcta | 1740 |
| tacaataaaa tggaatttga accatttcag tctttagtac ctaaggccat tagaggccaa | 1800 |
| tacagtgggt ttgtgagaac tctgttccaa caaatgaggg atgtgcttgg gacatttgat | 1860 |
| accgcacaga taataaaact tcttcccttc gcagccgctc caccaaagca agtagaatg | 1920 |
| cagttctcct catttactgt gaatgtgagg ggatcaggaa tgagaatact tgtaaggggc | 1980 |

```
aattctcctg tattcaacta caacaaggcc acgaagagac tcacagttct cggaaaggat    2040
gctggcactt taaccgaaga cccagatgaa ggcacagctg gagtggagtc cgctgttctg    2100 agggattcc tcattctggg caaagaagac aggagatatg gccagcatt aagcatcaat      2160 gaactgagca accttgcgaa aggagagaag gctaatgtgc taattgggca aggagacgtg    2220
gtgttggtaa tgaaacgaaa acgggactct agcatactta ctgacagcca gacagcgacc    2280
aaaagaattc ggatggccat caattagtgt cgaatagttt aaaaacgacc ttgtttctac    2340
t                                                                    2341

<210> SEQ ID NO 14
<211> LENGTH: 2341
<212> TYPE: DNA
<213> ORGANISM: Influenza A virus

<400> SEQUENCE: 14
agcgaaagca ggcaaaccat ttgaatggat gtcaatccga ccttactttt cttaaaagtg      60
ccagcacaaa atgctataag cacaactttc ccttataccg agaccctcc ttacagccat     120 gggacaggaa caggatacac catggatact gtcaacagga cacatcagta ctcagaaaag    180
gcaagatgga caacaaacac cgaaactgga gcaccgcaac tcaacccgat tgatgggcca    240
ctgccagaag acaatgaacc aagtggttat gcccaaacag attgtgtatt ggaagcaatg    300
gctttccttg aggaatccca tcctggtatt tttgaaaact cgtgtattga acgatggag     360 gttgttcagc aaacacgagt agacaagctg acacaaggcc gacagaccta tgactggact    420
ttaaatagaa accagcctgc tgcaacagca ttggccaaca caatagaagt gttcagatca    480
aatggcctca cggccaatga gtctggaagg ctcatagact ccttaaggga tgtaatggag    540
tcaatgaaaa agaagaaat ggggatcaca actcattttc agagaaagag acgggtgaga    600
gacaatatga ctaagaaaat gataacacag agaacaatag gtaaaggaa acagagattg    660 aacaaaagga gttatctaat tagagcattg accctgaaca caatgaccaa agatgctgag    720
agagggaagc taaaacggag agcaattgca ccccaggga tgcaaataag ggggtttgta    780
tactttgttg agacactggc aaggagtata tgtgagaaac ttgaacaatc agggttgcca    840
gttggaggca atgagaagaa agcaaagttg gcaaatgttg taaggaagat gatgaccaat    900
tctcaggaca ccgaactttc tttgaccatc actggagata caccaaatg gaacgaaaat    960 cagaatcctc ggatgttttt ggccatgatc acatatatga ccagaaatca gcccgaatgg   1020
ttcagaaatg ttctaagtat tgctccaata atgttctcaa acaaaatggc gagactggga   1080
aaagggtata tgtttgagag caagagtatg aaacttagaa ctcaaatacc tgcagaaatg   1140
ctagcaagca ttgatttgaa atatttcaat gattcaacaa gaagaagat tgaaaaatc    1200 cgaccgctct aatagaggg gactgcatca ttgagccctg aatgatgat gggcatgttc    1260 aatatgttaa gcactgtatt aggcgtctcc atcctgaatc ttggacaaaa gagatacacc   1320
aagactactt actggtggga tggtcttcaa tcctctgacg atttttgctct gattgtgaat   1380 gcacccaatc atgaagggat tcaagccgga gtcgacaggt tttatcgaac ctgtaagcta   1440
catggaatca atatgagcaa gaaaaagtct tacataaaca gaacaggtac atttgaattc    1500
acaagttttt tctatcgtta tgggtttgtt gccaatttca gcatggagct tcccagtttt   1560
ggtgtgtctg ggagcaacga gtcagcggac atgagtattg gagttactgt catcaaaaac   1620
aatatgataa acaatgatct tggtccagca acagctcaaa tggcccttca gttgttcatc   1680
```

-continued

| | |
|---|---|
| aaagattaca ggtacacgta ccgatgccat agaggtgaca cacaaataca aacccgaaga | 1740 |
| tcatttgaaa taaagaaact gtgggagcaa acccgttcca aagctggact gctggtctcc | 1800 |
| gacggaggcc caaatttata caacattaga atctccaca ttcctgaagt ctgcctaaaa | 1860 |
| tgggaattga tggatgagga ttaccagggg cgtttatgca acccactgaa cccatttgtc | 1920 |
| agccataaag aaattgaatc aatgaacaat gcagtgatga tgccagcaca tggtccagcc | 1980 |
| aaaaacatgg agtatgatgc tgttgcaaca acacactcct ggatcccaa agaaatcga | 2040 |
| tccatcttga atacaagtca agaggagta cttgaagatg aacaaatgta ccaaaggtgc | 2100 |
| tgcaatttat ttgaaaaatt cttccccagc agttcataca aagaccagt cgggatatcc | 2160 |
| agtatggtgg aggctatggt ttccagagcc cgaattgatg cacggattga tttcgaatct | 2220 |
| ggaaggataa agaagaaga gttcactgag atcatgaaga tctgttccac cattgaagag | 2280 |
| ctcagacggc aaaaatagtg aatttagctt gtccttcatg aaaaaatgcc ttgttcctac | 2340 |
| t | 2341 |

```
<210> SEQ ID NO 15
<211> LENGTH: 2233
<212> TYPE: DNA
<213> ORGANISM: Influenza A virus

<400> SEQUENCE: 15
```

| | |
|---|---|
| agcgaaagca ggtactgatc caaaatggaa gattttgtgc gacaatgctt caatccgatg | 60 |
| attgtcgagc ttgcggaaaa acaatgaaa gagtatgggg aggacctgaa atcgaaaca | 120 |
| aacaaatttg cagcaatatg cactcacttg gaagtatgct tcatgtattc agatttccac | 180 |
| ttcatcaatg agcaaggcga gtcaataatc gtagaacttg gtgatcctaa tgcacttttg | 240 |
| aagcacagat ttgaaataat cgagggaaga gatcgcacaa tggcctggac agtagtaaac | 300 |
| agtatttgca cactacagg ggctgagaaa ccaaagtttc taccagattt gtatgattac | 360 |
| aaggaaaata gattcatcga aattggagta acaaggagag aagttcacat atactatctg | 420 |
| gaaaaggcca ataaaattaa atctgagaaa acacacatcc acattttctc gttcactggg | 480 |
| gaagaaatgg ccacaaaggc cgactacact ctcgatgaag aaagcagggc taggatcaaa | 540 |
| accaggctat tcaccataag acaagaaatg gccagcagag gcctctggga ttcctttcgt | 600 |
| cagtccgaga ggagaagaa gacaattgaa gaaggtttg aaatcacagg aacaatgcgc | 660 |
| aagcttgccg accaaagtct cccgccgaac ttctccagcc ttgaaaattt tagagcctat | 720 |
| gtggatggat tcgaaccgaa cggctacatt gagggcaagc tgtctcaaat gtccaaagaa | 780 |
| gtaaatgcta gaattgaacc ttttttgaaa acaacaccac gaccacttag acttccgaat | 840 |
| gggcctccct gttctcagcg gtccaaattc ctgctgatgg atgccttaaa attaagcatt | 900 |
| gaggacccaa gtcatgaagg agagggaata ccgctatatg atgcaatcaa atgcatgaga | 960 |
| acattctttg gatggaagga acccaatgtt gttaaaccac acgaaaaggg aataaatcca | 1020 |
| aattatcttc tgtcatggaa gcaagtactg gcagaactgc aggacattga gaatgaggag | 1080 |
| aaaattccaa agactaaaaa tatgaaaaaa acaagtcagc taaagtgggc acttggtgag | 1140 |
| aacatggcac cagaaaaggt agactttgac gactgtaaag atgtaggtga tttgaagcaa | 1200 |
| tatgatagtg atgaaccaga attgaggtcg cttgcaagtt ggattcagaa tgagttcaac | 1260 |
| aaggcatgcg aactgacaga ttcaagctgg atagagcttg atgagattgg agaagatgtg | 1320 |
| gctccaattg aacacattgc aagcatgaga aggaattatt tcacatcaga ggtgtctcac | 1380 |
| tgcagagcca cagaatacat aatgaagggg gtgtacatca atactgcctt acttaatgca | 1440 |

```
tcttgtgcag caatggatga tttccaatta attccaatga taagcaagtg tagaactaag   1500
gagggaaggc gaaagaccaa cttgtatggt ttcatcataa aaggaagatc ccacttaagg   1560
aatgacaccg acgtggtaaa ctttgtgagc atggagtttt ctctcactga cccaagactt   1620
gaaccacaca aatgggagaa gtactgtgtt cttgagatag gagatatgct tctaagaagt   1680
gccataggcc aggtttcaag gcccatgttc ttgtatgtga ggacaaatgg aacctcaaaa   1740
attaaaatga aatggggaat ggagatgagg cgttgtctcc tccagtcact tcaacaaatt   1800
gagagtatga ttgaagctga gtcctctgtc aaagagaaag acatgaccaa agagttcttt   1860
gagaacaaat cagaaacatg gcccattgga gagtctccca aggagtggga ggaaagttcc   1920
attgggaagg tctgcaggac tttattagca aagtcggtat ttaacagctt gtatgcatct   1980
ccacaactag aaggattttc agctgaatca agaaaactgc ttcttatcgt tcaggctctt   2040
agggacaatc tggaacctgg gacctttgat cttgggggc tatatgaagc aattgaggag   2100
tgcctaatta atgatccctg gttttgctt aatgcttctt ggttcaactc cttccttaca   2160
catgcattga gttagttgtg gcagtgctac tatttgctat ccatactgtc caaaaaagta   2220
ccttgtttct act                                                      2233

<210> SEQ ID NO 16
<211> LENGTH: 1565
<212> TYPE: DNA
<213> ORGANISM: Influenza A virus

<400> SEQUENCE: 16
agcaaaagca gggtagataa tcactcactg agtgacatca aaatcatggc gtcccaaggc     60
accaaacggt cttacgaaca gatggagact gatggagaac gccagaatgc cactgaaatc    120
agagcatccg tcggaaaaat gattggtgga attggacgat tctacatcca aatgtgcaca    180
gaacttaaac tcagtgatta tgagggacgg ttgatccaaa acagcttaac aatagagaga    240
atggtgctct ctgcttttga cgaaaggaga aataaatacc tggaagaaca tcccagtgcg    300
gggaaggatc ctaagaaaac tggaggacct atatacagaa gagtaaacgg aaagtggatg    360
agagaactca tcctttatga caaagaagaa ataaggcgaa tctggcgcca agctaataat    420
ggtgacgatg caacggctgg tctgactcac atgatgatct ggcattccaa tttgaatgat    480
gcaacttatc agaggacaag ggctcttgtt cgcaccggaa tggatccag gatgtgctct    540 ctgatgcaag gttcaactct ccctaggagg tctggagccg caggtgctgc agtcaaagga    600 gttgaacaa tggtgatgga attggtcagg atgatcaaac gtgggatcaa tgatcggaac    660
ttctggaggg gtgagaatgg acgaaaaaca agaattgctt atgaaagaat gtgcaacatt    720
ctcaaaggga aatttcaaac tgctgcacaa aaagcaatga tggatcaagt gagagagagc    780
cgggacccag ggaatgctga gttcgaagat ctcactttc tagcacggtc tgcactcata    840
ttgagagggt cggttgctca caagtcctgc ctgcctgcct gtgtgtatgg acctgccgta    900
gccagtgggt acgactttga aagagggga tactctctag tcggaataga ccctttcaga    960
ctgcttcaaa acagccaagt gtacagccta atcagaccaa atgagaatcc agcacacaag   1020
agtcaactgg tgtggatggc atgccattct gccgcatttg aagatctaag agtattgagc   1080
ttcatcaaag ggacgaaggt ggtcccaaga gggaagcttt ccactagagg agttcaaatt   1140
gcttccaatg aaaatatgga gactatggaa tcaagtacac ttgaactgag aagcaggtac   1200
tgggccataa ggaccagaag tggaggaaac accaatcaac agagggcatc tgcgggccaa   1260
```

| | |
|---|---|
| atcagcatac aacctacgtt ctcagtacag agaaatctcc cttttgacag aacaaccgtt | 1320 |
| atggcagcat tcactgggaa tacagagggg agaaacatctg acatgaggac cgaaatcata | 1380 |
| aggatgatgg aaagtgcaag accagaagat gtgtctttcc aggggcgggg agtcttcgag | 1440 |
| ctctcggacg aaaaggcagc gagcccgatc gtgccttcct ttgacatgag taatgaagga | 1500 |
| tcttatttct tcggagacaa tgcagaggag tacgacaatt aaagaaaaat accccttgttt | 1560 |
| ctact | 1565 |

<210> SEQ ID NO 17
<211> LENGTH: 1027
<212> TYPE: DNA
<213> ORGANISM: Influenza A virus

<400> SEQUENCE: 17

| | |
|---|---|
| agcgaaagca ggtagatatt gaaagatgag tcttctaacc gaggtcgaaa cgtacgttct | 60 |
| ctctatcatc ccgtcaggcc ccctcaaagc cgagatcgca cagagacttg aagatgtctt | 120 |
| tgcagggaag aacaccgatc ttgaggttct catggaatgg ctaaagacaa gaccaatcct | 180 |
| gtcacctctg actaagggga ttttaggatt tgtgttcacg ctcaccgtgc ccagtgagcg | 240 |
| aggactgcag cgtagacgct ttgtccaaaa tgcccttaat gggaacgggg atccaaataa | 300 |
| catggacaaa gcagttaaac tgtataggaa gctcaagagg gagataacat tccatggggc | 360 |
| caaagaaatc tcactcagtt attctgctgg tgcacttgcc agttgtatgg gcctcatata | 420 |
| caacaggatg ggggctgtga ccactgaagt ggcatttggc ctggtatgtg caacctgtga | 480 |
| acagattgct gactcccagc atcggtctca taggcaaatg gtgacaacaa ccaacccact | 540 |
| aatcagacat gagaacagaa tggttttagc cagcactaca gctaaggcta tggagcaaat | 600 |
| ggctggatcg agtgagcaag cagcagaggc catggaggtt gctagtcagg ctaggcaaat | 660 |
| ggtgcaagcg atgagaacca ttgggactca tcctagctcc agtgctggtc tgaaaaatga | 720 |
| tcttcttgaa aatttgcagg cctatcagaa acgaatgggg gtgcagatgc aacggttcaa | 780 |
| gtgatcctct cgctattgcc gcaaatatca ttgggatctt gcacttgata ttgtggattc | 840 |
| ttgatcgtct ttttttcaaa tgcatttacc gtcgctttaa atacgactg aaaggagggc | 900 |
| cttctacgga aggagtgcca aagtctatga gggaagaata tcgaaggaa cagcagagtg | 960 |
| ctgtggatgc tgacgatggt cattttgtca gcatagagct ggagtaaaaa actaccttgt | 1020 |
| ttctact | 1027 |

<210> SEQ ID NO 18
<211> LENGTH: 890
<212> TYPE: DNA
<213> ORGANISM: Influenza A virus

<400> SEQUENCE: 18

| | |
|---|---|
| agcaaaagca gggtgacaaa gacataatgg atccaaacac tgtgtcaagc tttcaggtag | 60 |
| attgctttct ttggcatgtc cgcaaacgag ttgcagacca agaactaggt gatgccccat | 120 |
| tccttgatcg gcttcgccga gatcagaaat ccctaagagg aaggggcagc actcttggtc | 180 |
| tggacatcga gacagccaca cgtgctggaa agcagatagt ggagcggatt ctgaaagaag | 240 |
| aatccgatga ggcacttaaa atgaccatgg cctctgtacc tgcgtcgcgt tacctaaccg | 300 |
| acatgactct tgaggaaatg tcaagggaat ggtccatgct catacccaag cagaaagtgg | 360 |
| caggccctct tgtatcaga atggaccagg cgatcatgga taaaaacatc atactgaaag | 420 |
| cgaacttcag tgtgattttt gaccggctgg agactctaat attgctaagg ctttcaccg | 480 |

| | |
|---|---|
| aagagggagc aattgttggc gaaatttcac cattgccttc tcttccagga catactgctg | 540 |
| aggatgtcaa aaatgcagtt ggagtcctca tcggaggact tgaatggaat gataacacag | 600 |
| ttcgagtctc tgaaactcta cagagattcg cttggagaag cagtaatgag aatgggagac | 660 |
| ctccactcac tccaaaacag aaacgagaaa tggcgggaac aattaggtca gaagtttgaa | 720 |
| gaaataagat ggttgattga agaagtgaga cacaaactga aggtaacaga aatagttttt | 780 |
| gagcaaataa catttatgca agccttacat ctattgcttg aagtggagca agagataaga | 840 |
| actttctcat ttcagcttat ttaataataa aaaacaccct tgtttctact | 890 |

<210> SEQ ID NO 19
<211> LENGTH: 2341
<212> TYPE: DNA
<213> ORGANISM: Influenza A virus

<400> SEQUENCE: 19

| | |
|---|---|
| agcaaaagca ggtcaattat attcagtatg gaaagaataa agaactacg gaacctgatg | 60 |
| tcgcagtctc gcactcgcga gatactgaca aaaccacag tggaccatat ggccataatt | 120 |
| aagaagtaca catcggggag acaggaaaag aacccgtcac ttaggatgaa atggatgatg | 180 |
| gcaatgaaat acccaatcac tgctgacaaa aggataacag aaatggttcc ggagagaaat | 240 |
| gaacaaggac aaactctatg gagtaaaatg agtgatgctg gatcagatcg agtgatggta | 300 |
| tcacctttgg ctgtaacatg gtggaataga atggaccccg tggcaagtac ggtccattac | 360 |
| ccaaaagtat acaagactta ttttgacaaa gtcgaaaggt taaaacatgg aacctttggc | 420 |
| cctgttcatt ttagaaatca agtcaagata cgcagaagag tagacataaa ccctggtcat | 480 |
| gcagacctca gtgccaaaga ggcacaagat gtaattatgg aagttgtttt tcccaatgaa | 540 |
| gtgggagcca ggatactaac atcagaatcg caattaacaa taactaaaga gaaaaaagaa | 600 |
| gaactccgag attgcaaaat ttctcccttg atggttgcat acatgttaga gagagaactt | 660 |
| gtccgaaaaa caagatttct cccagttgct ggcggaacaa gcagtatata cattgaagtc | 720 |
| ttacatttga ctcaaggaac gtgttgggaa caaatgtaca ctccaggtgg agaagtgagg | 780 |
| aatgacgatg ttgaccaaag cctaattatt gcggccagga catagtaag aagagctgca | 840 |
| gtatcagcag atccactagc atcttttattg gagatgtgcc acagcacaca aattggcggg | 900 |
| acaaggatgg tggacattct tagacagaac ccgactgaag aacaagctgt ggatatatgc | 960 |
| aaggctgcaa tgggattgag aatcagctca tccttcagct ttggtgggtt tacatttaaa | 1020 |
| agaacaagcg gtcatcagt caaaaaagag gaagaagtgc ttacaggcaa tctccaaaca | 1080 |
| ttgaagataa gagtacatga ggggtatgag gagttcacaa tggtggggaa agagcaaca | 1140 |
| gctatactca gaaaagcaac cagaagattg gttcagctca tagtgagtgg aagagacgaa | 1200 |
| cagtcaatag ccgaagcaat aatcgtggcc atggtgtttt cacaagagga ttgcatgata | 1260 |
| aaagcagtta gaggtgacct gaatttcgtc aacagagcaa atcaacggtt gaaccccatg | 1320 |
| catcagcttt taaggcattt tcagaaagat gcgaaagtgc ttttcaaaa ttggggaatt | 1380 |
| gaacacatcg acagtgtgat gggaatggtt ggagtattac cagatatgac tccaagcaca | 1440 |
| gagatgtcaa tgagaggaat aagagtcagc aaaatgggtg tggatgaata ctccagtaca | 1500 |
| gagagggtgg tggttagcat tgatcggttt ttgagagttc agaccaacg cgggaatgta | 1560 |
| ttattgtctc ctgaggaggt cagtgaaaca cagggaactg aaagattgac aataacatat | 1620 |
| tcatcgtcga tgatgtggga gattaacggt cctgagtcgg ttttggtcaa tacctatcaa | 1680 |

-continued

```
tggatcatca gaaattggga agctgtcaaa attcaatggt ctcagaatcc tgcaatgttg    1740
tacaacaaaa tggaatttga accatttcaa tctttagtcc caaggccat  tagaagccaa    1800 tacagtgggt tgtcagaac tctattccaa caaatgagag acgtacttgg gacatttgac    1860
accacccaga taataaagct tctcccttt  gcagccgctc caccaaagca aagcagaatg    1920
cagttctctt cactgactgt aaatgtgagg ggatcaggga tgagaatact tgtaagggc    1980 aattctcctg tattcaacta caacaagacc actaaaagac taacaattct cggaaaagat    2040
gccggcactt taattgaaga cccagatgaa agcacatccg gagtggagtc cgccgtcttg    2100
agagggtttc tcattatagg taaggaagac agaagatacg gaccagcatt aagcatcaat    2160
gaactgagta accttgcaaa aggggaaaag gctaatgtgc taatcgggca aggagacgtg    2220
gtgttggtaa tgaaacgaaa acgggactct agcatactta ctgacagcca gacagcgacc    2280
aaaagaattc ggatggccat caattaatgt tgaatagttt aaaaacgacc ttgtttctac    2340
t                                                                    2341

<210> SEQ ID NO 20
<211> LENGTH: 2341
<212> TYPE: DNA
<213> ORGANISM: Influenza A virus

<400> SEQUENCE: 20
agcaaaagca ggcaaaccat ttgaatggat gtcaatccga ctctactgtt cctaaaggtt      60
ccagcgcaaa atgccataag caccacattc ccttatactg agatcctcc  atacagccat    120 ggaacaggaa caggatacac catggacaca gtcaacagaa cacccaata  ttcagagaag    180 gggaagtgga cgacaaatac agaaactggg gcaccccaac tcaacccaat tgatggacca    240
ctacctgagg ataatgagcc aagtggatat gcacaaacag actgtgtcct ggaggctatg    300
gccttccttg aagaatccca cccaggtatc tttgagaact catgccttga acaatggaa     360 gtcgttcaac aaacaagggt ggacaaacta acccaaggcc gccagactta tgattggaca    420
ttaaacagaa atcaaccggc agcaactgca ttagccaaca ccatagaagt ttttagatcg    480
aatggactaa cagccaatga atcaggaagg ctaatagatt tcctcaagga tgtgatggaa    540
tcaatggata agaggaaat  ggagataaca acacactttc aaagaaaaag gagagtaaga    600
gacaacatga ccaagaaaat ggtcacacaa gaacaatag  ggaagaaaaa acaaagagtg    660
aataagagag ctatctaat  aagagctttg acattgaaca cgatgaccaa agatgcagag    720
agaggtaaat taaaagaag  ggctattgca cacccgggga tgcaaattag ggggttcgtg    780
tacttcgttg aaactttagc tagaagcatt tgcgaaaagc ttgaacagtc tggacttccg    840 gttggggta  atgaaaagaa ggccaaactg gcaaatgttg tgagaaaaat gatgactaat    900
tcacaagaca ctgagctttc tttcacaatc actggggaca cactaagtg  gaatgaaaat    960 caaaaccctc gaatgttttt ggcgatgatt acatatatca caaaaatca  acctgagtgg   1020 ttcagaaaca tcctgagcat cgcaccaata atgttctcaa acaaaatggc aagactagga   1080 aaggataca  tgttcgagag taagagaatg aagctccgaa cacaaatacc cgcagaaatg   1140
ctagcaagca ttgacctgaa gtatttcaat gaatcaacaa ggaagaaat  tgagaaaata   1200 aggcctcttc taatagatgg cacagcatca ttgagccctg gatgatgat  gggcatgttc   1260 aacatgctaa gtacggtttt aggagtctcg gtactgaatc ttgggcaaaa gaaatacacc   1320 aagacaaacat actggtggga tgggctccaa tcctccgacg atttgccct  catagtgaat   1380 gcaccaaatc atgagggaat acaagcagga gtggatagat tctacaggac ctgcaagtta   1440
```

-continued

```
gtgggaatca acatgagcaa aaagaagtcc tatataaata aaacagggac atttgaattc   1500
acaagctttt tttatcgata tggatttgtg gctaatttta gcatggagct tcccagtttt   1560
ggagtgtctg gaataaacga gtcagctgat atgagtattg gagtaacagt gataaagaac   1620
aacatgataa acaatgacct tgggccagca acagcccaga tggctctcca attgttcatc   1680
aaagactaca gatatacata taggtgccat agaggagaca cacaaattca gacgagaaga   1740
tcattcgagc taaagaagct gtgggatcaa acccaatcaa gggcaggact attggtatca   1800
gatgggggac caaacttata caatatccgg aaccttcaca tccctgaagt ctgcttaaag   1860
tgggagctaa tggatgagaa ttatcgggga agactttgta accccctgaa tccctttgtc   1920
agccataaag aaattgagtc tgtaaacaat gctgtagtga tgccagccca cggtccagcc   1980
aaaagtatgg aatatgatgc cgttgcaact acacactcct ggaatcccaa gaggaaccgc   2040
tctattctaa acactagcca aaggggaatt cttgaggatg aacagatgta ccaaaagtgc   2100
tgcaacttgt tcgagaaatt tttccctagt agttcatata ggagaccgat tggaatttct   2160
agcatggtgg aggccatggt gtctagggcc cggattgatg ccagaattga cttcgagtct   2220
ggacggatta agaaggaaga gttctctgag atcatgaaga tctgttccac cattgaagaa   2280
ctcagacggc aaaaataatg aatttagctt gtccttcatg aaaaaatgcc ttgtttctac   2340
t                                                                   2341
```

```
<210> SEQ ID NO 21
<211> LENGTH: 2233
<212> TYPE: DNA
<213> ORGANISM: Influenza A virus

<400> SEQUENCE: 21
agcaaaagca ggtactgatt cgaaatggaa gattttgtgc gacaatgctt caacccgatg     60
attgtcgaac ttgcagaaaa agcaatgaaa gagtatggag aggatctgaa aattgaaaca    120
aacaaatttg cagcaatatg cacccacttg gaggtatgtt tcatgtattc agattttcat    180
ttcatcaatg aacaaggcga atcaatagtg gtagaacttg atgatccaaa tgcactgtta    240
aagcacagat ttgaaataat cgaggggaga gacagaacaa tggcctggac agtagtaaac    300
agtatctgca acactactgg agcagaaaaa ccaaagtttc taccagattt gtatgattac    360
aaggagaata gattcatcga aattggagtg acaagaagag aagtccacat atattacctt    420
gaaaaggcca ataaaattaa atctgagaac acacacattc acatcttctc attcactggg    480
gaggaaatag ccacaaaggc agactacact ctcgacgagg aaagcagggc taggattaaa    540
accaggctat ttaccataag acaagaaatg gccaacagag gcctctggga ttcctttcgt    600
cagtccgaaa gaggcgaaga aacaattgaa gaaaaatttg aaatctcagg aactatgcgt    660
aggcttgccg accaaagtct cccaccgaaa ttctcctgcc ttgagaattt tagagcctat    720
gtggatggat tcgaaccgaa cggctgcatt gagggcaagc tttctcaaat gtccaaagaa    780
gtgaatgcca aaattgaacc ttttctgaag acaacaccaa gaccaatcaa acttcctaat    840
ggacctcctt gttatcagcg gtccaaattc ctcctgatgg atgctttgaa attgagcatt    900
gaagacccaa gtcatgaagg agaagggatt ccattatatg atgcgatcaa gtgcataaaa    960
acattctttg gatggaaaga accttatata gtcaaaccac acgaaaaggg aataaattca   1020
aattacctgc tgtcatggaa gcaagtattg tcagaattgc aggacattga aaatgaggag   1080
aagatcccaa ggactaaaaa catgaagaaa acgagtcaac taaagtgggc tcttggtgaa   1140
```

-continued

```
aacatggcac cagagaaagt agactttgac aactgcagag acataagcga tttgaagcaa      1200
tatgatagtg acgaacctga attaaggtca ctttcaagct ggatacagaa tgagttcaac      1260
aaggcctgcg agctaactga ttcaatctgg atagagctcg atgaaattgg agaggacgta      1320
gccccaattg agtacattgc aagcatgagg aggaattatt tcacagcaga ggtgtcccat      1380
tgtagagcca ctgagtacat aatgaagggg gtatacatta atactgccct gctcaatgca      1440
tcctgtgcag caatggacga ttttcaacta attcccatga taagcaagtg cagaactaaa      1500
gagggaaggc gaaaaaccaa tttatatgga ttcatcataa agggaagatc tcatttaagg      1560
aatgacacag atgtggtaaa ctttgtgagc atggagtttt ctctcactga cccgagactt      1620
gagccacata atgggagaaa atactgtgtc cttgagatag agatatgtt actaagaagt       1680 gccataggcc aaatttcaag gcctatgttc ttgtatgtga ggacaaacgg aacatcaaag      1740
gtcaaaatga atgggaat ggagatgaga cgttgcctcc ttcagtcact ccagcagatc        1800
gagagcatga ttgaagccga gtcctcgatt aaagagaaag acatgaccaa agagtttttt      1860
gagaataaat cagaagcatg gcccattggg gagtccccca agggagtgga agaaggttcc      1920
attgggaaag tctgtaggac tctattggct aagtcagtgt tcaatagcct gtatgcatca      1980
ccacaattgg aaggattttc agcggagtca agaaaactgc ttcttgttgt tcaggctctt      2040
agggacaacc tcgaacctgg gacctttgat ctcgggggc tatatgaagc aattgaggag       2100
tgcctgatta atgatccctg gttttgctc aatgcatctt ggttcaactc cttcctgaca       2160
catgcattaa atagttatg gcagtgctac tatttgttat ccgtactgtc caaaaaagta      2220
ccttgtttct act                                                         2233
```

<210> SEQ ID NO 22
<211> LENGTH: 1566
<212> TYPE: DNA
<213> ORGANISM: Influenza A virus

<400> SEQUENCE: 22

```
agcaaaagca gggttaataa tcactcaccg agtgacatca aaatcatggc gtcccaaggc       60
accaaacggt cttatgaaca gatggaaact gatgggatc gccagaatgc aactgagatt       120
agggcatccg tcgggaagat gattgatgga attgggagat tctacatcca aatgtgcact      180
gaacttaaac tcagtgatca tgaagggcgg ttgatccaga acagcttgac aatagagaaa      240
atggtgctct ctgcttttga tgaaagaagg aataaatacc tggaagaaca ccccagcgcg      300
gggaaagatc ccaagaaaac tggggggccc atatacagga gagtagatgg aaaatggatg      360
agggaactcg tcctttatga caaagaagag ataaggcgaa tctggcgcca agccaacaat      420
ggtgaggatg cgacagctgg tctaactcac ataatgatct ggcattccaa tttgaatgat      480
gcaacatacc agaggacaag agctcttgtt cgaactggaa tggatcccag aatgtgctct      540
ctgatgcagg gctcgactct ccctagaagg tccggagctg caggtgctgc agtcaaagga      600
atcgggacaa tggtgatgga actgatcaga atggtcaaac ggggatcaa cgatcgaaat      660 ttctggagag gtgagaatgg gcggaaaaca agaagtgctt atgagagaat gtgcaacatt      720
cttaaaggaa aatttcaaac agctgcacaa agagcaatgg tggatcaagt gagagaaagt      780
cggaacccag gaaatgctga gatcgaagat ctcatatttt ggcaagatc tgcattgata      840 ttgagagggt cagttgctca caaatcttgc ctacctgcct gtgcgtatgg acctgcagta      900
tccagtgggt acgacttcga aaagagggga tattccttgg tgggaataga ccctttcaaa      960
ctacttcaaa atagccaaat atacagccta atcagaccta acgagaatcc agcacacaag      1020
```

| | | | |
|---|---|---|---|
| agtcagctgg | tgtggatggc atgccattct gctgcatttg aagatttaag attgttaagc | 1080 |
| ttcatcagag | ggacaaaagt atctccgcgg gggaaactgt caactagagg agtacaaatt | 1140 |
| gcttcaaatg | agaacatgga taatatggga tcgagcactc ttgaactgag aagcgggtac | 1200 |
| tgggccataa | ggaccaggag tggaggaaac actaatcaac agagggcctc cgcaggccaa | 1260 |
| accagtgtgc | aacctacgtt ttctgtacaa agaaacctcc catttgaaaa gtcaaccatc | 1320 |
| atggcagcat | tcactggaaa tacgagggga aggacttcag acatgagggc agaaatcata | 1380 |
| agaatgatgg | aaggtgcaaa accagaagaa gtgtcattcc gggggagggg agttttcgag | 1440 |
| ctctcagacg | agaaggcaac gaacccgatc gtgccctctt tgatatgaga taatgaagga | 1500 |
| tcttatttct | tcggagacaa tgcagaagag tacgacaatt aaggaaaaaa taccccttgtt | 1560 |
| tctact | | 1566 |

<210> SEQ ID NO 23
<211> LENGTH: 1027
<212> TYPE: DNA
<213> ORGANISM: Influenza A virus

<400> SEQUENCE: 23

| | | | |
|---|---|---|---|
| agcaaaagca | ggtagatatt gaaagatgag ccttctaacc gaggtcgaaa cgtatgttct | 60 |
| ctctatcgtt | ccatcaggcc ccctcaaagc cgagatcgcg cagagacttg aagatgtctt | 120 |
| tgctgggaaa | aacacagatc ttgaggctct catggaatgg ctaaagacaa gaccaattct | 180 |
| gtcacctctg | actaagggga ttttggggtt tgtgttcacg ctcaccgtgc ccagtgagcg | 240 |
| aggactgcag | cgtagacgct ttgtccaaaa tgccctcaat gggaatggag atccaaataa | 300 |
| catggacaaa | gcagttaaac tgtataggaa acttaagagg gagataacgt tccatggggc | 360 |
| caaagaaata | gctctcagtt attctgctgg tgcacttgcc agttgcatgg gcctcatata | 420 |
| caataggatg | ggggctgtaa ccactgaagt ggcatttggc ctggtatgtg caacatgtga | 480 |
| acagattgct | gactcccagc acaggtctca taggcaaatg gtggcaacaa ccaatccatt | 540 |
| aataaaacat | gagaacagaa tggttttggc cagcactaca gctaaggcta tggagcaaat | 600 |
| ggctggatca | agtgagcagg cagcggaggc catggaaatt gctagtcagg ccaggcaaat | 660 |
| ggtgcaggca | atgagagccg ttgggactca tcctagctcc agtactggtc taagagatga | 720 |
| tcttcttgaa | aatttgcaga cctatcgaaa acgaatgggg gtgcagatgc aacgattcaa | 780 |
| gtgacccgct | tgttgttgcc gcgagtatca ttgggatctt gcacttgata ttgtggattc | 840 |
| ttgatcgtct | tttttcaaa tgcgtctatc gactcttcaa acacggcctt aaaagaggcc | 900 |
| cttctacgga | aggagtacct gagtctatga gggaagaata tcgaaaggaa cagcagaatg | 960 |
| ctgtggatgc | tgacgacagt catttgtca gcatagagtt ggagtaaaaa actaccttgt | 1020 |
| ttctact | | 1027 |

<210> SEQ ID NO 24
<211> LENGTH: 890
<212> TYPE: DNA
<213> ORGANISM: Influenza A virus

<400> SEQUENCE: 24

| | | | |
|---|---|---|---|
| agcaaaagca | gggtgacaaa gacataatgg attccaacac tgtgtcaagt ttccaggtag | 60 |
| attgctttct | ttggcatatc cggaaacaag ttgtagacca agaactgagt gatgccccat | 120 |
| tccttgatcg | gcttcgccga gatcagaggt ccctaagggg aagaggcaat actctcggtc | 180 |

| | |
|---|---|
| tagacatcaa agcagccacc catgttggaa agcaaattgt agaaaagatt ctgaaagaag | 240 |
| aatctgatga ggcacttaaa atgaccatgg tctccacacc tgcttcgcga tacataactg | 300 |
| acatgactat tgaggaattg tcaagaaact ggttcatgct aatgcccaag cagaaagtgg | 360 |
| aaggacctct ttgcatcaga atggaccagg caatcatgga gaaaacatc atgttgaaag | 420 |
| cgaatttcag tgtgattttt gaccgactag agaccatagt attactaagg ctttcaccg | 480 |
| aagagggagc aattgttggc gaaatctcac cattgccttc ttttccagga catactattg | 540 |
| aggatgtcaa aaatgcaatt ggggtcctca tcggaggact tgaatggaat gataacacag | 600 |
| ttcgagtctc taaaaatcta cagagattcg cttggagaag cagtaatgag atgggggac | 660 |
| ctccacttac tccaaaacag aaacggaaaa tggcgagaac agctaggtca aaagtttgaa | 720 |
| gagataagat ggctgattga agaagtgaga cacagactaa aacaactga aaatagcttt | 780 |
| gaacaaataa cattcatgca agcattacaa ctgctgtttg aagtggaaca ggagataaga | 840 |
| actttctcat ttcagcttat ttaatgataa aaaacaccct tgtttctact | 890 |

<210> SEQ ID NO 25
<211> LENGTH: 2341
<212> TYPE: DNA
<213> ORGANISM: Influenza A virus

<400> SEQUENCE: 25

| | |
|---|---|
| agcaaaagca ggtcaattat attcaatatg gaaagaataa agaactaag agatctaatg | 60 |
| tcgcagtccc gcactcgcga gatactaaca aaaccactg tggatcatat ggccataatc | 120 |
| aagaaataca catcaggaag acaagagaag aaccctgctc tcagaatgaa atggatgatg | 180 |
| gcaatgaaat atccaatcac agcagacaag agaataatgg agatgattcc tgaaaggaat | 240 |
| gagcaaggac aaacgctttg agcaagaca atgatgctg gtcggacag agtgatggtg | 300 |
| tctcccctag ctgtaacttg gtggaacagg aatgggccga caacaagtac agtccattat | 360 |
| ccaaaggttt acaaaacata ctttgagaag gttgaaaggt taaacatgg aaccttcggt | 420 |
| cccgttcatt tccgaaacca agttaaaata cgtcgccggg tggatataaa cccgggccat | 480 |
| gcagatctca gtgctaaaga agcacaagat gttatcatgg aggtcgtttt cccaaatgaa | 540 |
| gtgggagcta gaatattgac atcagagtcg caattgacaa taacaaaaga gaagaaagaa | 600 |
| gagctccagg attgtaaaat tgctccttta atggtggcat acatgttgga agagaactg | 660 |
| gtccgcaaaa ccagatttct accggtagca ggcggaacaa gcagtgtgta cattgaggta | 720 |
| ttgcatttga ctcaagggac ctgttgggaa cagatgtaca ctcccggcgg agaagtaaga | 780 |
| aatgatgatg ttgaccagag tttgatcatc gctgccagaa acattgttag agagcaaca | 840 |
| gtatcagcgg acccactggc atcactcttg gagatgtgtc acagcacaca aattggggga | 900 |
| ataaggatgg tggacatcct taggcaaaac ccaactgagg agcaagctgt ggatatatgc | 960 |
| aaagcagcaa tgggtttgag gatcagttca tcctttagct ttggaggctt cactttcaaa | 1020 |
| agaacaaatg gatcatccgt caagaaggaa gaggaagtgc ttacaggcaa cctccaaaca | 1080 |
| ttgaaaataa agtacatga ggggtatgaa gaattcacaa tggttgggcg gagagcaaca | 1140 |
| gctatcctga ggaaagcaac tagaaggctg attcagttga tagtaagtgg aagagatgaa | 1200 |
| caatcaatcg ctgaagcgat cattgtagca atggtgttct cacaggagga ttgcatgata | 1260 |
| aaggcagtcc gaggcgatct gaatttcgtg aacagagcaa accaaagatt gaaccccatg | 1320 |
| catcaactcc tgaggcactt ccaaaaagat gcaaaagtgc tgtttcagaa ctggggaatt | 1380 |
| gaacctattg acaatgtcat ggggatgatc ggaatattac ctgacatgac tccaagcgca | 1440 |

```
gagatgtcac tgagaggagt gagagttagt aagatgggag tagatgaata ttccagcacg    1500
gagagagtgg tggtgagtat tgaccgtttc ttgagggtcc gagatcagca ggggaacgta    1560
ctcttatctc ctgaagaggt tagtgaaaca cagggaacag agaagttgac aataacatat    1620
tcatcctcaa tgatgtggga atcaacggt cctgagtcag tgcttgttaa cacttatcaa     1680
tggatcatca ggaattggga gactgtaaag attcaatggt ctcaagatcc cacaatgctg    1740
tacaataaga tggagtttga atcgttccaa tccttggtgc aaaggctgc cagaagccaa     1800 tatagtggat ttgtgagaac actattccaa cagatgcgtg atgttttggg gacatttgat    1860
actgtccaaa taatcaagct gctaccattt gcagcagccc caccggagcc gagcagaatg    1920
cagttttctt ctctaactgt gaatgtgaga ggctcaggaa tgagaatact cgtgagggt     1980 aactcccccg tgttcaacta caacaaggca accaaaaggc ttacagtcct cggaaaggac    2040
gcaggtgcat aacagaaga tccagacgag ggaacagccg gggtggaatc tgcagtattg     2100 agggggattcc taattctagg cagagaggac aaaagatatg acccgcatt gagcatcaat    2160 gaactgagca atcttgcaaa aggggagaag gctaatgtat tgataatgca aggagacgtg    2220
gtgttggtaa tgaaacggaa acgggacttt agcatactta ctgacagcca gacagcgacc    2280
aaaagaattc ggatggccat caattagtgt tgaatagttt aaaaacgacc ttgtttctac    2340
t                                                                    2341

<210> SEQ ID NO 26
<211> LENGTH: 2341
<212> TYPE: DNA
<213> ORGANISM: Influenza A virus

<400> SEQUENCE: 26
agcaaaagca ggcaaaccat ttgaatggat gtcaatccga ctttactttt cttaaaagtg     60
ccagcgcaaa atgctataag taccacattc ccttatactg gagatcctcc atacagccat    120
ggaacaggaa caggatacac catggacaca gtcaacagaa cacatcaata ttcagaaaag    180
gggaaatgga caacgaacac agagactgga gcaccccaac tcaatccgat tgatggacca    240
ctacctgagg ataatgagcc gagtgggtat gcacaaacag attgtgtatt ggaagcaatg    300
gctttccttg aagaatccca cccagggatc tttgaaaact cgtgtcttga acgatggaa    360 gttgttcagc aaacaagagt ggataagctg acccaaggtc gccaaaccta tgactggaca    420
ttgaaaagaa ccagccggc tgcaaccgct ttggccaaca ctatagaggt cttcagatcg    480
aatggtctaa cagccaatga atcgggaagg ctaatagatt tcctcaaaga cgtgatggaa    540
tcaatggata agggaagaat ggaataata acacatttcc agagaaagag aagagtgagg    600
gacaacatga ccaagaaaat ggtcacacaa gaacaatag ggagaaaaa acaaaggctg     660 aacaaaagga gctacctaat aagagcactg acactgaaca caatgacaaa agacgcagaa    720
agaggcaaat tgaagaggcg ggcaattgca cacccggga tgcaaatcag aggattcgtg     780
tactttgtcg aaacactagc gaggagtatc tgtgagaaac ttgagcaatc tggactcccc    840
gtcggaggga tgaaaagaa ggctaaattg gcaaatgtcg tgaggaagat gatgactaac    900
tcacaagata cagagctctc ttttacaatt actggagaca cacaaatg gaatgagaat     960 cagaaccctc ggatgtttct agcaatgata acatacatca aaggaaccaa acctgaatgg    1020
tttagaaatg tcttaagcat tgctcctata atgttctcaa acaagatggc aagattaggg    1080
aaaggataca tgttcgaaag taagagcatg aagctacgga cacaaatacc agcagaaatg    1140
```

```
cttgcaagca ttgacttgaa atacttcaac gaatcaacga gaaagaaaat cgagaaaata   1200
agacctctac taatagatgg cacagcctca ttgagtcctg aatgatgat gggcatgttc    1260 aatatgctga gtacagtctt aggagtttca atcctgaatc ttgggcagaa gaggtacacc   1320
aaaaccacat actggtggga cggactccaa tcctctgatg atttcgctct catagtgaat   1380
gcaccaaatc atgagggaat agaagcaggg gtggataggt tctataggac ttgcaaacta   1440
gttggaatca atatgaccaa gaagaagtct tacataaatc ggacaggaac atgtgaattc   1500
acaagcttct tctaccgcta tgggttcgta gccaacttca gtatggagct gcccagcttt   1560
ggagtgtctg ggattaatga atcggctgac atgagcattg gtgttacagt gataaagaac   1620
aatatgatgg acaacgacct tggaccagca acagctcaga tggctcttca gctattcatt   1680
aaggactaca gatacccata ccgatgccac agggggata cacaaatcca acgaggaga    1740 tcattcgagc tgaagaagct gtgggagcag acccgctcaa aggcaggact gttggtttca   1800
gatggaggac aaacccata caatatccgg aatctccaca ttccggaggc tggcttgaag   1860
tgggaattga tggatgaaga ctaccaggc agactgtgta atcctctgaa cccgtttgtt    1920
agtcataagg aaattgagtc tgtcaacaat gctgtggtaa tgccagctca tggcccagcc   1980
aagagcatgg aatatgatgc agttgcgact acacattcat ggattcccaa gaggaatcgt   2040
tccattctca acaccagcca aaggggatt cttgaggatg aacagatgta tcagaagtgc    2100
tgcaatctat tcgagaaatt cttccctagc agttcatatc ggaggccagt tggaatttcc   2160
agcatggtgg aggccatggt gtctagggcc cgaattgatg cacgaattga cttcgagtct   2220
ggaaggatta gaaagaaga gtttgctgag atcatgaaga tctgttccac cattgaagag   2280
ctcggacggc aaaaatagtg aatttagctt gtccttcatg aaaaaatgcc ttgtttctac   2340
t                                                                  2341

<210> SEQ ID NO 27
<211> LENGTH: 2233
<212> TYPE: DNA
<213> ORGANISM: Influenza A virus

<400> SEQUENCE: 27
agcaaaagca ggtactgatc caaaatggaa gactttgtgc gacaatgctt caatccaatg    60
attgtcgagc ttgcggaaaa ggcaatgaaa gaatatgggg aagatccgaa atcgaaacg    120 aacaaatttg ccgcaatatg cacgcactta gaagtctgtt tcatgtattc agatttccac   180
tttattgatg aacggggcga atcaacaatt atagaatctg gcgatcccaa tgcattattg   240
aaacaccggt ttgaaataat cgaagggagg gaccgaacaa tggcctggac agtggtgaat   300
agtatctgca acaccacagg agttgagaag cctaaattc tcccagattt gtatgactac    360
aaggagaacc gatttattga aattggagtg acacggaggg aagttcacac atactatcta   420
gaaaaagcca caagataaa atctgagaag acacacattc acatattctc attcactgga    480
gaggaaatgg ccaccaaagc ggactacacc cttgatgaag aaagcagggc ccgaatcaaa    540
accaggctgt tcactataag gcaggaaatg ccagtaggg gtttatggga ttcctttcgt     600
cagtccgaga gaggcgaaga gacagttgaa gaaagatttg aaatcacagg gactatgtgc    660
aggcttgccg accaaagtct cccacctaat ttctccagcc ttgaaaaatt tagagcctat    720
gtggatggat tcgaaccgaa cggctgcatt gagggcaagc tttctcaaat gtcgaaagaa    780
gtaaacgcca gaattgagcc atttctgaag acaacaccac gccctcttag attacctgat    840
gggcctccct gctctcagcg gtcgaagttt ttgctgatgg atgcccttaa attaagcatc    900
```

```
gaagacccga gtcatgaggg ggagggggata ccgctatatg atgcaatcaa atgcatgaaa    960
acatttttcg gctggaaaga gcccaacatt gtaaaaccac atgaaaaagg cataaacccc   1020
aattacctcc tggcttggaa gcaggtgctg gcagagctcc aagatattga aaacgaggag   1080
aaaattccaa agacaaagaa catgaggaaa acaagccaat tgaagtgggc acttggtgag   1140
aatatggcac cagagaaagt agactttgag gattgcaaag atgttagcga tctaaggcag   1200
tatgacagtg atgaaccaaa gcctagatca ctagcaagct ggatccagag tgaattcaac   1260
aaggcatgcg aattgacaga ttcaagttgg attgaacttg atgaaatagg ggaagacgtt   1320
gctccaattg agcacattgc aagtatgaga aggaactatt tcacagcgga agtatcccat   1380
tgcagggcta ctgaatacat aatgaaggga gtgtacataa acacagcttt gttgaatgca   1440
tcctgtgcag ccatggatga cttccaactg atcccaatga taagcaaatg cagaaccaaa   1500
gaaggaagac ggaaaactaa cctgtatgga ttccttataa aaggaagatc ccatttgaga   1560
aatgacaccg atgtggtaaa ctttgtgagt atggaattct ctcttactga tccgaggctg   1620
gagccacaca gatgggaaaa gtactgcgtt cttcggatag agacatgct cttacggact   1680
gaaataggcc aagtgtcaag gcccatgttt ctttatgtga aaccaatgg aacctccaag   1740
atcaagatga atggggcat ggaaatgagg cgatgccctt ttcaatccct tcaacagatt   1800
gagagcatga ttgaggccga gtcttctgtc aaagaaaaag acatgactaa agaattcttt   1860
gaaaacaaat cagaaacatg gccaattgga gaatcaccca agggagtgga ggaaggctcc   1920
atcgggaagt gtgcagaac cttactggct aaatctgttt tcaacagtct atatgcatct   1980
ccacaactcg agggggttttc agctgaatca agaaaattgc ttctcattgt tcaggcactt   2040
agggacaacc tggaacctgg aaccttcgat cttggggggc tatatgaagc aattgaggag   2100
tgcctgatta atgatccctg gtttttgctt aatgcatctt ggttcaactc cttcctcaca   2160
catgcactaa gatagttgtg gcaatgctac tatttgctat ccatactgtc caaaaagta   2220
ccttgtttct act                                                       2233

<210> SEQ ID NO 28
<211> LENGTH: 1565
<212> TYPE: DNA
<213> ORGANISM: Influenza A virus

<400> SEQUENCE: 28
agcaaaagca gggtagataa tcactcactg agtgacatca acatcatggc gtctcagggc    60
accaaacgat cttatgaaca gatggaaact ggtggagaac gccagaatgc tactgagatc   120
agagcatctg ttggaagaat ggttggtgga attgggaggt tttatataca gatgtgcact   180
gaactcaaac tcagcgacta tgaaggaagg ctgattcaga acagcataac aatagagaga   240
atggttctct ctgcatttga tgaaggagg aacaaatacc tggaagaaca tcccagtgcg   300
gggaaggacc caaagaaaac tggaggtcca atctaccgaa gagagacgg aaaatgggtg   360
agagagctga ttctgtatga caaagaggag atcaggagaa tttggcgtca gcgaacaat   420
ggagaagatg caactgctgg tctcactcac atgatgatct ggcattccaa tctaaatgat   480
gccacatacc agagaacaag agctctcgtg cgtactggga tggaccctag aatgtgctct   540
ctgatgcaag gatcaactct cccgaggaga tctggagctg ctggtgcggc agtaaaggga   600
gtcggaacga tggtgatgga actaattcgg atgataaagc gagggattaa cgatcggaat   660
ttctggagag gtgaaaatgg gcgaagaaca agaattgcat atgagagaat gtgcaacatc   720
```

| | | |
|---|---|---|
| ctcaaaggga aattccaaac agcagcacaa agagcaatga tggatcaggt acgggaaagc | 780 | |
| agaaatcctg ggaatgctga gattgaagat ctcatatttc tggcacggtc tgcactcatc | 840 | |
| ctgagaggat cagtggccca caagtcctgc ttgcctgctt gtgtgtacgg gcttgccgtg | 900 | |
| gccagtggat atgactttga gagagaaggg tactctctgg tcgggattga tccttttcgt | 960 | |
| ctgctgcaaa acagccaggt ctttagtcta attagaccaa atgagaatcc agcacataaa | 1020 | |
| agtcaattgg tgtggatggc atgccattct gcagcatttg aagatctgag agtctcaagc | 1080 | |
| ttcatcagag ggacaagagt ggccccaagg ggacaactat ctactagagg agttcaaatt | 1140 | |
| gcttcaaatg agaacatgga aacaatggac tccagcactc ttgaactgag aagcagatat | 1200 | |
| tgggctataa ggaccaggag tggaggaaac accaaccagc agagagcatc tgcaggacaa | 1260 | |
| atcagtgtgc agcctacttt ctcggtacag agaaatcttc ccttcgaaag agcgaccatt | 1320 | |
| atggcggcat tcacagggaa tacagagggc agaacatctg acatgaggac tgaaatcata | 1380 | |
| aggatgatgg aaagctccag accagaagat gtgtctttcc aggggcgggg agtcttcgag | 1440 | |
| ctctcggacg aaaaggcaac gaacccgatc gtgccttcct ttgacatgag taatgaagga | 1500 | |
| tcttatttct tcggagacaa tgcagaggaa tatgacaatt gaagaaaaat accccttgttt | 1560 | |
| ctact | 1565 | |

<210> SEQ ID NO 29
<211> LENGTH: 1027
<212> TYPE: DNA
<213> ORGANISM: Influenza A virus

<400> SEQUENCE: 29

| | | |
|---|---|---|
| agcaaaagca ggtagatatt gaaaaatgag tcttctaacc gaggtcgaaa cgtacgttct | 60 | |
| ctctatcgtc ccgtcaggcc ccctcaaagc cgagatcgcg cagagacttg aggatgtctt | 120 | |
| tgcaggaaag aacaccgatc tcgaggctct catggaatgg ctaaagacaa gaccaatcct | 180 | |
| gtcacctctg actaaaggga ttttaggatt tgtgttcacg ctcaccgtgc ccagtgagcg | 240 | |
| aggactgcag cgtagacgct ttgtccagaa tgccttaaat ggaaatggag atccaaacaa | 300 | |
| tatggatagg gcagttaagc tatacaagaa gctgaaaaga gaaataacat tccatggggc | 360 | |
| taaggaggtc gcactcagct actcaaccgg tgcacttgcc agttgtatgg gtctcatata | 420 | |
| caacaggatg ggaacggtga ccacagaagt ggcttttggc ctagtgtgtg ccacttgtga | 480 | |
| gcagattgca gattcacagc atcggtctca cagacagatg gcaactacca ccaacccact | 540 | |
| aatcaggcat gagaacagaa tggtgctggc cagcactaca gctaaggcta tggagcagat | 600 | |
| ggctggatcg agtgagcagg cagcggaagc catggaggtt gctagtcagg ctaggcagat | 660 | |
| ggtgcaggca atgaggacaa ttgggactca tcctagctcc agtgccggtc tgaaagataa | 720 | |
| tcttcttgaa aatttgcagg cctaccaaaa acgaatggga gtgcaaatgc agcgattcaa | 780 | |
| gtgatcctct tgttgttgcc gcaagtatca ttgggatact gcacttgata ttgtggattc | 840 | |
| ttgatcgtct tttcttcaaa tgcatttatc gtcgccttaa atacggtttg aaaagagggc | 900 | |
| cttctacgga aggggtacct gagtctatga gggaagagta tcggcaggaa cagcagagtg | 960 | |
| ctgtggatgt tgacgatggt cattttgtca acatagagct ggagtaaaaa actaccttgt | 1020 | |
| ttctact | 1027 | |

<210> SEQ ID NO 30
<211> LENGTH: 865
<212> TYPE: DNA
<213> ORGANISM: Influenza A virus

<400> SEQUENCE: 30

```
gtgacaaaga cataatggat tccaacacga taacctcgtt tcaggtagat tgttatctat 60
ggcacataag aaagctactc agtatgagag acatgtgtga tgccccccttt gatgacaggc 120
tccgaagaga ccaaaaggca ttaaagggaa gaggcagcac acttggactc gatttaagag 180
tggctacaat ggaggggaaa aagatcgttg aggacatcct gaagagtgag acaaatgaaa 240
acctcaaaat agccattgct tccagtcctg ctcctcggta tatcaccgat atgagcatag 300
aggagatgag ccgagaatgg tacatgctga tgcctaggca gaaaataact ggaggcctta 360
tggtgaaaat ggaccaagcc ataatggata aaagaattat ccttaaagca aatttctcag 420
ttctatttga tcaactagag acattagtct ctctgagggc attcacagaa agtggtgcta 480
ttgtggctga aatatttccc attccctccg taccaggaca ttttacagag gatgtcaaaa 540
atgcaattgg aatcctcatc ggtggacttg aatggaatga taactcaatt cgagcgtctg 600
aaaatataca gagattcgct tggggaatcc atgatgagaa tgggggacct tcactccctc 660
caaaacagaa acgctacatg gcgaaacgag ttgagtcaga agtttgaaga gatcagatgg 720
ctcattgctg aatgtagaaa tatactgaca aagactgaaa atagctttga acagataaca 780
tttttgcaag cattgcaact cttacttgaa gttgagagtg agataaggac cttctctttt 840
cagcttattt aatactaaaa aacac 865
```

<210> SEQ ID NO 31
<211> LENGTH: 2368
<212> TYPE: DNA
<213> ORGANISM: Influenza B virus

<400> SEQUENCE: 31

```
agcagaagcg gagctttaag atgaatataa atccatattt tcttttcata gatgtaccta 60
tacaggcagc aatttcaaca acattcccat acaccggtgt tccccccttat tctcatggaa 120
cgggaacagg ctacacaata gacaccgtga ttagaacaca cgagtactca aacaagggaa 180
aacaatacat ttctgatgtt acaggatgtg taatggtaga tccaacaaat gggccattac 240
ccgaagacaa tgaaccgagt gcctatgcac aattggattg tgttctggag gctttggata 300
gaatggatga agaacatcca ggtctgtttc aagcagggtc acagaatgcc atggaggcac 360
taatggtcac aacagtggac aaattgactc aggggagaca gacctttgat tggacggtgt 420
gtagaaacca acctgctgca acggcactga acacaacaat aacctctttt aggttgaatg 480
atttaaatgg agccgacaag ggtggattag tgcccttttg ccaagatatc attgattcat 540
tagacaaacc tgaaatgatt ttcttcacag taaagaatat aaagaaaaaa ttgcctgcta 600
aaaacagaaa gggtttcctt ataaaaagaa tacctatgaa ggtaaaagac agaataacaa 660
gagtggaata catcaaaaga gcattatcat taaacacaat gactaaagat gctgaaagag 720
gcaaactaaa aagaagagca attgccaccg ctgggataca aatcagagga tttgtattag 780
tagttgaaaa cttggctaaa aatatctgtg aaaatctaga gcaaagtggt ttacccgtag 840
gtggaaacga aaagaaggcc aaactatcaa atgcagtggc taaaatgctc agtaattgtc 900
caccaggagg gatcagtatg actgtgacag gagacaatac taaatggaat gaatgcttaa 960
atccaagaat ctttttggct atgactgaaa gaataaccag agacagccca atttggttcc 1020
gggatttttg tagtatagca ccggtcttgt tctccaataa aatagctaga ttgggaaaag 1080
ggttcatgat aacaagtaaa acaaaaaagac taaaagctca aataccttgt cccgatctgt 1140
```

```
ttaatatacc attagaaaga tataatgaag aaacaagggc aaaactgaaa aagctaaaac    1200
ctttcttcaa tgaagaagga acggcatctc tttcgccagg aatgatgatg ggaatgttta    1260
atatgctatc tacagtatta ggagtagccg cactagggat aaaaaacatt ggaaacaaag    1320
aatacttatg ggatggactg cagtcttcgg atgattttgc tctgtttgtt aatgcaaaag    1380
atgaagagac atgtatggaa ggaataaacg attttttaccg aacatgtaag ctattgggaa    1440
taaacatgag caaaagaaa agttactgta atgaaactgg gatgtttgaa tttaccagca    1500
tgttttacag agatggattt gtatctaatt ttgcaatgga actcccttca tttggagtcg    1560
ctggagtgaa tgaatcagca gacatggcaa taggaatgac aataataaag aacaatatga    1620
tcaacaatgg gatgggccca gcaacggcac aaacagccat acaattattc atagctgact    1680
atagatacac ctacaaatgc acaggggag attccaaagt ggaagggaag agaatgaaaa    1740
ttataaagga gctatgggaa acactaaag gaagagatgg tctattagta gcagatggtg    1800
ggcctaatct ttacaatttg agaaacctgc atattccaga ataatatta aaatacaaca    1860 taatggaccc tgagtacaaa ggacggttac tgcatcctca aaatcccttt gtaggacatt    1920
tgtctattga gggtatcaaa gaagcagata taacacctgc acatggccca ataagaaaa    1980 tggactacga tgcggtatct ggaactcata gttggagaac caaaggaac agatctatac    2040 taaacactga tcagaggaac atgattcttg aggaacaatg ctacgctaag tgttgcaacc    2100
tttttgaggc ttgctttaac agtgcgtcat acaggaaaacc agtaggccag cacagcatgc    2160
ttgaagctat ggcccacaga ttaagaatgg atgcacgact ggactatgag tcaggaagga    2220
tgtcaaaaga ggatttcgaa aaagcaatgg ctcaccttgg tgagattggg tacatgtaag    2280
ctccggaaat gtctatgggg ttattggtca tcgttgaata catgcggtgc acaaatgatt    2340
aaaatgaaaa aaggctcgtg tttctact                                      2368

<210> SEQ ID NO 32
<211> LENGTH: 2313
<212> TYPE: DNA
<213> ORGANISM: Influenza B virus

<400> SEQUENCE: 32
atgacgttgg ctaaaattga actactaaag cagctgttaa gggacaatga agccaaaacg      60
gtgttgagac agacaacggt agaccaatac aacataataa gaaaattcaa tacatcaaga     120
attgaaaaga acccttcatt aagaatgaag tgggccatgt gttccaattt tccccttagct    180 ctgaccaagg gtgatatggc aaatcgaatc cccttggaat acaagggaat acaacttaaa     240
acaaatgctg aagacatagg aactaaagga caaatgtgtt caatagcagc agttacctgg     300
tggaatacat gggcccat agggggatact gaagggtttg aaaaggtcta cgaaagcttt     360
tttctcagaa agatgagact tgacaatgcc acttggggcc gaataacctt ggcccctgtt     420
gagagagtaa gaaaaagagt actactaaac ccgctcacca ggaaatgcc cccagatgaa      480 gcgagcaatg taataatgga atatattattc cctaagaag caggaatacc aagagaatct     540
acttggatac atagagaact gataaaagaa aaaagagaaa aattgaaggg aacgatgata     600
actcccattg tactggcata catgcttgag agagaactag ttgcccgaag aaggttcctg     660
ccagtagcag gagcaacatc agcagagttc ataagaaatgc tacattgctt acaaggtgaa    720
aattggagac aaatatatca tccaggaggg aataaaactaa ctgaatctag atctcaatca    780
atgattgtag cttgcaggaa gataatcaga agatcaatag ttgcatcaaa cccactagag    840
ctagctgtag agattgcaaa taagactgtg atagacactg aacctttaaa atcatgtctg    900
```

| | | | | | |
|---|---|---|---|---|---|
| gcagccctgg | atggaggtga | tgtagcctgt | gacataataa | gagctgcatt | aggattaaaa | 960
| attagacaaa | gacaaagatt | tgggagactt | gaactaaaga | gaatatcagg | aagaggattc | 1020
| aaaaatgatg | aagagatatt | aatcggaaac | ggaacaatac | aaaagattgg | aatatgggac | 1080
| ggagaagagg | aattccatgt | aagatgtggc | gaatgcaggg | ggatattgaa | aaaaagccaa | 1140
| atgagaatgg | aaaaactact | gataaattca | gccaaaaagg | aggacatgaa | agatttaata | 1200
| atcttatgca | tggtattttc | tcaagacact | aggatgttcc | aaggagtgag | aggagagata | 1260
| aattttctta | atcgagcagg | ccaactttta | tcccccatgt | accaactcca | acgatacttt | 1320
| ctgaatagga | gcaatgacct | ttttgatcaa | tggggatatg | aggaatcacc | taaagcaagt | 1380
| gagctacatg | gataaaatga | attaatgaat | gcatctgact | atacattgaa | aggggttgta | 1440
| gtaacaaaaa | atgtgattga | tgattttagt | tctactgaaa | cagaaaaagt | atctataaca | 1500
| aaaaatctta | gtttaataaa | aaggactggg | gaagttataa | tgggagccaa | tgacgtaagt | 1560
| gaattagaat | cacaagcaca | gctaatgata | acgtatgata | cacccaagat | gtgggaaatg | 1620
| ggaacaacca | agaactggt | acaaaacact | taccaatggg | tgcttaaaaa | tttagtaaca | 1680
| ttgaaggctc | agtttctttt | gggaaaagaa | gacatgttcc | aatgggatgc | atttgaagca | 1740
| tttgaaagca | taatccctca | gaagatggct | ggtcagtaca | gtggatttgc | aagagcagtg | 1800
| ctcaaacaaa | tgagagacca | agaggttatg | aaaactgacc | aattcataaa | attgttgcct | 1860
| ttctgttttt | cgccaccaaa | attaaggagc | aatggagagc | cttatcaatt | tttgaggctt | 1920
| atgctgaaag | gaggagggga | aaatttcatc | gaagtaagga | aagggtcccc | cttgttctcc | 1980
| tacaatccac | aaacggaaat | cctaactata | tgcggcagaa | tgatgtcatt | aaaaggaaaa | 2040
| attgaggatg | aagaaagaaa | tagatcaatg | gggaatgcag | tactggcagg | ctttcttgtt | 2100
| agtggcaaat | atgaccctga | tcttggagat | ttcaaaacca | ttgaggaact | tgaaagacta | 2160
| aaaccgggag | aaaagccaa | catcttactt | taccaaggaa | agcccgttaa | agtagttaaa | 2220
| aggaaaagat | atagtgcttt | atccaatgat | atttcacaag | ggattaagag | acaaagaatg | 2280
| acagttgagt | ccatggggtg | ggccttgagc | taa | | | 2313

<210> SEQ ID NO 33
<211> LENGTH: 2204
<212> TYPE: DNA
<213> ORGANISM: Influenza B virus

<400> SEQUENCE: 33

| | | | | | |
|---|---|---|---|---|---|
| atggatactt | ttattacaaa | gaatttccag | actacaataa | tacaaaaggc | caaaaacaca | 60
| atggcagaat | ttagtgaaga | tcctgaatta | cagccagcag | tactattcaa | catctgcgtc | 120
| catctggagg | tctgctatgt | aataagtgat | atgaactttc | ttgatgagga | aggaaagaca | 180
| tatacagcat | tagaaggaca | aggaaaagag | caaaatttga | gaccacagta | tgaagtgatt | 240
| gagggaatgc | caagaaacat | agcatggatg | gttcaaagat | ccttagccca | agagcatgga | 300
| atagagactc | caaggtatct | ggctgattta | tttgattata | aaaccaagag | gtttatcgaa | 360
| gtcggaataa | caaagggatt | ggctgatgat | tacttttgga | aaagaaaga | aaagttgggg | 420
| aatagcatgg | aactgatgat | attcagctac | aatcaagact | actcgttaag | tgatgaatct | 480
| tcattggatg | aggaaggaaa | agggagagtg | ctaagcagac | tcacagaact | tcaggctgag | 540
| ttaagtttga | aaaccctatg | gcaagttcta | ataggggaag | aagaaattga | aaaggaatt | 600
| gacttcaaac | ttggacaaac | aatatctaaa | ctgaggaata | tatctgttcc | agctggtttc | 660

-continued

```
tccaattttg aagggatgag aagttacata gacaacatag accctaaagg agcaatagag    720
agaaatctag caaggatgtc tcccttagta tcagttacac ccaaaaagtt gaaatgggag    780
gacctgagac ccatagggcc tcacatttac aaccatgagc taccagaagt tccatataat    840
gcctttctcc tcatgtctga tgagttgggg ctggccaata tgactgaagg aaagtccaag    900
aaaccgaaga ccttagctaa ggaatgtcta gaaaggtatt caacactacg tgatcaaact    960
gacccaatat tgataatgaa aagcgaaaaa gctaacgaaa acttcttatg gaggttatgg   1020
agggactgtg taaatacaat aagcaatgag gaaacaggca acgaattaca gaaaaccaat   1080
tatgccaagt gggccacagg agatggacta acataccaaa aaataatgaa agaagtagca   1140
atagatgacg aaacgatgta ccaagaagaa cccaaaatac ccaataaatg tagagtggct   1200
gcttgggttc aggcagagat gaatctactg agtactctga caagtaaaag ggccctggat   1260
ctgccagaaa tagggccaga tgtagcaccc gtggagcatg tagggagtga aagaaggaaa   1320
tactttgtta atgaaatcaa ctactgtaaa gcctctacag ttatgatgaa gtatgtactt   1380
tttcacactt cattattaaa tgaaagcaat gctagtatgg gaaaatataa agtaatacca   1440
atcaccaaca gagtggtaaa tgaaaaaggg gaaagctttg acatgcttta tggtctggcg   1500
gttaaggggc aatctcattt gcggggggac acggatgttg taacagttgt gactttcgag   1560
tttagtagta cagatcctag agtggactca ggaaagtggc caaaatatac tgtctttaaa   1620
attggctccc tatttgtgag tggaagagaa aaacctgtgt acctatattg ccgagtgaat   1680
ggtacaaaca aaatccaaat gaaatgggga atggaagcta gaagatgtct gcttcaatca   1740
atgcaacaaa tggaggcaat tgttgatcaa gaatcatcga tacaagggta tgatatgacc   1800
aaagcttgtt tcaagggaga cagagtgaat aatcccaaaa ctttcagtat tgggactcag   1860
gaaggcaaac tagtaaaagg gtcctttggg aaagcactaa gagtaatatt caccaaatgt   1920
ttgatgcatt atgtatttgg aaatgctcaa ttggaggggt ttagtgccga atctaggaga   1980
cttctactgt taattcaggc attaaaagac aggaagggcc cttgggtatt tgacttggag   2040
ggaatgtact ttggagtaga ggaatgtatt agtaacaatc cttgggtaat acagagtgca   2100
tactggttta atgaatggtt gggcattgaa aaagaaggaa gtaaagtgtt agaatcaata   2160
gatgaaataa tggatgaatg aacgaagggc atagcgctca attt                    2204
```

<210> SEQ ID NO 34
<211> LENGTH: 1841
<212> TYPE: DNA
<213> ORGANISM: Influenza B virus

<400> SEQUENCE: 34

```
ggcagaagca cagcattttc ttgtgagctt cgagcactaa taaaactgaa aatcaaaatg     60
tccaacatgg atattgacag tataaatacc ggaacaatcg ataaaacacc agaagaactg    120
actcccggaa ccagtggggc aaccagacca atcatcaagc cagcaaccct tgctccgcca    180
agcaacaaac gaacccgaaa tccatctcca gaaaggacaa ccacaagcag tgaaaccgat    240
atcggaagga aaatccaaaa gaaacaaacc ccaacagaga taaagaagag cgtctacaaa    300
atggtggtaa aactgggtga attctacaac cagatgatgg tcaaagctgg acttaatgat    360
gacatggaaa ggaatctaat tcaaaatgca caagctgtgg agagaatcct attggctgca    420
actgatgaca agaaaactga ataccaaaag aaaaggaatg ccagagatgt caaagaaggg    480
aaggaagaaa tagaccacaa caagacagga ggcacctttt ataagatggt aagagatgat    540
aaaaccatct acttcagccc tataaaaatt accttttttaa aagaagaggt gaaaacaatg    600
```

-continued

```
tacaagacca ccatggggag tgatggtttc agtggactaa atcacattat gattggacat    660
tcacagatga acgatgtctg tttccaaaga tcaaagggac tgaaaagggt tggacttgac    720
ccttcattaa tcagtacttt tgccggaagc acactaccca gaagatcagg tacaactggt    780
gttgcaatca aggaggtgg aactttagtg atgaagcca tccgatttat aggaagagca    840
atggcagaca gagggctact gagagacatc aaggccaaga cggcctatga aaagattctt    900
ctgaatctga aaacaagtg ctctgcgccg caacaaaagg ctctagttga tcaagtgatc    960
ggaagtagga acccagggat tgcagacata aagacctaa ctctgcttgc cagaagcatg   1020
gtagttgtca gaccctctgt agcgagcaaa gtggtgcttc cataagcat ttatgctaaa   1080 atacctcaac taggattcaa taccgaagaa tactctatgg ttgggtatga agccatggct   1140
ctttataata tggcaacacc tgtttccata ttaagaatgg gagatgacgc aaaagataaa   1200
tctcaactat tcttcatgtc gtgcttcgga gctgcctatg aagatctaag agtgttatct   1260
gcactaacgg gcaccgaatt taagcctaga tcagcactaa aatgcaaggg tttccatgtc   1320
ccggctaagg agcaagtaga aggaatgggg gcagctctga tgtccatcaa gcttcagttc   1380
tgggccccaa tgaccagatc tggagggaat gaagtaagtg gagaaggagg gtctggtcaa   1440
ataagttgca gccctgtgtt tgcagtagaa agacctattg ctctaagcaa gcaagctgta   1500
agaagaatgc tgtcaatgaa cgttgaagga cgtgatgcag atgtcaaagg aaatctactc   1560
aaaatgatga atgattcaat ggcaaagaaa accagtggaa atgctttcat tgggaagaaa   1620
atgtttcaaa tatcagacaa aaacaaagtc aatcccattg agattccaat taagcagacc   1680
atccccaatt tcttctttgg gagggacaca gcagaggatt atgatgacct cgattattaa   1740
agcaataaaa tagacactat ggctgtgact gtttcagtac gtttgggatg tgggtgttta   1800
ctcttattga aataaatgta aaaaatgctg ttgtttctac t                       1841
```

<210> SEQ ID NO 35
<211> LENGTH: 1191
<212> TYPE: DNA
<213> ORGANISM: Influenza B virus

<400> SEQUENCE: 35

```
agcagaagca cgcactttct taaaatgtcg ctgtttggag acacaattgc ctacctgctt     60
tcactaatag aagatggaga aggcaaagca gaactagctg aaaaattaca ctgttggttc    120
ggtgggaaag aatttgacct agattctgct ttggaatgga taaaaacaa aaggtgccta    180 actgatatac aaaaagcact aattggtgcc tctatatgct ttttaaaacc caagaccaa    240 gaaagaaaaa ggagattcat cacagagccc ctgtcaggaa tgggaacaac agcaacaaag    300
aagaaaggcc taattctagc tgagagaaaa atgagaagat gtgtaagctt tcatgaagca    360
tttgaaatag cagaaggcca cgaaagctca gcattactat attgtcttat ggtcatgtac    420
ctaaaccctg aaaactattc aatgcaagta aaactaggaa cgctctgtgc tttatgcgag    480
aaacaagcat cgcactcgca tagagcccat agcagagcag caaggtcttc ggtacctgga    540
gtaagacgag aaatgcagat ggtttcagct atgaacacag caaagacaat gaatggaatg    600
ggaaagggag aagacgtcca aaaactagca gaagagctgc aaaacaacat ggagtgttg    660 agatctctag gagcaagtca aaagaatgga gaggaattg ccaaagatgt aatggaagtg    720
ctaaaacaga gctctatggg aaattcagct cttgtgagga atacttata atgctcgaac    780 cacttcagat tctttcaatt tgttctttca ttttatcagc tctccatttc atggcttgga    840
```

| caatagggca tttgaatcaa ataaaaagag gggtaaactt gaaatacaa ataaggaatc | 900 |
| caaataagga ggcaataaac agagaggtgt caattctgag acacaattac caaaaggaaa | 960 |
| tccaagccaa agaaacaatg aagaaaatac tctctgacaa catggaagta ttgggtgacc | 1020 |
| acatagtagt tgaagggctt tcaactgatg agataataaa aatgggtgaa acagttttgg | 1080 |
| aggtggaaga attgcaatga gcccaatttt cactgtattt cttactatgc atttaagcaa | 1140 |
| attgtaatca atgtcagtga ataaaactgg aaaaagtgcg ttgtttctac t | 1191 |

<210> SEQ ID NO 36
<211> LENGTH: 1096
<212> TYPE: DNA
<213> ORGANISM: Influenza B virus

<400> SEQUENCE: 36

| cgcagaagca gaggatttat ttagtcactg gcaaacggaa agatggcgga caacatgacc | 60 |
| acaacacaaa ttgaggtggg tccgggagca accaatgcca ctataaactt gaagcagga | 120 |
| attctggagt gctatgaaag gttttcatgg caaagagccc ttgactatcc tggtcaagac | 180 |
| cgcctacaca gactaaaacg aaaattagaa tcaagaataa agactcacaa caagagtgag | 240 |
| cctgagaata aaaggatgtc tcttgaagag agaaagcaa ttggggtaaa atgatgaaa | 300 |
| gtgcttctgt ttatggatcc ctctgctgga attgaagggt ttgagccata ctgtgtgaaa | 360 |
| aatccctcaa ctagcaaatg tccaaattac gattggaccg attaccctcc aacccccagga | 420 |
| aagtaccttg atgacataga agaagagccg gaaaatgtcg atcacccaat tgaggtagta | 480 |
| ttaagggaca tgaacaataa agatgcacga caaaagataa aggatgaagt aaacactcag | 540 |
| aaagagggga aattccgttt gacaataaaa agggatatac gtaatgtgtt gtccttgaga | 600 |
| gtgttggtga acggaaccctt cctcaagcac cctaatggag acaagtcctt atcaactctt | 660 |
| catagattga atgcatatga ccagaatgga gggcttgttg ctaaacttgt tgctactgat | 720 |
| gatcggacag tggaggatga aaaagatggc catcggatcc tcaactcact cttcgagcgt | 780 |
| tttgatgaag acattcaaa gccaattcga gcagctgaaa ctgcggtggg agtcttatcc | 840 |
| caatttggtc aagagcaccg attatcacca gaagagggag acaattagac tggccacgga | 900 |
| agaactttat ctcttgagta aaagaattga tgatagtata ttgttccaca aaacagtaat | 960 |
| agctaacagc tccataatag ctgacatgat tgtatcatta tcattactgg aaacattgta | 1020 |
| tgaaatgaag gatgtggttg aagtgtacag caggcagtgc ttatgaatgt aaaataaaaa | 1080 |
| tcctcttgtt actact | 1096 |

<210> SEQ ID NO 37

<400> SEQUENCE: 37

000

<210> SEQ ID NO 38

<400> SEQUENCE: 38

000

<210> SEQ ID NO 39
<211> LENGTH: 46
<212> TYPE: DNA
<213> ORGANISM: Artificial Sequence
<220> FEATURE:
<223> OTHER INFORMATION: primer

```
<400> SEQUENCE: 39
catgatcgtc tcagggagca aaagcagggt agataatcac tcacag            46

<210> SEQ ID NO 40
<211> LENGTH: 43
<212> TYPE: DNA
<213> ORGANISM: Artificial Sequence
<220> FEATURE:
<223> OTHER INFORMATION: primer

<400> SEQUENCE: 40
catgatcgtc tcgtattagt agaaacaagg gtatttttct tta               43
```

BARCODED INFLUENZA VIRUSES AND DEEP MUTATIONAL SCANNING LIBRARIES INCLUDING THE SAME

CROSS REFERENCE TO RELATED APPLICATION

This application claims the benefit of U.S. Provisional Patent Application No. 62/935,954, filed on Nov. 15, 2019, which is incorporated herein by reference in its entirety as if fully set forth herein.

STATEMENT REGARDING FEDERALLY SPONSORED RESEARCH OR DEVELOPMENT

This invention was made with government support under grant number AI127893 awarded by the National Institutes of Health. The government has certain rights in the invention.

STATEMENT REGARDING SEQUENCE LISTING

The Sequence Listing associated with this application is provided in text format in lieu of a paper copy and is hereby incorporated by reference into the specification. The name of the text file containing the Sequence Listing is 2E49832_ST25.txt. The text file is 76 KB, was created on Nov. 13, 2020, and is being submitted electronically via EFS-Web.

FIELD OF THE DISCLOSURE

Methods to create barcoded influenza viruses without disrupting the function of the viral proteins and the proper packaging of the viral genome segments are described. The barcoded influenza viruses can be used within deep mutational scanning libraries to map influenza resistance mutations to therapeutic treatments including antibodies and drugs, as well as mutations that escape polyclonal immunity elicited by vaccination or prior infection. The libraries can also be used to predict influenza strains that may become resistant to therapeutic treatments, escape pre-existing immunity, and/or more easily evolve to infect new species. The libraries include features that allow efficient collection and assessment of informative data, obviating bottlenecks of previous approaches. They also make it possible to study combinations of mutations within viral genes.

BACKGROUND OF THE DISCLOSURE

Proteins are made of strings of amino acids with different proteins having different numbers and orders of amino acids. Proteins are essential to the functioning of cells and organisms. A powerful way to study proteins is through mutagenesis. Mutagenesis refers to altering the amino acid that naturally occurs at a position along the string of amino acids that creates a given protein. Systematically altering amino acids at different positions through mutagenesis can identify those amino acids that are essential to the function of the protein. Deep mutational scanning refers to methods of generating and characterizing hundreds of thousands of mutants or more of a given protein. More particularly, deep mutational scanning can refer to altering each amino acid position with all possible alternative amino acids.

One scenario where the study of proteins is extremely beneficial is in relation to viruses. Many viruses can be effectively managed or treated. For example, vaccination has all but ameliorated smallpox and measles, once among mankind's greatest scourges. Unfortunately, however, numerous viruses continue to pose significant health threats. Examples include influenza virus, human immunodeficiency virus (HIV), Ebola virus, and Middle Eastern respiratory syndrome coronavirus (MERS-CoV).

To combat the spread of viruses, scientists and doctors need tools to know when drugs, vaccines, or antibodies are effectively working against viral proteins, or conversely, when these viral proteins have developed resistance to these countermeasures and pose a greater risk.

The influenza virus belongs to the Orthomyxoviridae family and is an enveloped viruses with an eight-segmented single-stranded, negative-sense viral RNA (vRNA) genome. The life cycle of influenza virus can be briefly described as follows. Influenza virions (the complete, infective form of a virus outside a host cell, with a core of RNA and a capsid) enter the host cell, where their negative sense RNA is released into the cytoplasm. The virus' own RNA replicase, known as RNA-dependent RNA polymerase (RdRp), is used to form positive sense RNA template strands through complementary base pairing. There are two distinct forms of this positive sense RNA: one that serves as messenger RNA (mRNA), which is translated into viral proteins by ribosomes of the host cell; and another that serves as template to make more negative sense RNA strands.

In viruses with segmented genomes like the influenza virus, replication occurs in the nucleus and the RdRp produces one monocistronic mRNA strand (encoding one polypeptide per RNA molecule) from each genome segment. Each genome segment includes a promoter sequence, segment-specific non-coding regions adjacent to the promoter region, and open reading frame coding sequences that encode particular viral proteins. Each segment also includes a packaging signal on each end of the vRNA (referred to as the 5' end and the 3' end). Each packaging signal is unique to each vRNA.

New viral capsids are assembled with the capsomere proteins. The negative sense RNA strands combine with capsids and viral RdRp to form new negative sense RNA virions. After assembly and maturation of nucleocapsid, the new virions exit the cell through the cell membrane by budding or lysis to further infect other cells.

In the context of viral infection, years of research has led to an understanding of many of the proteins important in the viral life cycle. The first step in viral infection is binding of a virion's viral entry protein to a host cell. This binding is followed by fusion of the virion with the host cell. For many human pathogenic viruses, the binding and fusion steps are performed by a single viral entry protein. For example, influenza virus uses a single-entry protein for binding and fusion with a host cell.

Viral entry proteins are a primary target of immune system responses against viral infections. Most vaccines elicit neutralizing antibodies to the viral entry protein. Therapeutic antibodies can also be used to impair the activity of viral entry proteins, with the potential to both protect against infection as well as to therapeutically treat active infection. However, viral entry proteins are able to mutate and evolve over time, and mutations can allow these proteins to escape recognition by immune system responses and therapeutic antibodies. Evasion or susceptibility to neutralization by antibodies can be examined using mutant viral entry proteins in antibody neutralization assays.

A virus' viral entry protein is also a key determinant of the species that the particular virus can infect, and adaptive evolution of these entry proteins has been retrospectively characterized in most molecularly documented examples of non-human viruses jumping into humans. For example, the influenza pandemics of 1918, 1957, and 1968 all involved mutations that turned viral entry proteins from avian viral strains to strains that could better infect humans.

Deep mutational scanning has been used to completely map functional and antigenic effects of all mutations to the entry proteins of influenza virus and HIV. For example, FIG. 1 outlines an approach that was used to characterize mutations to the influenza entry protein, hemagglutinin (HA). Briefly, all codon mutants of the genes encoding HA were created and all associated replication-competent viruses were generated. These viruses were passaged in cell culture (e.g., transferred from a previous culture to fresh growth medium) and deep sequencing was used to quantify the frequency of every mutation in the passaged viruses versus the original pool to estimate the preference of each site for each amino acid (FIG. 1). The results of these experiments were informative for understanding the evolution of influenza in nature. The approach was also used to completely map how single amino acid mutations affect antibody neutralization. As shown in FIG. 1, the virus libraries were subjected to antibody or mock neutralization before infection into cells, and deep sequencing was used to identify mutations enriched by antibody selection. The results precisely pinpointed antibody epitopes and which specific mutations allow escape from antibody neutralization (FIG. 1). Further, the approach depicted in FIG. 1 was advantageous because it directly measured viral infection or antibody neutralization. This contrasts with many high-throughput approaches that are currently available that measure surrogate viral activities like protein abundance or binding. Directly measuring infection or antibody neutralization is important because the functions of entry proteins are far more complex than can be inferred based on surrogate activities.

The work described in relation to FIG. 1 garnered substantial notice; for instance, Moncla, et al. (2017) Trends in Microbiology 25: 432-434. For instance, Moncla et al stated that "the method could comprehensively catalogue influenza escape mutations" and "provide critical new information for antigenic models." Unfortunately, however, the applicability and utility of this described approach remained severely limited. While informative, these mutagenesis experiments were too low-throughput to keep up with the many relevant questions when studying rapidly evolving viruses that sample all possible mutations within a single human infection.

One challenge is the deep sequencing required for this type of work. There is now substantial literature on sequencing methods for deep mutational scanning. The key point is that sequencing methods that are currently used (e.g., Illumina sequencing) can have an error rate that is too high to produce informative and reliable results without complex and expensive error-correction strategies. Alternative methods (such as PacBio) lack the throughput and/or accuracy to efficiently (and affordably) characterize diverse libraries at multiple conditions. One solution is to associate each variant in a library with a unique nucleotide barcode (Hiatt, et al. Nat Methods 7: 119-122 (2010)). The barcodes can then be sequenced using standard sequencing (e.g., Illumina) to read out the library composition. This approach is efficient and cheap and provides a linkage between barcode and variant. Unfortunately, however, standard barcoding has not been successful with many viruses, including influenza virus. Varble et al., *Cell Host and Microbe,* 16(5), 691-700 (2014); Heaton et al., *Proceedings of the National Academy of Sciences of the U.S.A.,* 110(50), 20248-20253 (2013). This is thought to be at least in part because, due to the compactness of the viral genome, it is difficult to insert a nucleotide barcode without disrupting the function of the viral proteins and the proper packaging of the viral genome segments.

SUMMARY OF THE DISCLOSURE

The current disclosure provides methods that allow insertion of a nucleotide barcode into the influenza virus genome without disrupting the function of the viral proteins and the proper packaging of the viral genome segments. These methods significantly improve the ability to perform deep mutational scanning analyses on the influenza virus. The methods include two key aspects: (i) duplicating and inserting a copy of the 5' vRNA packaging signal between the end of the corresponding viral genome segment's open reading frame (corresponding to the stop codon of the transcribed positive sense mRNA) and the naturally occurring non-coding portion of the 5' vRNA packaging signal; and (ii) inserting the nucleic acid barcode between the end of the viral genome segment's open reading frame (corresponding to the stop codon of the transcribed positive sense mRNA) and the inserted copy of the 5' vRNA packaging signal. This approach is depicted schematically in FIG. 2A and allows the creation of barcoded influenza virus that can be used to create deep mutational scanning libraries to assess influenza viral proteins. Among many potential uses, the libraries can be used to map quickly and with high resolution amino acid changes in a given influenza protein that are important to escape detection by the immune system, therapeutic antibodies, or the binding domains of other therapeutic molecules. As will be described in additional detail throughout this disclosure, there are also numerous other important and beneficial uses of the barcoded influenza viruses described herein.

In particular embodiments, libraries of barcoded influenza virus variants can also include absolute standards. These absolute standards can include viruses with glycoproteins from influenza strains that are not recognized by sera or antibodies of a species under consideration. For example, the absolute standards can include viruses with glycoproteins from influenza strains that do not infect humans and are not recognized by sera or antibodies of humans. Such standards can allow absolute quantification of selection on mutations and create absolute measurements of viral neutralization in high-throughput mode.

Taken together, the disclosed barcoded influenza viruses and resulting mutational scanning libraries provide an important advance in the ability to generate, store, and characterize a large number of variant influenza viral proteins.

BRIEF DESCRIPTION OF THE SEVERAL VIEWS OF THE DRAWINGS

Many of the drawings submitted herein are better understood in color. Applicant considers the color versions of the drawings as part of the original submission and reserves the right to present color images of the drawings in later proceedings.

FIGS. 2A, 2B. Barcoded influenza virus vRNA with packaging signals decoupled from the coding sequence. In FIG. 2A, a sufficient sequence of the 5' end of the viral RNA (which is the 3' end of the mRNA transcribed from the negative sense vRNA depicted in the FIG.) is duplicated (typically >90 nucleotides). This duplicated sequence is inserted before the non-coding portion of the 5' endogenous packaging signal with a barcode inserted between the terminus of the viral protein-coding region and the duplicated/ inserted packaging signal. The duplicated sequence typically includes noncoding and coding sequences to capture the packaging signal. FIG. 2B depicts the approach shown in FIG. 2A and additionally performing a similar duplication and insertion at the other end of the gene segment. This duplication and insertion at the 3' vRNA end is optional.

FIGS. 5A-5C. Depiction of measuring antibody neutralization curves using deep sequencing of viral libraries and visualizing the results. (FIG. 5A) Viral variants are either treated with an antibody or left untreated. At each antibody concentration, a specific fraction of each viral variant survives neutralization. Here all but the V1K variant are mostly neutralized. (FIG. 5B) By measuring the fraction surviving at several concentrations, a neutralization curve can be interpolated. The middle vertical dashed line is the concentration corresponding to the scenario in FIG. 5A. (FIG. 5C) When curves for many mutants have been measured, it is more informative to show the resulting measurements in logo plots [Adapted from Doud et al. (2018) bioRxiv DOI: 210468]. The height of each letter is the fraction of variants with that mutation that survive at the antibody concentrations indicated by vertical lines in FIG. 5B.

FIG. 6. Algorithms to extract functional information from deep mutational scanning counts adapted from Bloom (2015) BMC Bioinformatics 16: 168.

(FIG. 8A) Viruses are adapted to their long-standing animal reservoirs. When they jump to humans, they initially may be poorly adapted. (FIG. 8B) Host adaptation can be scored based on sequence, and adaptation after a jump can be charted.

FIG. 9. Exemplary sequences supporting the disclosure: Packaging Signal at 5' end for Influenza A virus Segment 4 (SEQ ID NO: 1); Packaging Signal at 3' end for Influenza A virus Segment 4 (SEQ ID NO: 2); Packaging Signal at 5' end for Influenza A virus Segment 6 (SEQ ID NO: 3); Packaging Signal at 3' end for Influenza A virus Segment 6 (SEQ ID NO: 4); Influenza A virus (A/Puerto Rico/8/1934(H1N1)) segment 4 (NCBI Ref Seq: NC_002017.1; (SEQ ID NO:5). The coding sequence for the gene HA is in bold. Influenza A virus (A/Puerto Rico/8/1934(H1N1)) segment 6 (NCBI Ref Seq: NC_002018.1; SEQ ID NO: 6). The coding sequence for the gene NA is in bold. Influenza A virus (A/New York/392/2004(H3N2)) segment (NCBI Ref Seq: NC_007366.1; SEQ ID NO: 7). The coding sequence for the gene HA is in bold. Influenza A virus (A/New York/392/ 2004(H3N2)) segment 6 (NCBI Ref Seq: NC_007368.1; SEQ ID NO: 8). The coding sequence for the gene NA is in bold. Influenza A virus (A/goose/Guangdong/1/1996 (H5N1)) hemagglutinin (HA) gene (NCBI Ref Seq: NC_007362.1; SEQ ID NO: 9). The coding sequence for the gene HA is in bold. Influenza A virus (A/Goose/Guangdong/ 1/96(H5N1)) neuraminidase (NA) gene (NCBI Ref Seq: NC_007361.1; SEQ ID NO: 10). The coding sequence for the gene NA is in bold. Influenza B virus (B/Lee/1940) segment 4 (NCBI Ref Seq: NC_002207.1; SEQ ID NO:11). The coding sequence for the gene HA is in bold. Influenza B virus (B/Lee/1940) segment 6 (NCBI Ref Seq: NC_002209.1; SEQ ID NO:12). The coding sequence for the gene NB is in bold; the coding sequence for the gene NA is underlined. Influenza A virus (A/Puerto Rico/8/1934 (H1N1)) segment 1 (NCBI Ref Seq: NC_002023.1; SEQ ID NO: 13). The coding sequence for the gene PB2 is in bold. Influenza A virus (A/Puerto Rico/8/1934(H1N1)) segment 2 (NCBI Ref Seq: NC_002021.1; SEQ ID NO: 14). The coding sequence for the gene PB1 is in bold; the coding sequence for the gene PB1-F2 is underlined. Influenza A virus (A/Puerto Rico/8/1934(H1N1)) segment 3 (NCBI Ref Seq: NC_002022.1; SEQ ID NO: 15). The coding sequence for the gene PA is in bold. Influenza A virus (A/Puerto Rico/8/1934(H1N1)) segment 5 (NCBI Ref Seq: NC_002019.1; SEQ ID NO: 16). The coding sequence for the gene NP is in bold. Influenza A virus (A/Puerto Rico/8/ 1934(H1N1)) segment 7 (NCBI Ref Seq: NC_002016.1; SEQ ID NO: 17). The coding sequence for the gene M2 is in bold; the coding sequence for the gene M1 is underlined. Influenza A virus (A/Puerto Rico/8/1934(H1N1)) segment 8 (NCBI Ref Seq: NC_002020.1; SEQ ID NO: 18). The coding sequence for the gene NS2 is in bold; the coding sequence for the gene NS1 is underlined. Influenza A virus (A/New York/392/2004(H3N2)) segment 1 (NCBI Ref Seq: NC_007373.1; SEQ ID NO: 19). The coding sequence for the gene PB2 is in bold. Influenza A virus (A/New York/ 392/2004(H3N2)) segment 2 (NCBI Ref Seq: NC_007372.1; SEQ ID NO: 20). The coding sequence for the gene PB1 is in bold; the coding sequence for the gene PB1-F2 is underlined. Influenza A virus (A/New York/392/ 2004(H3N2)) segment 3 (NCBI Ref Seq: NC_007371.1; SEQ ID NO: 21). The coding sequence for the gene PA is in bold; the coding sequence for the gene PA-X is underlined. Influenza A virus (A/New York/392/2004(H3N2)) segment 5 (NCBI Ref Seq: NC_007369.1; SEQ ID NO: 22). The coding sequence for the gene NP is in bold. Influenza A virus (A/New York/392/2004(H3N2)) segment 7 (NCBI Ref Seq: NC_007367.1; SEQ ID NO: 23). The coding sequence for the gene M2 is in bold; the coding sequence for the gene M1 is underlined. Influenza A virus (A/New York/392/2004 (H3N2)) segment 8 (NCBI Ref Seq: NC_007370.1; SEQ ID NO: 24). The coding sequence for the gene NS2 is in bold; the coding sequence for the gene NS1 is underlined. Influenza A virus (A/Goose/Guangdong/1/96(H5N1)) polymerase (PB2) gene (NCBI Ref Seq: NC_007357.1; SEQ ID NO: 25). The coding sequence for the gene PB2 is in bold. Influenza A virus (A/goose/Guangdong/1/1996(H5N1)) polymerase (PB1) and PB1-F2 protein (PB1-F2) genes (NCBI Ref Seq: NC_007358.1; SEQ ID NO: 26). The coding sequence for the gene PB1 is in bold; the coding sequence for the gene PB1-F2 is underlined. Influenza A virus (A/goose/Guangdong/1/1996(H5N1)) polymerase (PA) and PA-X protein (PA-X) genes (NCBI Ref Seq: NC_007359.1; SEQ ID NO: 27). The coding sequence for the gene PA is in bold; the coding sequence for the gene PA-X is underlined. Influenza A virus (A/Goose/Guangdong/1/96(H5N1)) nucleocapsid protein (NP) gene (NCBI Ref Seq: NC_007360.1; SEQ ID NO: 28). The coding sequence for the gene NP is in bold. Influenza A virus (A/goose/Guangdong/1/1996(H5N1)) segment 7 (NCBI Ref Seq: NC_007363.1; SEQ ID NO: 29). The coding sequence for the gene M2 is in bold; the coding sequence for the gene M1 is underlined. Influenza A virus (A/goose/Guangdong/1/1996(H5N1)) segment 8 (NCBI Ref Seq: NC_007364.1; SEQ ID NO: 30). The coding sequence for the gene NS2 is in bold; the coding sequence for the gene NS1 is underlined. Influenza B virus RNA 1 (NCBI Ref Seq: NC_002204.1; SEQ ID NO:31). The coding sequence for the gene PB1 is in bold. Influenza B virus (B/Lee/1940) segment 2 (NCBI Ref Seq: NC_002205.1; SEQ ID NO:32). The entire sequence encodes PB2. Influenza B virus (B/Lee/1940) segment 3 (NCBI Ref Seq: NC_002206.1; SEQ ID NO:33). The coding sequence for the gene PA is in bold. Influenza B virus (B/Lee/1940) segment 5 (NCBI Ref Seq: NC_002208.1; SEQ ID NO:34). The coding sequence for the gene NP is in bold. Influenza B virus (B/Lee/1940) segment 7 (NCBI Ref Seq: NC_002210.1; SEQ ID NO:35). The coding sequence for the gene M1 is in bold. Influenza B virus (B/Lee/1940) segment 8 (NCBI Ref Seq: NC_002211.1; SEQ ID NO:36). The coding sequence for the gene NS2 is in bold; the coding sequence for the gene NS1 is underlined.

DETAILED DESCRIPTION

Figure 1:
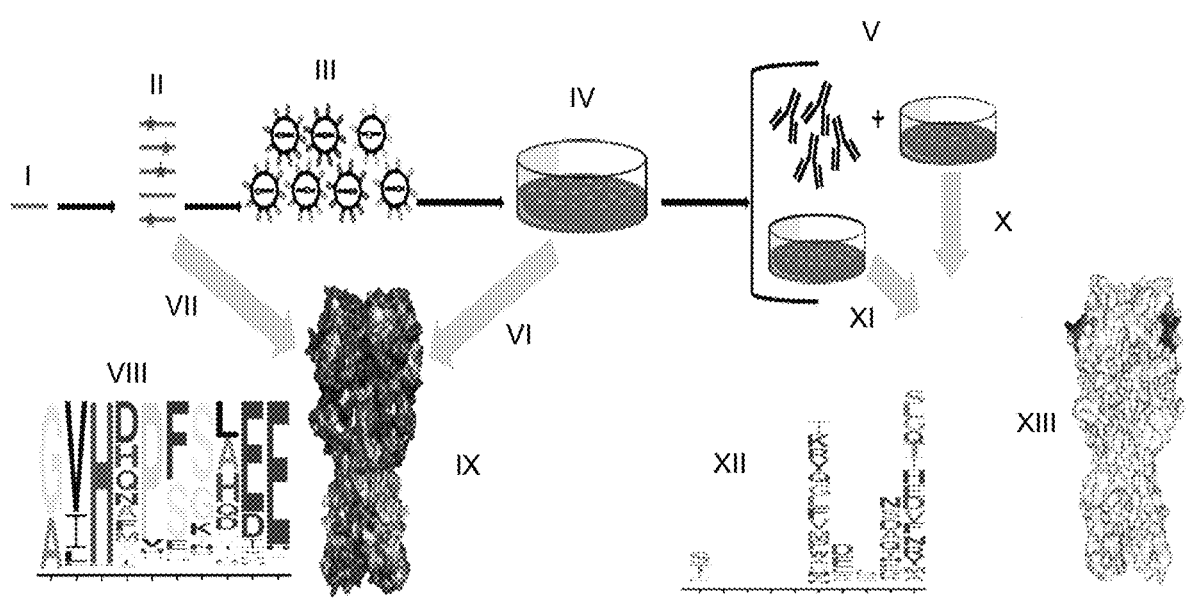
FIG. 1. Prior approach to measure the effects of all amino acid mutations to influenza viral entry protein, hemagglutinin (HA). All codon mutants (II) of wild type HA gene (I) were created and influenza viruses carrying these mutants were generated (III). The viruses were passaged in cell culture to select functional variants (IV) and treated with antibody to select antigenic mutants (top part of V). No treatment with antibody is used as a control (bottom part of V). Deep sequencing passaged viruses (VI) versus the initial mutant pool (VII) quantified the functional effect of each mutation. The letter height in the logo plot of VIII is proportional to preference for that amino acid. A representative structure (IX) is shaded by mutational tolerance from low (lighter gray) to high (darker gray). Data from Doud & Bloom, Viruses 8: 155 (2016). Deep sequencing of antibody-selected viruses (X) versus a control (XI) quantified the antigenic effect of each mutation. The letter height in the logo plot of XII is proportional to immune selection for that mutation. A representative structure (XIII) is shaded by immune selection from weak (lighter gray) to strong (darker gray). Data from Doud, et al. (2017) PLoS Pathog. 13(3): e1006271.

Influenza virus's rapid evolution poses a major challenge for the design of long-lasting vaccines, since the virus evolves to escape the pre-existing immunity elicited by prior infections or vaccinations (Bedford et al., Nature 523(7559), 217-20 (2015). Understanding how mutations affect the influenza virus's inherent fitness and its antigenicity is therefore important for forecasting viral evolution for vaccine-strain selection (uksza & Lässig, Nature 507, 57-61 (2014)) and guiding the development of vaccines (Krammer, Nat. Rev. Immunol. 19, 383-397 (2019)) and antivirals (Koszalka et al., Influenza Other Respi. Viruses 11(3), 240-46 (2017)).

Deep mutational scanning is a powerful new approach for measuring the effects of large numbers of mutations (Fowler & Fields, Nat. Methods 11(8), 801-7 (2014)). Deep mutational scanning has been applied to measure how mutations to influenza virus affect viral growth in cell culture (Doud & Bloom, *Viruses,* 8(6), 1-17 (2016); Wu et al., Sci. Rep. 4, Article No. 4942 (2014); Lee et al., Proc. Natl. Acad. Sci. USA (2018), doi:10.1073/pnas.1806133115), viral neutralization by antibodies (Doud et al., PLoS Pathog. 13 (2017), doi:10.1371/journal.ppat.1006271), and viral neutralization by polyclonal human sera (Lee et al., Mapping person-to-person variation in viral mutations that escape polyclonal serum targeting influenza hemagglutinin, 1-28 (2019)). This work can advance the aforementioned goals of improving forecasting of viral evolution and guiding the development of vaccines and antivirals.

However, deep mutational scanning of influenza virus remains expensive and laborious and cannot investigate the effects of multiple mutations separated by a large distance in primary sequence. The reason is that current approaches (including all of the studies cited in the previous paragraph) rely on short-read Illumina sequencing of the entire viral gene in each experiment. In this approach, influenza proteins have been barcoded using a subamplicon approach in which unique DNA barcodes are added by PCR during the sequencing library preparation stage (Hiatt et al., *Nature Methods,* 7(2), 119-122 (2010); Wu et al., *Journal of Virology,* 88(17), 10157-10164 (2014); Doud & Bloom *Viruses,* 8(6), 1-17 (2016)). Because influenza proteins are up to 1.9 kb in length, much greater than the longest possible Illumina read length, multiple subamplicons are required to cover an entire influenza gene. This is costly from a reagent, sequencing, and personnel-hours standpoint. It also prevents study of genes with multiple mutations separated by large distances in primary sequence.

Recently, deep mutational scanning of non-viral genes has been greatly improved by new approaches that involve linking a short random-nucleotide barcode to the full gene variant (Hiatt et al., *Nature Methods,* 7(2), 119-122 (2010); Starita et al., *Genetics,* 200(2), 413-422 (2015); Kitzman, et al., *Nature Methods,* 12(3), 203-206 (2015)). Barcoding influenza segments in their native viral context would reduce costs and labor. Barcodes could be linked to individual variants with long-read sequencing in DNA plasmid samples, and Illumina sequencing of barcodes alone in downstream selection steps would allow for the measurement of the effects of mutations on viral fitness. Similar approaches in non-viral systems have been used (Kitzman et al., Nat. Methods 12(3) 203-6 (2015); Starita, et al., American Journal of Human Genetics 103, 498-508 (2018)). But such approaches have not been successfully applied to influenza virus. This is because prior influenza virus barcoding or tagging strategies disrupted genome structure or function (Varble et al., Cell Host Microbe (2014), 16(5), 691-700 (2014); Heaton et al., Proc. Natl. Acad. Sci. USA 110(50), 20248-20253 (2013)), and thus were not amenable to barcoding unmutated viral genes in their wildtype genomic context.

The inability to barcode the entire influenza virus genome without affecting genome function is thought to be due to the highly constrained genome packaging mechanism (Hutchinson et al., J. Gen. Virol. 91(2) (2010), doi:10.1099/vir.0.017608-0). Prior work, however, has shown that the constraint on influenza virus packaging signal regions (Hutchinson et al., J. Gen. Virol. 91(2) (2010)) can be decoupled from the coding sequences by duplicating viral packaging signals (Gao & Palese, *Proceedings of the National Academy of Sciences of the U.S.A.,* 106(37), 15891-15896 (2009); Harding et al., *MBio,* 8(3), 1-16 (2017)).

Figure 2B:
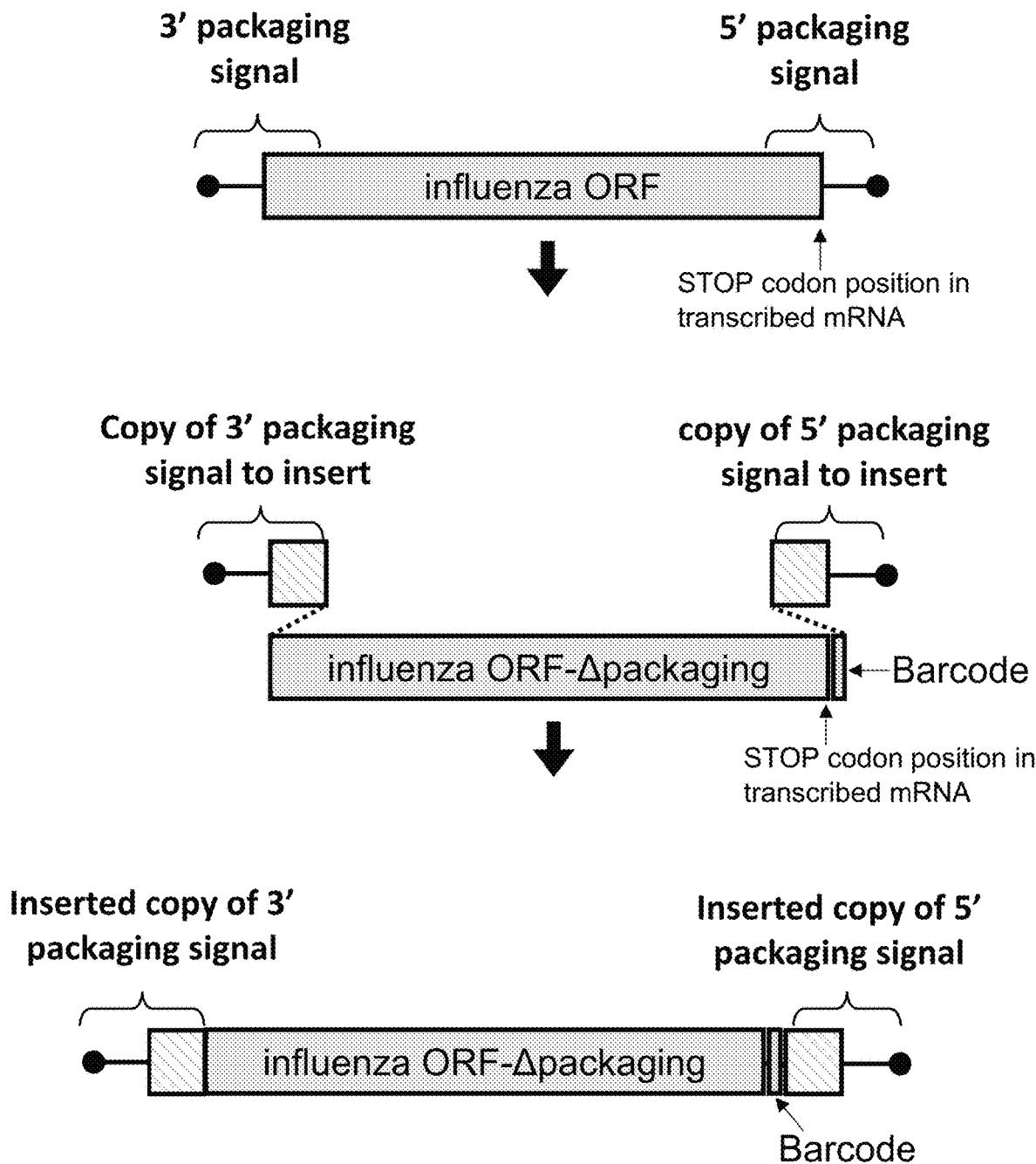

The current disclosure demonstrates that (i) duplicating and inserting a copy of the 5' vRNA packaging signal between the end of the corresponding viral genome segment's open reading frame (ORF) (corresponding to the stop codon of the transcribed positive sense mRNA) and the naturally occurring 5' vRNA packaging signal; and (ii) inserting the nucleic acid barcode between the end of the viral genome segment's ORF (corresponding to the stop codon of the transcribed positive sense mRNA) and the inserted copy of the 5' vRNA packaging signal allows insertion of a nucleic acid barcode into the influenza viral genome without disrupting the function of the viral proteins and the proper packaging of the viral genome segments. In other words, the systems and methods disclosed herein are selectively neutral with minimal to no effects on viral fitness. This approach is depicted schematically in FIG. 2A. In particular embodiments, 5' and 3' packaging signals that are duplicated and inserted are the particular 5' and 3' packaging signals that naturally occur at the 5' and 3' ends of an ORF in a given viral genome segment (referred to as the corresponding viral genome segment). Particular embodiments additionally include duplicating and inserting a copy of the 3' vRNA packaging signal before the beginning of the corresponding viral genome segment's open-reading frame (corresponding to the start codon of the transcribed positive sense mRNA). In particular embodiments, the inserted copy of the 3' vRNA packaging signal is between the beginning of the viral genome segment's open-reading frame (corresponding to the start codon of the transcribed positive sense mRNA) and the naturally occurring non-coding portion of the 3' vRNA packaging signal. This feature is depicted in FIG. 2B. In particular embodiments, codons in duplicated 3' packaging signals (corresponding to the start codons in the transcribed positive sense mRNA) can be removed or mutated. In particular embodiments, codons in duplicated 3' packaging signals (corresponding to the start codons in the transcribed positive sense mRNA) can be removed or mutated to ensure that translation of the viral protein initiates at the start codon of the ORF. In particular embodiments, nucleotides within a coding region of a viral genome segment can be mutated such that the same amino acid is encoded (synonymous mutations). In particular embodiments, nucleotides within the non-coding portion of the endogenous 5' or 3' packaging signal can be mutated. In particular embodiments, nucleotide mutations within a coding region of a viral genome segment and/or within the non-coding portion of the endogenous 5' or 3' packaging signal can improve packaging of the vRNA genome segment and/or improve expression of the viral protein encoded by the ORF in the vRNA genome segment.

Within the current disclosure, "selectively neutral" and "with minimal to no effects on viral fitness" can be used interchangeably. That insertion of a barcode is selectively neutral can be validated by creating a pool of viruses with different barcodes and passaging them at least two times in cell culture to demonstrate that no barcode increases or decreases in frequency by more than 2-fold after correcting for statistical sampling error (see, e.g., FIG. 4).

Depending on the particular influenza virus strain and genome segment, the duplicated packaging signal sequences include 50-200 nucleotides (Gerber, et al., Trends Microbiol. 22: 446-455 (2014); Hutchinson, et al., J. Gen. Virol. 91: 313-328 (2010)). For example, the packaging signal for NP vRNA of influenza A includes 120 nucleotides at the 5' end and 60 nucleotides at the 3' end of the coding region, in addition to the noncoding regions (Ozawa, et al., J. Virol 81: 30-41 (2006)). Packaging signals for other influenza A virus segments have also been identified (Gao, et al., J. Virol. 86: 7043-7051 (2012)). SEQ ID NOs. 1-4 provide exemplary packaging signals for the 5' end for Influenza A virus Segment 4, the 3' end for Influenza A virus Segment 4, the 5' end for Influenza A virus Segment 6, and the 3' end for Influenza A virus Segment 6, respectively. However, as will be understood by one of ordinary skill in the art, a packaging signal can refer to the shortest sequence required to allow packaging of vRNA. In particular embodiments, the packaging signal includes 50 nucleotides, 60 nucleotides, 70 nucleotides, 80 nucleotides, 90 nucleotides, 100 nucleotides, 110 nucleotides, 120 nucleotides, 130 nucleotides, 140 nucleotides, 150 nucleotides, 160 nucleotides, 170 nucleotides, 180 nucleotides, 190 nucleotides, or 200 nucleotides from the 5' or 3' end of a vRNA genome segment. In particular embodiments, the packaging signal includes 50 nucleotides-60 nucleotides, 60 nucleotide 70 nucleotides, 70 nucleotides-80 nucleotides, 80 nucleotides-90 nucleotides, 90 nucleotides-100 nucleotides, 100 nucleotides-110 nucleotides, 110 nucleotides-120 nucleotides, 120 nucleotides-130 nucleotides, 130 nucleotides-140 nucleotides, 140 nucleotides-150 nucleotides, 150 nucleotides-160 nucleotides, 160 nucleotides-170 nucleotides, 170 nucleotides-180 nucleotides, 180 nucleotides-190 nucleotides, or 190 nucleotides-200 nucleotides from the 5' or 3' end of the vRNA genome segment. In particular embodiments, a range of nucleotides for a packaging signal from the 5' or 3' end of a vRNA genome segment includes a portion of coding region of a vRNA genome segment and a portion of non-coding region adjacent to the coding region.

Figure 3:
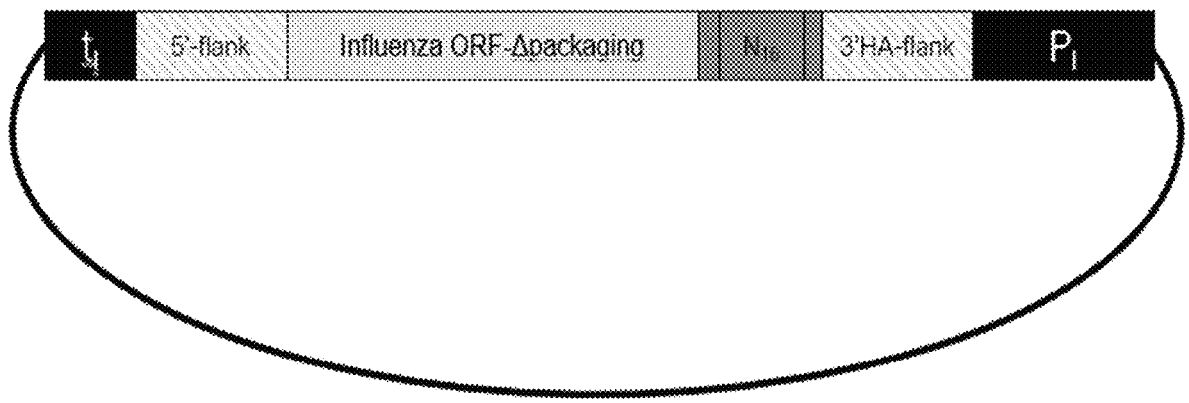
FIG. 3. Depiction of a plasmid barcoded according to methods of the current disclosure.

As indicated, the barcode of the systems and methods disclosed herein is inserted between the end of the viral genome segment's ORF (corresponding to the stop codon of the transcribed positive sense mRNA) and the inserted copy of the 5' vRNA packaging signal. Exemplary ORF coding sequences are depicted in FIG. 9, SEQ ID NOs. 5-36. These sequences provide guidance regarding ORFs, the start and stop codons of the coding sequences, non-coding regions 5' and 3' of an ORF, and exemplary packaging signals. FIG. 3 depicts an exemplary plasmid barcoded according to methods of the current disclosure.

Exemplary plasmids of the disclosure can be derived from cloning plasmids such as pUC18 or pUC19 plasmids (Norrander et al. Gene. 1983 December; 26(1):101-106). Exemplary plasmids of the disclosure include plasmids that allow transcription of negative sense vRNA from each of the eight genomic segments of influenza virus (FIG. 3). In particular embodiments, the plasmids can include a promoter, a barcoded vRNA genome segment, and a terminator sequence. In particular embodiments, the promoter in the plasmid can include a truncated human polymerase I promoter. A truncated human polymerase I promoter includes nucleotides −250 to −1 of the human polymerase I promoter. In particular embodiments, the barcoded vRNA genome segment in a plasmid is oriented such that transcription from the promoter results in production of negative sense vRNA genome segments. A barcoded vRNA genome segment in a plasmid includes barcoded, double stranded complementary DNA (cDNA) that has been reverse transcribed and amplified from the negative sense vRNA genome segment. In particular embodiments, a barcoded vRNA genome segment in a plasmid includes non-coding regions 5' and 3' to the coding region of the vRNA genome segment. Transcription plasmids include a terminator sequence to ensure that the transcribed positive sense mRNA has a proper 3' end. In particular embodiments, the terminator sequence can be derived from a hepatitis delta virus ribozyme sequence or a mouse RNA polymerase I terminator.

In particular embodiments, exemplary plasmids of the disclosure can also include plasmids that allow expression of a set of viral proteins required for encapsidation, transcription, and replication of the viral genome. The set of viral proteins required for encapsidation, transcription, and replication of the viral genome includes the three subunits of the viral RNA-dependent RNA polymerase complex (PB1, PB2, and PA) and the nucleoprotein (NP). Expression plasmids can include a promoter to drive expression of PB1, PB2, PA, and NP proteins encoded by corresponding cloned cDNA. PB1, PB2, PA, and NP proteins can amplify and transcribe (into mRNA) the negative sense vRNA produced from the plasmids described above. Promoters that can drive expression of PB1, PB2, PA, and NP proteins include mouse hydroxymethylglutaryl-coenzyme A reductase (HMG) promoter, adenovirus type 2 major late promoter, the cytomegalovirus (CMV) promoter, and chicken β-actin promoter.

In particular embodiments, exemplary plasmids of the present disclosure can be ambisense expression plasmids. Ambisense expression plasmids are bidirectional plasmids that allow both transcription of a negative sense vRNA and expression of the recombinant viral protein encoded by the ORF from that vRNA. In particular embodiments, an ambisense plasmid can include cDNA that has been reverse transcribed and amplified from a negative sense vRNA genome segment. In particular embodiments, an ambisense plasmid can include non-coding regions 5' and 3' to the coding region of the vRNA genome segment. In one direction of the plasmid, a polymerase I transcription cassette (e.g., viral cDNA between human RNA polymerase I promoter and a mouse terminator sequence) allows production of negative sense vRNA. In the opposite direction, a polymerase II transcription cassette (viral cDNA between chicken β-actin promoter and polyA) encodes the viral protein encoded by the same vRNA genome segment. An example of an ambisense plasmid is described in Martinez-Sobrido and Garcia-Sastre J Vis Exp. 2010; 42: 2057. Transfection of appropriate plasmids into a cell line allows intracellular reconstitution of ribonucleoprotein complexes that include barcoded genome segments for production of barcoded influenza viruses.

An exemplary protocol for transfection of plasmids containing barcoded vRNA genome segments of the present disclosure is briefly described. A plasmid transfection mixture including appropriate media (e.g., Opti-MEM™ media, Thermo Fisher Scientific, Waltham, MA), plasmids containing barcoded vRNA genome segments, and a transfection agent (e.g., Lipofectamine) can be prepared. The plasmid transfection mixture can then be incubated with cell lines to be transfected (e.g., 293T and/or MDCK cells) for a period of time (e.g., overnight) under appropriate conditions (e.g., 37° C. and 5% $CO_2$). The media can be changed during the transfection period. Supernatant from transfected cells can be used to infect fresh cell lines (or chicken embryonated eggs) for a period of time (e.g., 37° C. for 2 to 3 days). For cell lines, a cytopathic effect can be seen at a period of time (e.g., 48-72 hours) after passage of the cells and can suggest successful rescue of barcoded virions. A hemagglutination (HA) assay and/or immunofluorescence assays can be performed to detect the presence of rescued virus in cell culture supernatant or in the allantoic fluid of harvested eggs. In an HA assay, the presence of virus induces hemagglutination of red blood cells, while the absence of virus allows the formation of a red pellet in the bottom of the well. Immunofluorescence assays can make use of sera that recognize a viral antigen and fluorescently labeled secondary antibodies. Once an assay identifies the presence of rescued virus, the virus can be plaque purified, and the genetic composition of the virus can be confirmed by RT-PCR and sequencing.

The barcoded influenza viruses described herein can be used to create deep mutational scanning libraries for the study of influenza virus proteins. Within these libraries, in particular embodiments, each variant carries a unique barcode. The selectively neutral barcodes can be linked to the viral mutations by long-read sequencing. Thereafter, the functional and antigenic effects of viral mutations (both singly and in combination) can be easily read out by sequencing the barcodes. This approach greatly improves the power and accuracy of deep mutational scanning of influenza virus genes.

Variant libraries generated using methods disclosed herein have numerous applications. In particular embodiments, the systems and methods disclosed herein can be used to map the epitopes of influenza-virus binding antibodies; to inform antibody drug development by characterizing mutations in target viral proteins that allow development of influenza resistance to antibodies; and/or to assess the ability of different influenza virus entry proteins to evade antibody neutralization, overcome drug inhibition, and/or infect new species. If numerous mutations to the viral entry protein allow antibody evasion, drug resistance, and/or infection of a new host species, the viral strain may have a higher probability of becoming a health threat. If, however, only few or very specific mutations allow antibody evasion, drug resistance, and/or infection of a new host species, the viral strain may pose less of a threat.

In particular embodiments, deep mutational scanning combines functional selection with high throughput sequencing to measure the effects of mutations on protein function. In particular embodiments, a library of $10^4$ to $10^5$ variants of a given protein is constructed and selection for function is imposed. Under modest selection pressure, variant frequencies are perturbed according to the function of each variant. Variants harboring beneficial mutations increase in frequency, whereas variants harboring deleterious mutations decrease in frequency. In particular embodiments, high throughput sequencing can measure the frequency of each variant during the selection experiment, and a functional score can be calculated from the change in frequency over the course of the experiment. In particular embodiments, the result is a largescale mutagenesis data set containing a functional score for each variant in the library. Fowler et al. Nature Protocols 9: 2267-2284 (2014). As one example, in particular embodiments, sera samples can be obtained from vaccine studies to map mutations that affect resistance to these sera. This work can functionally map the epitopes targeted by the vaccines and enable correlation of animal-to-animal variation in protection with variation in epitope targeting, both of which could help inform further immunogen design.

The deep mutational scanning libraries disclosed herein can also include absolute standards. These absolute standards can be based on viruses with glycoproteins that are not recognized by a species of interest. For example, in particular embodiments, the absolute standards can be based on viruses with glycoproteins not from human influenza strains that are not recognized by human sera or antibodies. With the inclusion of such absolute standards, selection on mutations can be quantified in high-throughput mode.

Figure 4:
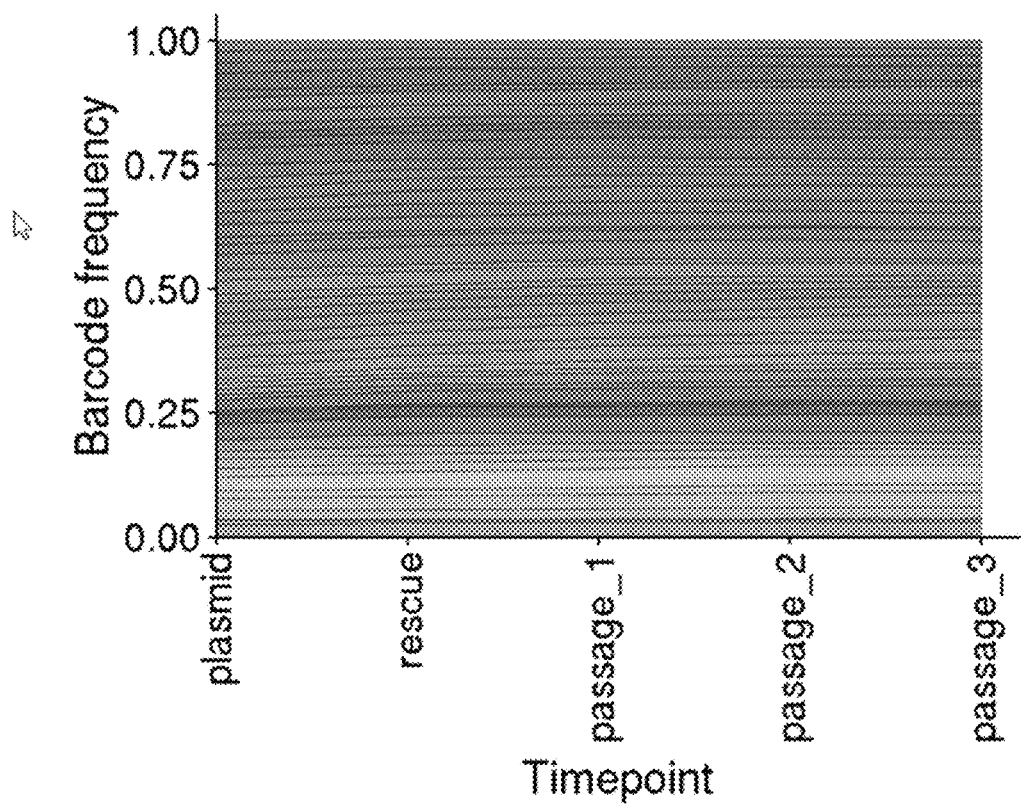
FIG. 4. Data demonstrating that the barcoding strategies described herein are selectively neutral and have minimal effects on viral fitness.

Systems and methods disclosed herein have been utilized to successfully create a barcoded deep mutational scanning library of the neuraminidase segment with >200,000 unique barcodes per library. Libraries of barcoded wild type HA and NA gene segments have also been generated with 50 to >1 million barcodes. The barcodes did not affect viral fitness as shown in FIG. 4.

Aspects of the current disclosure are now described with additional detail and options as follows: (i) Influenza Virus; (ii) Barcoded Deep Mutational Scanning Libraries; (iii) Exposure to Selection Pressures; (iv) Engineering More Effective Antibodies; (v) Selection of Effective Anti-Viral Conditions and/or Effective Therapeutic Compounds; (vi) Host Adaptation Studies; (vii) Kits; (viii) Exemplary Embodiments; (ix) Experimental Examples; and (x) Closing Paragraphs. As will be understood by one of ordinary skill in the art, information within each of the disclosure sub-headings can apply to information within other sub-headings, and the sub-headings are provided only for organizational convenience.

(i) Influenza Virus. The influenza virus belongs to the Orthomyxoviridae family, which are enveloped viruses with single-stranded, negative-sense RNA genomes. The types of influenza viruses include: influenza A virus, influenza B virus, influenza C virus, and influenza D virus.

Influenza A viruses can infect humans and a variety of animals, such as pigs, horses, marine mammals, cats, dogs, and birds and therefore poses a significant risk of zoonotic infection, host switch, and the generation of pandemic viruses. Some well-known flu pandemics include: the 1918 H1N1 Spanish flu, the 1957 H2N2 Asian flu, the 1968 H3N2 Hong Kong flu, and the 2009 H1N1 swine flu (Shao, et al., Int. J. Mol. Sci. 18(8): 1650 (2017)). Influenza C is associated with mild respiratory illness and is not thought to cause epidemics or pandemics. Thus far, influenza D viruses have only been found to affect swine and cattle and therefore are not known to cause illness in humans. Therefore, influenza D viruses could be used as absolute standards within screening libraries described herein.

The influenza A virus and influenza B virus have an eight-segmented viral RNA (vRNA) genome, whereas influenza C virus has a seven-segmented vRNA genome. Although recently isolated, influenza D virus is believed to have a seven-segmented vRNA genome (Nakatsu, et al., J. Virol 92(6): e02084-17 (2018)). Despite this, Nakatsu, et al. found that influenza viruses, including influenza C virus and influenza D virus, package eight ribonucleoprotein complexes (RNPs) regardless of RNA segments in their genome. These vRNA segments encode viral proteins.

The influenza A virus genome is 13 kb and encodes 13 proteins (Jagger et al., Science. 337:199-204 (2012)) including: hemagglutinin (HA), neuraminidase (NA), M1 matrix protein (M1), M2 ion channel protein (M2), nuclear protein (NP), nonstructural protein (NS1, NS2 (NEP)), and RNA polymerase complex (PB1, PB2, PA) (Cox et al., 2000 Annu. Rev. Med. 51:407-421). Additional viral proteins expressed by splicing, alternative initiation, or ribosomal frameshifts from the eight segments include PB1-F2, PB1-N40, and PA-X (Muramoto et al. Journal of Virology 2013; 87(5): 2455-2462. The influenza B virus differs in that instead of an M2 protein, it has a BM2 protein and has a viral segment with both NA and NB sequences.

Influenza A viruses can be divided into subtypes on the basis of their surface glycoproteins, HA and NA. There are 18 HA subtypes and 11 NA subtypes. Influenza A viruses can be further classified by strains, such as the influenza A (H1N1) and influenza A (H3N2) viruses. Influenza B and C viruses can be classified by lineage or by strains (Hay et al., Philos. Trans. R. Soc. Lond. B. Biol. Sci. 356:1861-1870 (2001); Aoyama, et al., Virology. 1991; 182:475-485 (1991)).

The Influenza A genes encoding the viral surface proteins, HA and NA, that form the main targets of neutralizing antibodies, are critical for the evolution of the virus. All known influenza A viruses have been found in birds, except subtypes H17N10 and H18N11 which have only been found in bats. Human influenza A viruses have only been detected with the subtypes of HA, including H1, H2, H3, H5, H6, H7, H9, and H10 and subtypes of NA, including N1, N2, N6, N7, N8, and N9. In swine, the detected HA subtypes include: H1, H2, H3, H4, H5, and H9 with the detected NA subtypes including: N1 and N2. Other animals have been found with the HA subtypes: H3, H4, and H7 and NA subtypes N7 and N8.

The life cycle of influenza virus can be briefly described as follows. Influenza virions (the complete, infective form of a virus outside a host cell, with a core of RNA and a capsid) enter the host cell, where their negative sense RNA is released into the cytoplasm. The virus' own RNA replicase, known as RNA-dependent RNA polymerase (RdRp), is used to form positive sense RNA template strands through complementary base pairing. There are two forms of positive sense RNA: one serves as messenger RNA (mRNA), which is translated into viral proteins by ribosomes of the host cell; the other serves as template to make more negative sense RNA strands. In viruses with segmented genomes like influenza virus, replication occurs in the nucleus and the RdRp produces one monocistronic mRNA strand (encoding one polypeptide per RNA molecule) from each genome segment. New viral capsids are assembled with the capsomere proteins. The negative sense RNA strands combine with capsids and viral RdRp to form new negative sense RNA virions. After assembly and maturation of nucleocapsid, the new virions exit the cell through the cell membrane by budding or lysis to further infect other cells.

The influenza genome is packaged into progeny virions by cis-acting, segment-specific packaging signals found on each vRNA. These packaging signals include bipartite sequences at the 5' and 3' ends of the vRNA, which house not only conserved promoter sequences but also coding and segment-specific non-coding regions adjacent to the promoter region. Each packaging signal is unique to each vRNA, and it has been shown that the 5' sequence is more important than the 3' sequence for genome packaging, and that a longer 5' sequence is better for genome packaging. In addition, studies have shown that nucleotide length is important, but the actual sequence is less so (random sequences are sufficient to generate viruses).

As indicated previously, representative packaging signal sequences and genome segments are provided in FIG. 9 as SEQ ID NOs. 1-36.

(ii) Barcoded Deep Mutational Scanning Libraries. Barcoded deep mutational scanning libraries described herein include barcoded influenza virus. In particular embodiments, a deep mutational scanning library includes influenza protein variants with 19 possible amino acid substitutions at each amino acid position and all possible codons of the associated 63 codons at each amino acid position of an influenza viral protein under analysis. In particular embodiments, a deep mutational scanning library includes influenza protein variants with every possible codon substitution at every amino acid position in a gene of interest with one codon substitution per library member. A deep mutational scanning library can also include variants with one, two, or three nucleotide changes for each codon at every amino acid position in a gene of interest with one codon substitution per library member. A deep mutational scanning library can also include variants with one, two, or three nucleotide changes for each codon at two amino acid positions, at three amino acid positions, at four amino acid positions, at five amino acid positions, at six amino acid positions, at seven amino acid positions, at eight amino acid positions, at nine amino acid positions, at ten amino acid positions, etc., up to at all amino acid positions, in a gene of interest with one codon substitution per library member. In particular embodiments, the start codon is not mutagenized. In particular embodiments, the start codon is Met.

In particular embodiments, a deep mutational scanning library includes variants with one, two, or three nucleotide changes for each codon at every amino acid position in a gene of interest with more than one codon substitution, more than two codon substitutions, more than three codon substitutions, more than four codon substitutions, or more than five codon substitutions, per library member. In particular embodiments, a deep mutational scanning library includes variants with one, two, or three nucleotide changes for each codon at every amino acid position in a gene of interest with up to all codon substitutions per library member. In particular embodiments, 20% of library members can be wildtype, 35% can be single mutants, and 45% can be multiple mutants. Multiple mutants can be advantageous, and the sequencing required by the systems and methods disclosed herein is so efficient that using 20% of reads on wildtype is not a problem. Additionally, there are alternative (more complex) mutagenesis methods that give a larger proportion of single amino acid mutants [see, e.g., Kitzman, et al. (2015) Nature Methods 12: 203-206; Firnberg & Ostermeier (2012) PLoS One 7: e52031; Jain & Varadarajan (2014) Analytical Biochemistry 449: 90-98; and Wrenbeck, et al. (2016) Nature Methods 13: 928].

In particular embodiments, a deep mutational scanning library includes or encodes all possible amino acids at all positions of a protein, and each variant protein is encoded by more than one variant nucleotide sequence. In particular embodiments, a deep mutational scanning library includes or encodes all possible amino acids at all positions of a protein, and each variant protein is encoded by one nucleotide sequence. In particular embodiments, a deep mutational scanning library includes or encodes all possible amino acids at less than all positions of a protein, for example at 10%, 20%, 30%, 40%, 50%, 60%, 70%, 80%, 90%, 95%, 96%, 97%, 98% or 99% of positions. In particular embodiments, a deep mutational scanning library includes or encodes less than all possible amino acids (for example 10%, 20%, 30%, 40%, 50%, 60%, 70%, 80%, 90%, 95%, 96%, 97%, 98% or 99% of potential amino acids) at all positions of a protein. In particular embodiments, a deep mutational scanning library includes or encodes less than all possible amino acids (for example 10%, 20%, 30%, 40%, 50%, 60%, 70%, 80%, 90%, 95%, 96%, 97%, 98% or 99% of potential amino acids) at less than all positions of a protein, for example at 10%, 20%, 30%, 40%, 50%, 60%, 70%, 80%, 90%, 95%, 96%, 97%, 98% or 99% of positions. A deep mutational scanning library can also include a set of variant nucleotide sequences that can collectively encode protein variants including at least a particular number of amino acid substitutions at at least a particular percentage of amino acid positions. "Collectively encode" takes into account all amino acid substitutions at all amino acid positions encoded by all the variant nucleotide sequences in total in a deep mutational scanning library. Libraries created using the methods described herein can also encode mutations at a pre-determined subset of sites within a protein of interest.

In particular embodiments, a codon-mutant library can be generated by PCR, primer-based mutagenesis, as described in Example 1 and in US2016/0145603. Codon-mutant libraries can also be synthetically constructed by and obtained from a synthetic DNA company such as Twist Bioscience (San Francisco, CA). Methods to generate a codon-mutant library also include: nicking mutagenesis as described in Wrenbeck et al. Nature Methods 13: 928-930 (2016) and Wrenbeck et al. Protocol Exchange doi:10.1038/protex.2016.061 (2016); PFunkel (Firnberg & Ostermeier PLoS ONE 7(12): e52031 (2012)); massively parallel single-amino-acid mutagenesis using microarray-programmed oligonucleotides (Kitzman et al. Nature Methods 12: 203-206 (2015)); and saturation editing of genomic regions with CRISPR-Cas9 (Findlay et al. Nature 513 (7516): 120-123 (2014)).

Supporting the description of creating codon-mutant libraries, the following information is provided for viral entry proteins for influenza. Hemagglutinin (HA) is 566 codons long, so there are 566×63=35,658 codon mutations corresponding to 566×19=10,754 amino acid mutations. The number of mutations per clone from the mutagenesis method follows a Poisson distribution, and an average of 1.5 mutations can be introduced per clone and libraries of $5 \times 10^5$ clones can be created. Therefore, $1.7 \times 10^5$ of the clones will be single mutants, and $2.2 \times 10^5$ will be multiple mutants. The typical single-codon mutant will thus be represented by 5 clones, and with Poisson statistics 99% of single-codon mutants should be captured in at least one clone. The typical single amino acid mutant will be represented by 15 clones, although this will vary among amino acids with different codon degeneracies. In particular embodiments, HA from A/Perth/16/2009 (H3N2), a recent component of the influenza vaccine can be used to generate a codon-mutant library with barcodes for HA.

Each variant sequence can be associated with a barcode. In particular embodiments, the barcode is 18-nucleotides in length. Because there are $4^{18}$-$7^{10}$ different 18-nucleotide sequences, virtually every variant can have a unique barcode. The barcode can be any appropriate length and composition that does not negatively affect fitness of the encoded variant protein. In particular embodiments, the length of the barcode is based upon the size of the deep mutation scanning library. If more distinct barcodes are needed, then barcodes of greater length can be used. If less distinct barcodes are needed, then barcodes of lesser length can be used. In particular embodiments, the barcode can be 5-100 nucleotides in length, 10-80 nucleotides in length, 10-50 nucleotides in length, 8-30 nucleotides in length, 12-24 nucleotides in length, or 16-20 nucleotides in length. In particular embodiments, the barcode can be 3 nucleotides in length, 4 nucleotides in length, 5 nucleotides in length, 6 nucleotides in length, 7 nucleotides in length, 8 nucleotides in length, 9 nucleotides in length, 10 nucleotides in length, 11 nucleotides in length, 12 nucleotides in length, 13 nucleotides in length, 14 nucleotides in length, 15 nucleotides in length, 16 nucleotides in length, 17 nucleotides in length, 18 nucleotides in length, 19 nucleotides in length, 20 nucleotides in length, 21 nucleotides in length, 22 nucleotides in length, 23 nucleotides in length, 24 nucleotides in length, 25 nucleotides in length, 26 nucleotides in length, 27 nucleotides in length, 28 nucleotides in length, 29 nucleotides in length, 30 nucleotides in length, 31 nucleotides in length, 32 nucleotides in length, 33 nucleotides in length, 34 nucleotides in length, 35 nucleotides in length, 36 nucleotides in length, 37 nucleotides in length, 38 nucleotides in length, 39 nucleotides in length, 40 nucleotides in length, or more.

After creating barcoded influenza viruses, each variant viral protein can be associated with its barcode. In particular embodiments, a high throughput sequencing method that can sequence long reads with high accuracy can be used to associate each viral protein variant with its barcode. For example, this can be conducted using circular consensus PacBio sequencing as described in Travers, et al. Nucleic Acids Research 38: e159-e159 (2010) and Laird Smith, et al. Virus Evolution 2: vew018 (2016). In particular embodiments, long reads can include greater than 100 bp, greater than 200 bp, greater than 300 bp, greater than 400 bp, greater than 500 bp, greater than 600 bp, greater than 700 bp, greater than 800 bp, greater than 900 bp, greater than 1000 bp, greater than 2000 bp, greater than 3000 bp, greater than 4000 bp, greater than 5000 bp, greater than 6000 bp, greater than 7000 bp, greater than 8000 bp, greater than 9000 bp, greater than 10,000 bp, or more. In particular embodiments, accuracy of a sequencing method is related to the sequencing method's error rate. A sequencing error rate can be expressed as a sequencing quality score of a given base, Q, defined by the following equation: $Q=-10 \log_{10}(e)$, where e is the estimated probability of the base call being wrong. Higher Q scores indicate a smaller probability of error. In particular embodiments, a Q score of 10 represents an error rate of 1 in 10 bases, and the inferred base call accuracy is 90%. A Q score of 20 can represent an error rate of 1 in 100 bases, and the inferred base call accuracy is 99%. A Q score of 30 can represent an error rate of 1 in 1000 bases, and the inferred base call accuracy is 99.9%. In particular embodiments, high accuracy includes having fewer systematic errors such as errors in base calling or read mapping/alignment and/or errors that are independent of the sequencing context. For example, a high throughput sequencing method that has errors independent of sequencing context would have the same error rate regardless if the sequence was AAAAAAAA (SEQ ID NO: 37) versus AAAAACAG (SEQ ID NO: 38). (DePristo et al. Nat Genet 43(5): 491-498 (2011); Roberts et al. Genome Biology 14:405 (2013). In particular embodiments, high accuracy includes 99.99% accuracy.

In particular embodiments, each influenza virus variant can be associated with its barcode by subassembly as described in U.S. Pat. No. 8,383,345. It can also be associated with its barcode by long-read PacBio or Oxford Nanopore sequencing. In particular embodiments, if the gene encoding a variant influenza protein is small, each gene encoding the protein variant can be associated with its barcode by a barcoded subamplicon approach as described above and in Doud & Bloom Viruses 8, 155 (2016).

(iii) Exposure to Selection Pressures. Following creation of an influenza virus barcoded deep mutational scanning library, members of the library can be exposed to a selection pressure to assess the variant virus' resistance or susceptibility to the selection pressure. A selection pressure can include any environmental condition that may affect a virus's function or survival. For example, the environmental condition may include exposure to a therapeutic compound or to heat. Numerous selection pressures are described in additional detail in this section.

In particular embodiments, the selection pressure is exposure to a compound that may have therapeutic efficacy against influenza infection. In particular embodiments, the compound is one that is described in, for example, U.S. Pat. Nos. 5,994,515, 9,259,433, US2009/0214510, US2017/0157190, WO2008/147427, WO2009/027057, WO2009/151313, WO2012/006596, WO2013/006795, WO2013/072917, and WO2014/062892; Laursen and Wilson (2013) Antiviral Res 98(3): 476-483; and Pelegrin et al. (2015) Trends in Microbiology 23(10): 653-665.

In particular embodiments, compounds for assessment can include anti-influenza virus antibodies such as TNX-355 (ibalizumab); PGT121 (Julien et al. (2013) PLoS Pathog 9(5): e1003342; broadly neutralizing antibody); and 3BNC117 (Scheid et al. (2016) Nature. 535: 556-560).

In particular embodiments, compounds can include viral entry and/or fusion inhibitors. Entry and fusion inhibitors can include, for example, highly sulfated polysaccharides from fucoidan or algae; calcium spirulan, nostoflan, or extract of *Scoparia dulcis*, or antiviral diterpene components contained therein, such as scoparic acid A, scoparic acid B, scoparic acid C, scopodiol, scopadulin, scopadulcic acid A (SDA), scopadulcic acid B (SDB), and/or scopadulcic acid C (SDC).

In particular embodiments, compounds can include influenza virus polymerase inhibitors, drugs that increase the viral mutation rate, drugs that interfere with function of the hemagglutinin or neuraminidase protein, and inhibitors that inhibit binding of an influenza virus genome to one or more nucleoproteins. In particular embodiments, compounds are directly or indirectly effective in specifically interfering with at least one influenza virus action including penetration of eukaryotic cells, replication in eukaryotic cells, virus assembly, release from infected eukaryotic cells, or that is effective in nonspecifically inhibiting a virus titer increase or in nonspecifically reducing a virus titer level in a eukaryotic or mammalian host system.

In particular embodiments, the selection pressure is a toxic agent. Toxic agents can include polar organic solvents (e.g., dimethylformamide), herbicides (e.g., glyphosate), pesticides (e.g., malathion, dichlorodiphenyltrichloroethane), salinity, ionizing radiation, and hormonally active phytochemicals (e.g., flavonoids, lignins and lignans, coumestans, or saponins).

In particular embodiments, deep mutational scanning libraries described herein can be used to perform influenza virus resistance analysis to therapeutic compounds. In these embodiments, influenza virus resistance to therapeutic compounds caused by mutations of given protein residues represented within the deep mutational scanning can be assessed.

In particular embodiments, in vitro resistance analysis studies can assess the potential ability of an influenza virus to develop resistance to a therapeutic compound and to help in designing clinical studies. Virus resistance to a given therapeutic compound can be selected in cell culture, and the selection can provide a genetic threshold for resistance development. For example, a therapeutic compound with a low genetic threshold may become susceptible to viral resistance with only one or two mutations. In contrast, a therapeutic compound with a high genetic threshold may require multiple mutations to become susceptible to viral resistance. Therapeutic compounds with higher genetic thresholds can be selected for further clinical development.

In particular embodiments, the development of viral resistance in vitro can be assessed over a concentration range of a therapeutic compound spanning the anticipated concentration of the therapeutic compound that will be used in vivo. Selection of variants resistant to a therapeutic compound can be repeated more than once (e.g., with different strains of wild-type, with resistant strains, under high and low selective pressures) to determine if the same or different patterns of resistance mutations develop, and to assess the relationship of therapeutic compound concentration to the resistance.

As discussed above, determining the mutations that might contribute to reduced susceptibility to a therapeutic compound using the systems and methods of the present disclosure can include sequencing barcodes after linking a barcode to a particular viral protein variant in a deep mutational scanning library. Identifying resistance mutations by this genotypic analysis can be useful in predicting clinical outcomes and supporting the proposed mechanism of action of a therapeutic compound. In particular embodiments, the pattern of mutations leading to resistance of a therapeutic compound can be compared with the pattern of mutations of other therapeutic compounds in the same class. In particular embodiments, resistance pathways can be characterized in several genetic backgrounds (i.e., strains, subtypes, genotypes) and protein variants can be obtained throughout the selection process to identify the order in which multiple mutations appear.

Phenotypic analysis determines if mutant viruses have reduced susceptibility to a therapeutic compound. In particular embodiments, using the systems and methods of the present disclosure, phenotypic analysis is performed when influenza virions including protein variants are selected for resistance to a therapeutic compound. In particular embodiments, phenotypic resistance can be scored, for example, by an $EC_{50}$ value. An $EC_{50}$ value can refer to an effective concentration of a therapeutic compound which induces a response halfway between the baseline and maximum after a specified exposure time. In particular embodiments, an $EC_{50}$ value can be used as a measure of a therapeutic compound's potency. $EC_{50}$ can be expressed in molar units (M), where 1 M is equivalent to 1 mol/L. The fold resistant change can be calculated as the $EC_{50}$ value of the variant protein/$EC_{50}$ value of a reference protein. Phenotypic results can be determined with any standard virus assay (e.g., protein assay, viral RNA assay, polymerase assay, MTT cytotoxic assay, reporter or selectable marker expression). In particular embodiments, influenza virus titer can be calculated as a function of the concentration of the therapeutic compound to obtain an $EC_{50}$ value. In particular embodiments, influenza virus titer can be calculated by a plaque assay or focus forming assay. A plaque assay takes advantage of plaques that can arise through influenza virus-mediated cell death within a monolayer of a cell culture when cells are infected with an influenza virus and typically requires plaques to grow until visible to the naked eye. The focus-forming assay can be used to titer non-cytopathic influenza viruses. This assay usually relies on the detection of infected cells by immunostaining for influenza virus antigen or via a genetically encoded fluorescent reporter. The shift in susceptibility (or fold resistant change) for a protein variant can be measured by determining the $EC_{50}$ value for the variant protein and comparing it to the $EC_{50}$ value of a reference protein. In particular embodiments, a reference protein can be a counterpart influenza viral protein (equivalent viral protein having the same function from the same viral strain) from a wild-type virus, from a well-characterized wild-type laboratory strain, from a parental virus, or from a baseline clinical isolate done under the same conditions and at the same time. In particular embodiments, a wild-type virus can be naturally occurring. In particular embodiments, a wild-type virus has no mutations that confer drug resistance. In particular embodiments, a parental virus can be an influenza virus having a viral protein that did not undergo mutagenesis as described herein to create a barcoded deep mutational scanning library of variants of the influenza viral protein. In particular embodiments, a parental virus can be a wild type virus. A baseline clinical isolate includes an isolate from a subject being screened for inclusion in a clinical trial or an isolate from a subject in a clinical trial before treatment in the trial has begun. The use of the $EC_{50}$ value for determining shifts in susceptibility can offer greater precision than an $EC_{90}$ or $EC_{95}$ value. The utility of a phenotypic assay depends on its sensitivity (i.e., its ability to measure shifts in susceptibility (fold resistance change) in comparison to a reference). Calculating the fold resistant change ($EC_{50}$ value of variant protein/$EC_{50}$ value of reference protein) allows for comparisons among phenotypic assays.

An influenza viral protein may develop mutations that lead to reduced susceptibility (i.e., resistance) to one antiviral therapeutic compound and can result in decreased or loss of susceptibility to other antiviral therapeutic compounds in the same therapeutic compound class. This observation is referred to as cross-resistance. Cross-resistance is not necessarily reciprocal, so it is important to evaluate both possibilities. For example, if influenza virus X is resistant to drug A and drug B, and influenza virus Y is also resistant to drug A, influenza virus Y may still be sensitive to drug B. In particular embodiments, the effectiveness of a therapeutic compound against influenza viruses resistant to other approved therapeutic compounds in the same class and the effectiveness of approved therapeutic compounds belonging to a given class against influenza viruses resistant to a therapeutic compound belonging to that same class can be evaluated by phenotypic analyses. In particular embodiments, cross-resistance can be analyzed between therapeutic classes in instances where more than one therapeutic compound class targets a single influenza virus protein or protein complex (e.g., neuraminidase inhibitor and polymerase inhibitor, such as oseltamivir and baloxivr). Variant influenza virus proteins representative of the breadth of diverse mutations and combinations of mutations known to confer reduced susceptibility to therapeutic compounds in the same class can be tested for phenotypic susceptibility to a new therapeutic compound belonging to that same class.

Figures 5A, 5B, 5C:
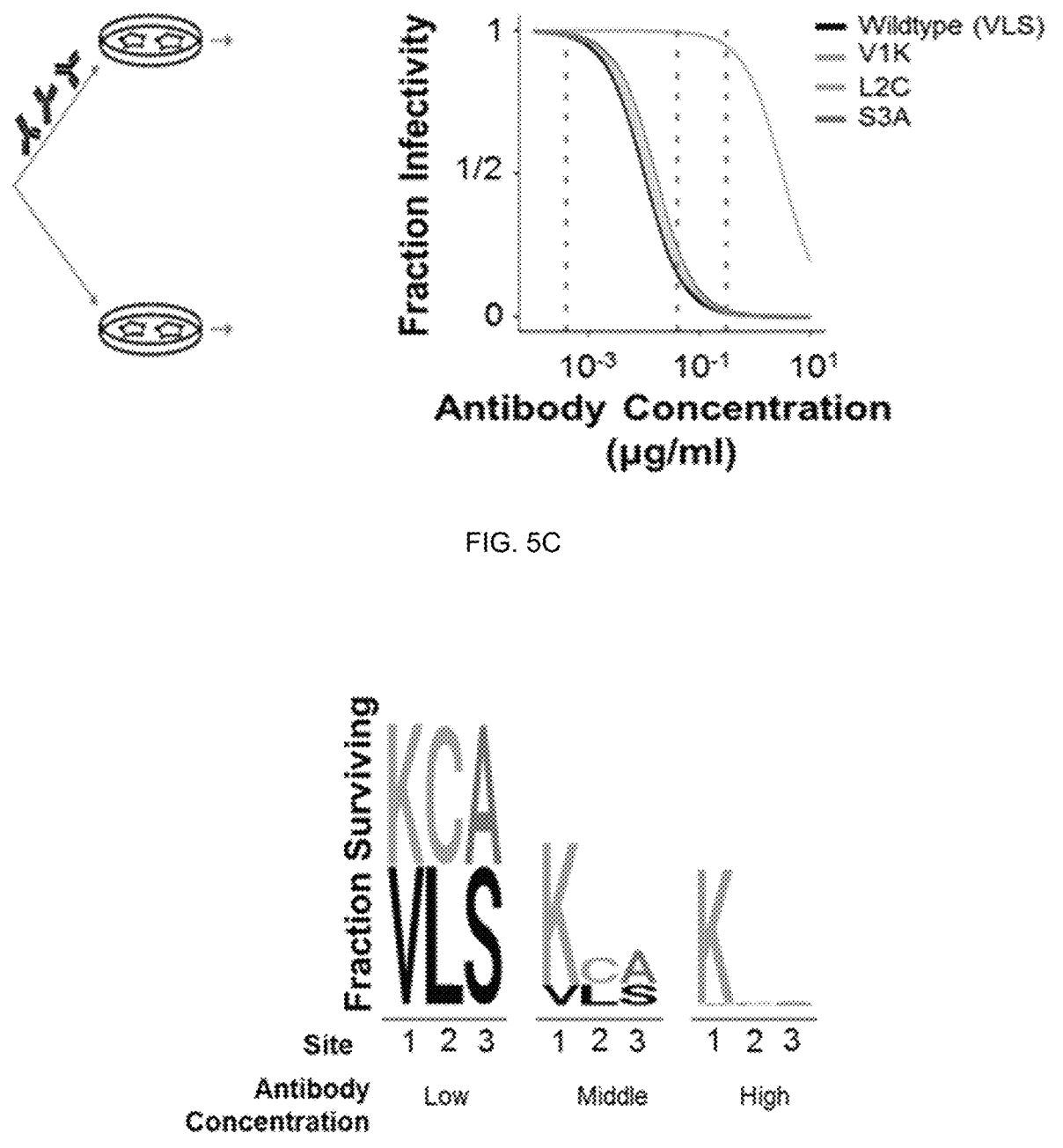

The sensitivity of a virus to an antibody or serum sample can be quantified by a neutralization curve (FIG. 5B). Such curves are conventionally measured on individual viral variants, but they can in principle be measured for many variants at once using deep sequencing. In prior work, deep sequencing of viral libraries has been used to measure antibody selection on viral mutations (Doud, et al. PLoS Pathog. 13(3): e1006271 (2017); Dingens et al., Cell Host & Microbe 21: 777-787 (2017); Doud et al. bioRxiv DOI: 210468 (2018)). Because these libraries were not barcoded, however, it was only feasible to use one or a few antibody concentrations. With the barcoded libraries disclosed herein, multiple concentrations to interpolate full curves can be tested. In particular embodiments, curves for >$10^4$ mutants can be generated. In these embodiments, it can be more informative to represent the results in logo plots rather than overlaying vast numbers of curves (FIG. 5C). In particular embodiments, a sequence logo plot can be a graphical representation of sequence conservation of nucleotides or amino acids. A sequence logo can be created from a collection of aligned sequences and depicts the consensus sequence and diversity of the sequences. In particular embodiments, sequence logos can be used to depict sequence characteristics such as protein-binding sites in DNA or functional units in proteins. In particular embodiments, sequence logos can be used to depict the preference for a nucleotide base or an amino acid residue at a given position in a nucleotide sequence or in an amino acid sequence, respectively. In particular embodiments, sequence logos can be used to depict the effect of each amino acid or nucleotide on a selective pressure, such as antibody neutralization or drug inhibition as described above.

In particular embodiments, to obtain neutralization curves, the absolute fraction of each influenza virus variant that survives exposure to an antibody or sera can be measured. For an absolute standard, virions with surface proteins from a non-human influenza virus subtype can be used, such as subtypes H4, H6, or H14. In particular embodiments, any viral surface protein not affected by the antibody or sera can be used as an absolute standard. With these standards, neutralization curves can be generated by incubating the virus libraries at several antibody concentrations, infecting cells with the treated viruses, and sequencing the barcodes. The fraction of each mutant surviving relative to the standards can be computed. In particular embodiments, the use of two standards will allow detection of whether one is unexpectedly affected by the antibody. Neutralization curves can be fit and the data can be represented as in FIG. 5B.

In particular embodiments, the selection pressure is heat. Heat can include temperatures above 25° C., above 26° C., above 27° C., above 28° C., above 29° C., above 30° C., above 31° C., above 32° C., above 33° C., above 34° C., above 35° C., above 36° C., above 37° C., above 38° C., above 39° C., above 40° C., above 41° C., above 42° C., above 43° C., above 44° C., above 45° C., above 46° C., above 48° C., above 49° C., above 49° C., above 50° C., or more. In particular embodiments, heat can include temperatures from 28° C. to 70° C. In particular embodiments, heat can include temperatures from 30° C. to 65° C. In particular embodiments, heat can include temperatures above 30° C. In particular embodiments, the selection pressure is cold. Cold can include temperatures below 25° C., below 24° C., below 23° C., below 22° C., below 21° C., below 20° C., below 19° C., below 18° C., below 17° C., below 16° C., below 15° C., below 14° C., below 13° C., below 12° C., below 11° C., below 10° C., below 9° C., below 8° C., below 7° C., below 6° C., below 5° C., below 4° C., below 3° C., below 2° C., below 1° C., below 0° C., or lower. In particular embodiments, cold can include temperatures from 22° C. to 0° C. In particular embodiments, cold can include temperatures from 20° C. to 4° C. In particular embodiments, cold can include temperatures below 20° C. In particular embodiments, the selection pressure is low pH. Low pH can include pH of 6.9, 6.5, 6.0, 5.5, 5.0, 4.5, 4.0, 3.5, 3.0, 2.5, 2.0, or lower. In particular embodiments, low pH can be from pH of 6.8 to 2.0. In particular embodiments, low pH can be from pH of 6.5 to 3.0. In particular embodiments, low pH can include a pH below 6.5. In particular embodiments, the selection pressure is high pH. High pH can include pH of 7.5, 7.6, 7.7, 7.8, 7.9, 8.0, 8.5, 9.0, 9.5, 10.0, 10.5, 11.0, 11.5, 12.0, or higher. In particular embodiments, high pH can include pH of 8.0 to 14.0. In particular embodiments, high pH can include pH of 8.5 to 12.0. In particular embodiments, high pH can include a pH above 8.0.

(iv) Engineering More Effective Antibodies. The systems and methods of the present disclosure can be used to engineer antibodies that are more effective in neutralizing a viral protein. In particular embodiments, a method of engineering a second, more effective therapeutic antibody from a first antibody against a virus using a barcoded influenza virus deep mutational scanning library can include: obtaining the barcoded influenza virus library wherein the barcoded influenza virus variants collectively provide viral protein variants including at least 15 amino acid substitutions at at least 95% of amino acid positions of the viral protein under analysis; exposing target cells to (i) the virions and (ii) the first antibody; sequencing barcodes following exposure to the first antibody, wherein the barcodes associated with variant nucleotide sequences conferring an ability to evade the first antibody increase in frequency and the barcodes associated with variant nucleotide sequences conferring an inability to evade the first antibody decrease in frequency; comparing variant nucleotide sequences conferring an ability to evade the first antibody with the nucleotide sequence of a reference viral protein that the first antibody binds; modifying amino acid residues in the first antibody based on the comparing and on a known crystal structure of the reference viral protein/first antibody complex, thereby engineering a second, more effective therapeutic antibody from a first antibody against the virus. In particular embodiments, engineering a more effective antibody can include the method described in Diskin et al. (2013) J. Exp. Med. 210(6): 1235-1249.

Naturally occurring antibody structural units include a tetramer. Each tetramer includes two pairs of polypeptide chains, each pair having one light chain and one heavy chain. The amino-terminal portion of each chain includes a variable region that is responsible for antigen recognition and epitope binding. The variable regions exhibit the same general structure of relatively conserved framework regions (FR) joined by three hyper variable regions, also called complementarity determining regions (CDRs). The CDRs from the two chains of each pair are aligned by the framework regions, which enables binding to a specific epitope. From N-terminal to C-terminal, both light and heavy chain variable regions include the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), or Chothia & Lesk, J. Mol. Biol., 196:901-917 (1987); Chothia et al., Nature, 342:878-883 (1989).

The carboxy-terminal portion of each chain defines a constant region that can be responsible for effector function. Examples of effector functions include: C1q binding and complement dependent cytotoxicity (CDC); antibody-dependent cell-mediated cytotoxicity (ADCC); antibody-dependent phagocytosis (ADCP); down regulation of cell surface receptors (e.g. B cell receptors); and B cell activation.

Within full-length light and heavy chains, the variable and constant regions are joined by a "J" region of amino acids, with the heavy chain also including a "D" region of amino acids. See, e.g., Fundamental Immunology, Ch. 7 (Paul, W., ed., 2nd ed. Raven Press, N.Y. (1989).

Unless otherwise indicated, the term "antibody" includes, in addition to antibodies including two full-length heavy chains and two full-length light chains as described above, variants, derivatives, and fragments thereof, examples of which are described below. Furthermore, unless explicitly excluded, antibodies can include monoclonal antibodies, human antibodies, bispecific antibodies, polyclonal antibodies, linear antibodies, minibodies, domain antibodies, synthetic antibodies, chimeric antibodies, antibody fusions, and fragments thereof, respectively. In particular embodiments, antibodies (e.g., full length antibodies) can be produced in human suspension cells.

In particular embodiments, monoclonal antibodies refer to antibodies produced by a clone of B cells or hybridoma cells. In particular embodiments, monoclonal antibodies are identical to each other and/or bind the same epitope, except for possible antibodies containing naturally occurring mutations or mutations arising during production of a monoclonal antibody. In particular embodiments, in contrast to polyclonal antibody preparations, which include different antibodies directed against different epitopes, each monoclonal antibody of a monoclonal antibody preparation is directed against a single epitope on an antigen.

A "human antibody" is one which includes an amino acid sequence which corresponds to that of an antibody produced by a human or a human cell or derived from a non-human source that utilizes human antibody repertoires or other human antibody-encoding sequences.

A "human consensus framework" is a framework which represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. The subgroup of sequences can be a subgroup as in Kabat et al., Sequences of Proteins of Immunological Interest, Fifth Edition, NIH Publication 91-3242, Bethesda Md. (1991), vols. 1-3. In particular embodiments, for the $V_L$, the subgroup is subgroup kappa I as in Kabat et al., supra. In particular embodiments, for the $V_H$, the subgroup is subgroup III as in Kabat et al., supra.

In particular embodiments, an antibody fragment is used. An "antibody fragment" denotes a portion of a complete or full-length antibody that retains the ability to bind to an epitope. Examples of antibody fragments include Fv, single chain Fv fragments (scFvs), Fab, Fab', Fab'-SH, $F(ab')_2$, diabodies, linear antibodies, and/or any biologically effective fragments of an immunoglobulin that bind specifically to an epitope described herein. Antibodies or antibody fragments include all or a portion of polyclonal antibodies, monoclonal antibodies, human antibodies, humanized antibodies, synthetic antibodies, chimeric antibodies, bispecific antibodies, mini bodies, and linear antibodies.

A single chain variable fragment (scFv) is a fusion protein of the variable regions of the heavy and light chains of immunoglobulins connected with a short linker peptide. Fv fragments include the $V_L$ and $V_H$ domains of a single arm of an antibody. Although the two domains of the Fv fragment, $V_L$ and $V_H$, are coded by separate genes, they can be joined, using, for example, recombinant methods, by a synthetic linker that enables them to be made as a single protein chain in which the $V_L$ and $V_H$ regions pair to form monovalent molecules (single chain Fv (scFv)). For additional information regarding Fv and scFv, see e.g., Bird, et al., Science 242 (1988) 423-426; Huston, et al., Proc. Natl. Acad. Sci. USA 85 (1988) 5879-5883; Plueckthun, in The Pharmacology of Monoclonal Antibodies, vol. 113, Rosenburg and Moore (eds.), Springer-Verlag, New York), (1994) 269-315; WO1993/16185; U.S. Pat. Nos. 5,571,894; and 5,587,458.

A Fab fragment is a monovalent antibody fragment including $V_L$, $V_H$, $C_L$ and $C_{H1}$ domains. A $F(ab')_2$ fragment is a bivalent fragment including two Fab fragments linked by a disulfide bridge at the hinge region. For discussion of Fab and $F(ab')_2$ fragments having increased in vivo half-life, see U.S. Pat. No. 5,869,046. Diabodies include two epitope-binding sites that may be bivalent. See, for example, EP 0404097; WO1993/01161; and Holliger, et al., Proc. Natl. Acad. Sci. USA 90 (1993) 6444-6448. Dual affinity retargeting antibodies (DART™; based on the diabody format but featuring a C-terminal disulfide bridge for additional stabilization (Moore et al., Blood 117, 4542-51 (2011)) can also be used. Antibody fragments can also include isolated CDRs. For a review of antibody fragments, see Hudson, et al., Nat. Med. 9 (2003) 129-134.

Antibody fragments can be made by various techniques, including proteolytic digestion of an intact antibody as well as production by recombinant host-cells (e.g., human suspension cell lines, *E. coli* or phage), as described herein. Antibody fragments can be screened for their binding properties in the same manner as intact antibodies.

A neutralizing antibody can refer to an antibody that, upon epitope binding, can reduce biological function of its target antigen. In particular embodiments neutralizing antibodies can reduce (i.e., neutralize) viral infection of cells. In particular embodiments percent neutralization can refer to a percent decrease in viral infectivity in the presence of the antibody, as compared to viral infectivity in the absence of the antibody. For example, if half as many cells in a sample become infected in the presence of an antibody, as compared to in the absence of the antibody, this can be calculated as 50% neutralization. In particular embodiments "neutralize viral infection" can refer to at least 40% neutralization, at least 50% neutralization, at least 60% neutralization, at least 70% neutralization, at least 80% neutralization, or at least 90% neutralization of viral infection. In particular embodiments, the antibodies can block viral infection (i.e., 100% neutralization). In particular embodiments, the anti-viral antibodies can inhibit envelope fusion with target cells, which can result in neutralization of viral infection. Inhibition of viral envelope fusion to target cells can be at least 40% inhibition, at least 50% inhibition, at least 60% inhibition, at least 70% inhibition, at least 80% inhibition, or at least 90% inhibition, as compared to viral envelope fusion in the absence of the anti-viral antibody.

In particular embodiments, an antibody that neutralizes a viral infection is effective against the virus.

(v) Selection of Effective Anti-Viral Conditions and/or Effective Therapeutic Compounds. Assessments described herein can be used to select effective anti-viral conditions and/or effective therapeutic compounds.

An effective therapeutic compound refers to a compound that can reduce, prevent, or treat influenza virus infection when the compound is administered to a subject. In particular embodiments, an effective therapeutic compound can prevent, reduce, or treat the likelihood of a influenza virus infection.

An amount of the therapeutic compound that is effective will vary depending on the compound, the severity or risk of infection, and the age, weight, physical condition and responsiveness of the subject to be treated. The exact dose and formulation will depend on the purpose of the treatment and can be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)).

In certain cases, a "therapeutically effective amount" is used to mean an amount or dose sufficient to modulate, e.g., increase or decrease a desired activity e.g., by 10%, by 50%, or by 90%. Generally, a therapeutically effective amount is sufficient to cause a clinically significant improvement in a subject following a therapeutic regimen involving one or more therapeutic compounds. The concentration or amount of the compound depends on the desired dosage and administration regimen. The effective amounts of compounds containing active agents include doses that partially or completely achieve the desired therapeutic, prophylactic, and/or biological effect.

(vi) Host Adaptation Studies. To enable identification of host adaptation, how mutations affect each viral entry protein's ability to mediate infection of cells from relevant host species can be measured (FIGS. 7, 8A, 8B). In particular embodiments, methods described herein measure the preference for each amino acid at each site in a viral entry protein under selection to infect different cell lines.

Figure 7:
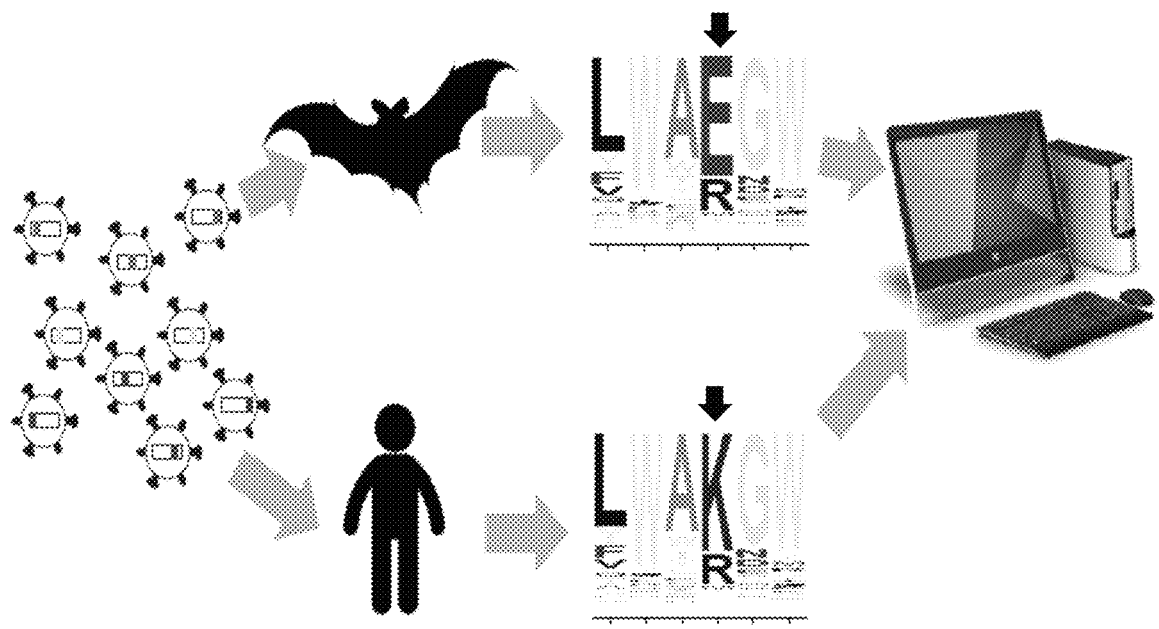
FIG. 7. The functional effects of all mutations can be mapped in cells from relevant host species. For instance, a natural animal reservoir can be bats and the relevant test species can be humans. Species-specific maps of mutational effects can be used to inform sequence-based methods to identify viral host adaptation. For example, in the logo plots (I), at the 4th site, amino acid E is favored in bat cells but amino acid K is favored in human cells. New influenza viral sequences can be scored for their adaptation to each host (II).
Figure 8A:
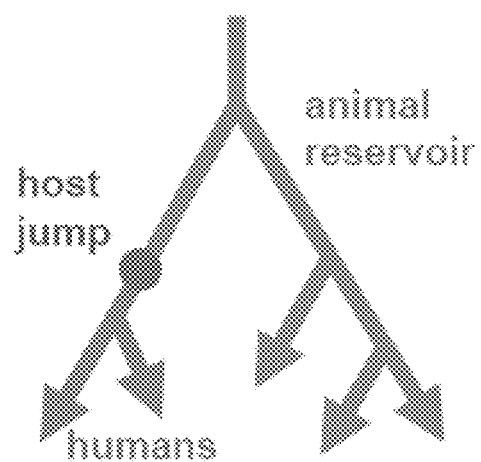
FIGS. 8A, 8B. Scoring host adaptation.
Figure 8B:
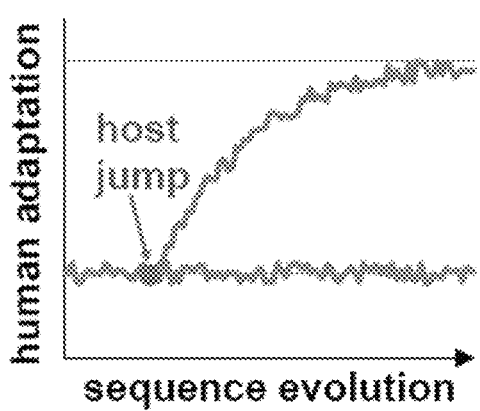

Using an HA library as an example, the libraries can be used to measure the functional effects of all mutations to HA. Viral infectivity will depend on HA. The virions can be used to infect cells (e.g., MDCK-SIAT1 cells). Then, viral RNA can be isolated and the barcodes can be sequenced to quantify the variant frequencies in each case. On an Illumina HiSeq 4000, the cost of sequencing $5 \times 10^5$ barcodes to 10× coverage is currently $25. Since the typical single amino acid mutant will have 15 barcodes, this gives >100 counts for the typical mutation in the unselected condition. Counts in the selected condition will vary depending on the functionality of that particular HA mutant. Algorithms to extract functional information from deep mutational scanning counts have been described and implemented (see FIG. 6 adapted from Bloom BMC Bioinformatics 16: 168 (2015) and on the World Wide Web at jbloomlab.githubio/dms_tools2). These algorithms can be used to estimate the "preference" of each site in HA for each amino acid (see FIG. 1 and FIG. 7). Such preferences are a useful way to represent the data since they can be related to viral evolution in nature using phylogenetic methods (Hilton, et al. PeerJ 5: e3657 (2017)). In particular embodiments, the preferences can be estimated using barcode counts for single amino acid mutants. Preferences for multiple mutations can also be estimated. Other alternative strategies for estimating the effects of mutations from the sequencing data can also be used.

As exemplary uses, the libraries can be used to map how all mutations to entry proteins of influenza virus strains affect capacity to infect cells from relevant species. Certain influenza virus strains circulate in animal reservoirs but occasionally transmit to humans. These viruses could therefore cause epidemics or pandemics if they adapt to better infect and transmit among humans.

Differences that are host-specific rather than cell-line specific can often be more interesting. Accordingly, in particular embodiments, multiple cell lines for all hosts can be used to identify mutations that are robustly favored in numerous or all cell lines of that host.

In particular embodiments, (i) duplicate libraries, (ii) the existence of a few barcodes to hundreds of barcodes for each amino acid mutant, and (iii) algorithms similar to those in Haddox et al. eLife 7:e34420 (2018)) can be used to quantify noise and identify cell-line-specific differences that exceed this noise.

Results across more than one strain of a virus can be used to determine the extent that mutations are generally host adaptive versus strain-specific effects because viral strains can be genetically diverse (see Haddox et al. eLife 7:e34420 (2018)). Using, for example, two or more strains of a virus allows assessment of how well the measurements can be generalized across strains. In particular embodiments, assessing strain-specificity can be important in order to use the methods to better score host adaptation. Another way to examine this question is via the multiple mutants in the libraries. Particularly, whether effects of multiple mutations are the sum of the effects of the individual mutations can be assessed under an optimal scale as determined in Sailer et al. Genetics 205: 1079-1088 (2017).

As indicated, in particular embodiments, measurements can be used to develop algorithms that score a virus's host adaptation from its sequence. This will advance assessment of the risk of viral host jumps (Russell et al. eLife 3: e03883 (2014)), and improve the ability to identify viral adaptation during human outbreaks.

In particular embodiments, host adaptation can be scored as in FIG. 6. In particular embodiments, host scoring can be performed using an additive model. For example, if $$\pi_{r,a}^h$$

is the preference for amino acid a at site r measured in cells from host h (e.g., the logo plots in FIG. 7), then the adaptation to host h of sequence s is scored as $$S_h(s) = \sum_r \log(\pi_{r,s_r}^h)$$

where $s_r$ is the amino acid at site r of sequence s.

Historical data can be used to evaluate the scoring models. While additive models might seem simplistic, similar models informed by deep mutational scanning discriminated the evolutionary success of human influenza virus lineages (Lee, et al. Proceedings of the National Academy of Sciences, 115(35), E8276-E8285 (2018)), which is probably a harder problem since fitness differences between human influenza variants are likely smaller than those between variants of emerging viruses that have and have not adapted to humans.

As measurements for multiple mutations and different strain backgrounds are accumulated, epistatic models that incorporate non-additivity in forms can be explored (see, e.g., Louie et al. Proceedings of the National Academy of Sciences: 201717765 (2018); Hopf et al. Nature Biotechnology 35: 128 (2017); Poelwijk et al. Learning the pattern of epistasis linking genotype and phenotype in a protein. bioRxiv: 213835 (2017); Sailer & Harms PLoS Computational Biology 13: e1005541 (2017)).

In particular embodiments, the systems and methods disclosed herein can be used to assess whether antigenic selection drives viral evolution. For example, it is unclear if immune selection drives the evolution of emerging virus strains. Uses of the libraries disclosed herein can identify sites where mutations affect immune recognition. Whether these immune-targeted sites evolve faster than other sites can be assessed. For example, one can fit codon-substitution models where the relative rate of amino acid substitution (dN/dS) is uniform across the gene or takes on a different value at sites experiments map as being under immune selection. HyPhy [Pond & Muse (2005) HyPhy: hypothesis testing using phylogenies. In: Statistical Methods in Molecular Evolution, Springer. pp. 125-181] can be used to fit these models, and a likelihood-ratio test to evaluate the support for the partitioned model versus the nested non-partitioned alternative can be used. Issues associated with strain specificity can also apply in these uses. That is, it may be that the antigenic effects of mutations vary among the strains of a virus. However, this issue can be assessed. These uses are based on the idea that epitopes are similar among different sera, but different sera could target very different epitopes due to host-to-host variation. In that case the generality of the mapping is reduced, but the throughput of disclosed methods then provides a way to characterize this variation, which is interesting in its own right.

(vii) Kits. Combinations of elements of the deep mutational scanning libraries disclosed herein can be provided as kits. Kits of the present disclosure can include: expression plasmids expressing barcoded influenza virus; one or more cell lines; transfection reagents; and a reference viral protein. In particular embodiments, the plasmids can be ambisense to allow both transcription of negative sense vRNA and expression of the viral protein encoded by the coding region of the vRNA. In particular embodiments, the reference viral protein is not recognized by sera that recognizes a viral protein in the barcoded influenza virus. In particular embodiments kits can include a deep mutational scanning library of barcoded influenza virus as disclosed herein. In particular embodiments, kits can include reagents for creating a deep mutation scanning library of barcoded influenza virus in expression plasmids such as reverse transcriptase, polymerase, amplification reagents (dNTPs, buffers, salts), packaging signal sequences, primers without barcodes, primers with barcodes, ligase, and restriction enzymes for generating expression plasmids including barcoded influenza genome segments with one or more inserted copy of a packaging signal.

Kits can include further instructions for using the kit, for example, instructions for transfection of cell lines expression plasmids expressing barcoded with transcription of negative sense vRNA and/or for expression of viral proteins from plasmids. The instructions can be in the form of printed instructions provided within the kit or the instructions can be printed on a portion of the kit itself. Instructions may be in the form of a sheet, pamphlet, brochure, CD-Rom, or computer-readable device, or can provide directions to instructions at a remote location, such as a website. In particular embodiments, kits can also include laboratory supplies needed to use the kit effectively, such as culture media, buffers, enzymes, sterile plates, sterile flasks, pipettes, gloves, and the like. Variations in contents of any of the kits described herein can be made.

(viii) Exemplary Embodiments

The Exemplary Embodiments and Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

1. A method for barcoding an influenza virus genome segment with minimal to no effects on viral fitness including:
   inserting a nucleic acid barcode and a copy of a 5' viral RNA genome packaging signal between the end of the corresponding genome segment open reading frame and the naturally occurring non-coding portion of the 5' viral RNA genome packaging signal.
2. A method of embodiment 1, further including inserting a copy of the 3' viral genome packaging signal between the non-coding portion of the naturally occurring 3' viral RNA genome packaging signal and the beginning of the genome segment open reading frame.
3. A method of embodiment 1 or 2, wherein the copy of the 3' viral RNA genome packaging signal lacks a start codon.
4. A method of embodiment 2, wherein the copy of the 5' viral RNA genome packaging signal and the copy of the 3' viral RNA genome packaging signal lack a start codon.
5. A method of embodiment 1 or 2, wherein the copy of the 5' viral RNA genome packaging signal has at least 80% sequence identity with the naturally occurring 5' viral RNA genome packaging signal and/or wherein the copy of the 3' viral RNA genome packaging signal has at least 80% sequence identity with the naturally occurring 3' viral RNA genome packaging signal.
6. A method of embodiment 2, wherein the copy of the 5' viral RNA genome packaging signal has at least 80% sequence identity with the naturally occurring 5' viral RNA genome packaging signal and the copy of the 3' viral RNA genome packaging signal has at least 80% sequence identity with the naturally occurring 3' viral RNA genome packaging signal.
7. A method of embodiment 1 or 2, wherein the copy of the 5' viral RNA genome packaging signal has at least 90% sequence identity with the naturally occurring 5' viral RNA genome packaging signal and/or wherein the copy of the 3' viral RNA genome packaging signal has at least 90% sequence identity with the naturally occurring 3' viral RNA genome packaging signal.
8. A method of embodiment 2, wherein the copy of the 5' viral RNA genome packaging signal has at least 90% sequence identity with the naturally occurring 5' viral RNA genome packaging signal and the copy of the 3' viral RNA genome packaging signal has at least 90% sequence identity with the naturally occurring 3' viral RNA genome packaging signal.
9. A method of embodiment 1 or 2, wherein the copy of the 5' viral RNA genome packaging signal has at least 95% sequence identity with the naturally occurring 5' viral RNA genome packaging signal and/or wherein the copy of the 3' viral RNA genome packaging signal has at least 95% sequence identity with the naturally occurring 3' viral RNA genome packaging signal.
10. A method of embodiment 2, wherein the copy of the 5' viral RNA genome packaging signal has at least 95% sequence identity with the naturally occurring 5' viral RNA genome packaging signal and the copy of the 3' viral RNA genome packaging signal has at least 95% sequence identity with the naturally occurring 3' viral RNA genome packaging signal.
11. A method of embodiment 1 or 2, wherein the copy of the 5' viral RNA genome packaging signal has at least 99% sequence identity with the naturally occurring 5' viral RNA genome packaging signal and/or wherein the copy of the 3' viral RNA genome packaging signal has at least 99% sequence identity with the naturally occurring 3' viral RNA genome packaging signal.
12. A method of embodiment 2, wherein the copy of the 5' viral RNA genome packaging signal has at least 99% sequence identity with the naturally occurring 5' viral RNA genome packaging signal and the copy of the 3' viral RNA genome packaging signal has at least 99% sequence identity with the naturally occurring 3' viral RNA genome packaging signal.
13. A method of embodiment 1 or 2, wherein the copy of the 5' viral RNA genome packaging signal has 100% sequence identity with the naturally occurring 5' viral RNA genome packaging signal and/or wherein the copy of the 3' viral RNA genome packaging signal has 100% sequence identity with the naturally occurring 3' viral RNA genome packaging signal.
14. A method of embodiment 2, wherein the copy of the 5' viral RNA genome packaging signal has 100% sequence identity with the naturally occurring 5' viral RNA genome packaging signal and the copy of the 3' viral RNA genome packaging signal has 100% sequence identity with the naturally occurring 3' viral RNA genome packaging signal.
15. A method of any of embodiments 1-14, wherein the nucleic acid barcode includes 4-100 nucleotides in length.

16. A method of any of embodiments 1-14, wherein the nucleic acid barcode includes 10-30 nucleotides in length.
17. A method of any of embodiments 1-14, wherein the nucleic acid barcode is 18 nucleotides in length.
18. A method of any of embodiments 1-17, wherein the open reading frame encodes hemagglutinin (HA), neuraminidase (NA), M1 matrix protein (M1), M2 ion channel protein (M2), nuclear protein (NP), nonstructural protein 1 (NS1), nonstructural protein 1 (NS2), or a subunit of an RNA-dependent RNA polymerase complex selected from PB1, PB2, and PA.
19. A barcoded influenza virus including one or more barcoded influenza virus genome segments formed according to a method of any of embodiments 1-18.
20. The barcoded influenza virus of embodiment 19, wherein the influenza virus is an influenza A virus, an influenza B virus, an influenza C virus, or an influenza D virus.
21. A deep mutational scanning library including barcoded influenza virus genome segments formed according to a method of any of embodiments 1-18.
22. The deep mutational scanning library of embodiment 21, wherein the set of barcoded variant nucleotide sequences collectively encode viral protein variants including at least 17 amino acid substitutions at at least 95% of amino acid positions of the viral protein.
23. The deep mutational scanning library of embodiment 21, wherein the set of barcoded variant nucleotide sequences collectively encode (i) viral protein variants including at least 19 amino acid substitutions at all amino acid positions of the viral protein or (ii) a random or selected number of substitutions at a pre-determined subset of sites within a protein of interest.
24. A method of identifying mutations in a viral protein that affect the sensitivity of the virus to a selection pressure using a barcoded deep mutational scanning library wherein the method includes:
Obtaining the library of any of embodiments 21-23;
Culturing the virions;
Exposing the virions to the selection pressure;
Sequencing barcodes of variant nucleotide sequences from surviving virions; and
Linking sequenced barcodes to encoded viral protein variants to identify mutations in each surviving variant relative to a reference under the selection pressure, thereby identifying mutations in a viral protein that affect the sensitivity of a virus to the selection pressure.
25. The method of embodiment 24, wherein the reference includes a counterpart viral protein of a wild-type virus, of a parental virus, or of a baseline clinical isolate.
26. The method of embodiment 24 or 25, wherein the reference includes an absolute standard obtained from a glycoprotein of an influenza strain that is not recognized by the sera or antibodies of the species under consideration.
27. The method of any of embodiments 24-26, wherein the reference includes an absolute standard obtained from a glycoprotein of an influenza strain that is not recognized by the sera or antibodies of humans.
28. The method of any of embodiments 24-27, wherein the selection pressure includes a therapeutic compound.
29. The method of embodiment 28, further including calculating a percentage of viral protein variants that the therapeutic compound is effective against, thereby identifying the percentage of viral entry protein variants of a virus that the therapeutic compound is effective against.
30. The method of embodiment 28 or 29, further including selecting a therapeutic compound with the highest efficacy against the virus by repeating the exposing, sequencing, linking, and calculating steps for a multitude of therapeutic compounds, and selecting the therapeutic compound effective with the highest efficacy against the virus.
31. The method of any of embodiments 28-30, wherein the therapeutic compound is undergoing pre-clinical development.
32. The method of any of embodiments 28-30, wherein the therapeutic compound is undergoing clinical development.
33. The method of any of embodiments 28-32, wherein the therapeutic compound includes viral entry and/or fusion inhibitors.
34. The method of any of embodiments 28-32, wherein the therapeutic compound includes an antibody, or sera from humans or animals following infection or vaccination.
35. The method of embodiment 34, wherein the antibody is TNX-355 (ibalizumab), PGT121, or 3BNC117.
36. The method of any of embodiments 28-32, wherein the therapeutic compound includes a small molecule, a protein, a peptide, a polynucleotide, a polysaccharide, an oil, a solution, or a plant extract.
37. The method of any of embodiments 24-27, wherein the selection pressure is selected from heat, cold, low pH, high pH, and a toxic agent.
38. The method of embodiment 34, further including: calculating the fraction of each surviving virion associated with a particular variant relative to the reference at each antibody concentration; and generating an antibody neutralization curve for each variant nucleotide sequence associated with a surviving virion.
39. The method of embodiment 38, wherein the antibody neutralization curve is visualized as sequence logo plots.
40. The method of embodiment 38 or 39, wherein barcode counts for a given variant nucleotide sequence greater than barcode counts for the reference at each antibody concentration indicate that a virus including the viral protein encoded by the variant nucleotide sequence is resistant to the neutralization antibody.
41. The method of any of embodiments 29-36, further including scoring a phenotype as a function of the concentration of the therapeutic compound to obtain an $EC_{50}$ value for each surviving virion associated with a variant viral protein.
42. The method of embodiment 41, further including calculating a ratio of the $EC_{50}$ value for each surviving virion to an $EC_{50}$ value of the reference, wherein the ratio indicates a fold resistance change for each surviving virion associated with a variant viral protein.
43. The method of embodiment 41 or 42, further including calculating the fold resistance change for each variant protein to other therapeutic compounds in the same class.
44. The method of any of embodiments 41-43, wherein the phenotype includes virus titer or target cell survival.
45. The method of embodiment 44, wherein the virus titer is calculated from an assay selected from plaque assay and focus-forming assay.

46. The method of embodiment 44, wherein target cell survival is calculated from a colorimetric MTT cytotoxicity assay.
47. The method of embodiment 24, wherein the selection pressure includes the ability of the virus to enter (i) a host cell of a target host species or (ii) a cell expressing a receptor protein of a species that is different from the species from which the cell was derived, wherein the ability is not dependent on presence of a functional unrelated viral entry protein.
48. The method of embodiment 47, wherein adaptation to a host h of a variant amino acid sequence s is scored as $$S_h(s) = \sum_r \log(\pi_{r,s_r}^h)$$

where $s_r$ is the amino acid at site r of sequence s.
49. The method of embodiment 47 or 48, wherein the target host is selected from human, bat, camel, rat, and bird.
50. The method of embodiment 47 or 48, wherein the cells of a target host species are from human cell lines.
51. The method of embodiment 50, wherein the human cell lines are derived from human liver, human lung, or human lung epithelia.
52. The method of embodiment 51, wherein the human cell line derived from human liver includes HuH7, the human cell line derived from human lung includes Calu-3 or MRC-5, and/or the human cell line derived from human lung epithelia is A549 or BEAS-2B.
53. The method of embodiment 47 or 48, wherein the cells of a target host species are from bat cell lines.
54. The method of embodiment 53, wherein the bat cell lines are derived from fruit bat lung, fruit bat kidney, Egyptian fruit bat, or pipestrelle bat.
55. The method of embodiment 47 or 48, wherein the target host species is human.

In particular embodiments of each of the Exemplary Embodiments, and unless otherwise specified by a particular embodiment, the libraries can include distinct protein variants that are not deep mutational scanning variants, but instead reflect a collection of different variants of a protein. As just one example, a library could include 200 different HA genes. Such an alternative library can yield valuable information using "neutralization fingerprinting" (i.e. looking at sequence motifs of variants that survive or evade a selection pressure vs those that do not).

In particular embodiments of each of the Exemplary Embodiments that reference a selective process (e.g. a selection pressure), and unless otherwise specified by a particular embodiment, virions can be selected for by the selection pressure (e.g., an antibody or inhibitor) and then the selected virions can be used to infect cells. In these embodiments, the barcode of virions that survive/escape or evade the selection pressure and infect cells can be sequenced. In particular embodiments, the ability of selected for virions to infect cells is considered a critical component to the identification of escape variants.

In particular embodiments of each of the Exemplary Embodiments, and unless otherwise specified by a particular embodiment, libraries disclosed herein can be used to select for therapeutic compound (e.g., antibody) binding. Selecting for binding can be conducted utilizing barcoded virions. In this scenario, one could then sequence the barcode of viruses that do or do not bind the therapeutic compound.

Particular embodiments include use of more than one selection pressure in combination (e.g., theraepeutic compound and heat; or heat and ph).

(ix) Experimental Examples. Example 1. Exemplary Methods to Create Codon-Mutant Libraries. The following description of methods to create codon-mutant libraries is adapted from Bloom JD (2014) Mol Biol Evol 31:1956-1978 and directed to the influenza virus nucleoprotein (NP). These methods are provided for illustrative purposes so that one of ordinary skill may adapt these teachings to create codon-mutant libraries for viral entry proteins. The methods described in Bloom involved iterative rounds of low-cycle PCR with pools of mutagenic synthetic oligonucleotides that each contained a randomized NNN triplet at a specific codon site. Two replicate libraries each of the WT and, in this example, N334H variants of the Aichi/1968 NP were prepared in full biological duplicate, beginning each with independent preps of the plasmid templates pHWAichi68-NP and pHWAichi68-NP-N334H. The sequences of the NP genes in these plasmids are provided in Gong et al. (2013) eLife, 2: e00631. To avoid cross-contamination, all purification steps used an independent gel for each sample, with the relevant equipment thoroughly washed to remove residual DNA.

First, for each codon except for that encoding the initiating methionine in the 498-residue NP gene, an oligonucleotide that contained a randomized NNN nucleotide triplet preceded by the 16 nucleotides upstream of that codon in the NP gene and followed by the 16 nucleotides downstream of that codon in the NP gene were designed. Oligonucleotides can be ordered in a 96-well plate format from, for example, Integrated DNA Technologies. They can be combined in equimolar quantities to create the forward-mutagenesis primer pool. The reverse complement of each of these oligonucleotides can also be designed and ordered and combined in equimolar quantities to create the reverse-mutagenesis pool. The primers for the N334H variants differed only for those that overlapped the N334H codon. End primers that anneal to the termini of the NP sequence and contain sites appropriate for BsmBl cloning into the influenza reverse-genetics plasmid pHW2000 (Hoffmann, et al. (2000) Proc Natl Acad Sci USA, 97: 6108-6113) can also be designed. These primers were 5'-BsmBl-Aichi68-NP (catgatcgtctcagggagcaaaagcagggtagataatcactcacag (SEQ ID NO: 39)) and 3'-BsmBl-Aichi68-NP (catgatcgtctcgtatt-agtagaaacaagggtatttttcttta (SEQ ID NO: 40)).

PCR reactions were conducted that contained 1 μl of 10 ng/μl template pHWAichi68-NP plasmid (Gong, et al. (2013) eLife, 2: e00631), 25 μl of 2×KOD Hot Start Master Mix (product number 71842, EMD Millipore), 1.5 μl each of 10 μM solutions of the end primers 5'-BsmBl-Aichi68-NP and 3'-BsmBl-Aichi68-NP, and 21 μl of water. The following PCR program was used (referred to as the amplicon PCR program in the remainder of this article): The PCR products were purified over agarose gels using ZymoClean columns (product number D4002, Zymo Research) and used as templates for the initial codon mutagenesis fragment PCR.
(1) 95° C. for 2 min; (2) 95° C. for 20 s; (3) 70° C. for 1 s; (4) 50° C. for 30 s cooling to 50° C. at 0.5° C./s;
(5) 70° C. for 40 s; (6) Repeat steps 2 through 5 for 24 additional cycles; (7) Hold 4° C.

Two fragment PCR reactions were run for each template. The forward-fragment reactions contained 15 μl of 2×KOD Hot Start Master Mix, 2 μl of the forward mutagenesis primer pool at a total oligonucleotide concentration of 4.5

μM, 2 μl of 4.5 μM 3'-BsmBl-Aichi68-NP, 4 μl of 3 ng/μl of the aforementioned gel-purified linear PCR product template, and 7 μl of water. The reverse-fragment reactions were identical except that the reverse mutagenesis pool was substituted for the forward mutagenesis pool and that 5'-BsmBl-Aichi68-NP was substituted for 3'-BsmBl-Aichi68-NP. The PCR program for these fragment reactions was identical to the amplicon PCR program except that it utilized a total of 7 rather than 25 thermal cycles.

The products from the fragment PCR reactions were diluted 1:4 in water. These dilutions were then used for the joining PCR reactions, which contained 15 μl of 2×KOD Hot Start Master Mix, 4 μl of the 1:4 dilution of the forward-fragment reaction, 4 μl of the 1:4 dilution of the reverse-fragment reaction, 2 μl of 4.5 μM 5'-BsmBl-Aichi68-NP, 2 μl of 4.5 μM 3'-BsmBl-Aichi68-NP, and 3 μl of water. The PCR program for these joining reactions was identical to the amplicon PCR program except that it utilized a total of 20 rather than 25 thermal cycles. The products from these joining PCRs were purified over agarose gels.

The purified products of the first joining PCR reactions were used as templates for a second round of fragment reactions followed by joining PCRs. These second-round products were used as templates for a third round. The third-round products were purified over agarose gels, digested with BsmBl (product number R0580L, New England Biolabs), and ligated into a dephosphorylated (Antarctic Phosphatase, product number M0289L, New England Biolabs) BsmBl digest of pHW2000 (Hoffmann et al. 2000) using T4 DNA ligase. The ligations were purified using ZymoClean columns, electroporated into ElectroMAX DH10B T1 phage-resistant competent cells (product number 12033-015, Invitrogen), and plated on LB plates supplemented with 100 μg/ml of ampicillin. These transformations yielded between 400,000 and 800,000 unique transformants per plate, as judged by plating a 1:4,000 dilution of the transformations on a second set of plates. Transformation of a parallel no-insert control ligation yielded 50-fold fewer colonies, indicating that self-ligation of pHW2000 only accounts for a small fraction of the transformants. For each library, three transformations were performed, the plates were grown overnight, and then the colonies were scraped into liquid LB supplemented with ampicillin and mini-prepped several hours later to yield the plasmid mutant libraries. These libraries each contained in excess of $10^6$ unique transformants, most of which will be unique codon mutants of the NP gene.

The NP gene was sequenced for 30 individual clones drawn from the four mutant libraries. The number of mutations per clone was Poisson distributed and the mutations occurred uniformly along the primary sequence. If all codon mutations are made with equal probability, 9/63 of the mutations should be single-nucleotide changes, 27/63 should be two-nucleotide changes, and 27/63 should be three-nucleotide changes. This is what was observed in the Sanger-sequenced clones. The nucleotide composition of the mutated codons was roughly uniform, and there was no tendency for clustering of multiple mutations in primary sequence. The results of this Sanger sequencing are compatible with the mutation frequencies obtained from deep sequencing the "mutDNA" samples after subtracting off the sequencing error rate estimated from the DNA samples, especially considering that the statistics from the Sanger sequencing are subject to sampling error due to the limited number of clones analyzed.

Example 2. Antibody selection of a barcoded deep mutational scanning library of influenza HA viral entry proteins. Antibody selection can assess the ability of different HA viral entry proteins to evade antibody neutralization. Virions produced from the library and barcoded nucleotide sequences encoding variants of HA can be incubated with an antibody that targets the influenza virus. Target cells can then be exposed to the virions. Virions not treated with antibody can serve as a replicate-specific control to calculate differential selection. For each condition, $10^6$ infectious units of the library can be incubated ±1 μg/mL of antibody at 37° C. for 1 hr, then infected into $10^6$ (not antibody treated) or $2\times10^5$ (antibody treated) target cells in the presence of 100 μg/mL DEAE-dextran. The antibody concentration can be chosen with the goal of inhibiting 97.5% of the viral infectivity. Three hours post exposure, cells can be spun down and resuspended in fresh media, containing no DEAE-dextran. At 12 hr post exposure, cells can be spun down, washed with phosphate-buffered saline (PBS), and then subjected to a mini-prep to harvest non-integrated viral cDNA.

Example 3. Deep sequencing and data analysis. Deep sequencing can be used to determine the frequency of each mutation in the antibody-selected and non-selected conditions. A high throughput sequencing method that can sequence long reads with high accuracy, such as circular consensus Pac-Bio sequencing (Travers, et al. (2010) Nucleic Acids Research 38: e159-e159; and Laird Smith, et al. (2016) Virus Evolution 2: vew018), can be used to associate each influenza virus variant with its barcode. Amplification of barcode-linked genes can be via emulsion PCR to allow clonal amplification of templates from complex mixtures in a bias-free manner. Schütze et al. (2011) Analytical Biochemistry 410: 155-157. Briefly, the PCR mixture can be combined with an oil surfactant and an emulsion is formed by vigorous vortexing. After PCR, the emulsion can be broken with isobutanol, and binding buffer from a DNA cleanup kit can be added. Centrifugation can be performed to separate organic and aqueous phases, the organic phase can be removed, and DNA in the aqueous phase can be purified using a DNA cleanup kit.

Single Molecule Real Time (SMRT) bell template libraries of barcoded influenza virus genes can be prepared according to the manufacturer's instructions using the SMRTbell Template Prep Kit 1.0 (part no. 100-259-100; Pacific Biosciences, Menlo Park, CA). A total of 250 ng of AMPure PB bead-purified amplicon can be added directly into the DNA damage repair step of the 10-kb Template Preparation and Sequencing (with low-input DNA) protocol. Library quality and quantity can be assessed using the Agilent 12000 DNA Kit and the 2100 Bioanalyzer System (Santa Clara, CA, USA), as well as the Qubit dsDNA BR Assay kit and Qubit Fluorometer (Thermo Fisher, Waltham, MA). Sequencing primer annealing can be performed using the recommended 20:1 primer:template ratio, whereas P5 polymerase binding can be performed at a modified polymerase:template ratio of 3:1. Barcoded influenza virus gene SMRTbell libraries can be immobilized onto SMRT cells at a starting concentration of 10 pM on chip. Loading titrations can be performed to achieve optimal sequencing conditions for particular samples as necessary. SMRT sequencing can be performed on the PacBio RS II using the C3 sequencing kit with magnetic bead loading and 180-minute movies. Circular consensus sequencing (CCS) reads can be generated using Quiver (Chin et al. (2013) Nature Methods. 10: 563-569) and the Reads of Insert (Larsen et al. (2014) BMC Genomics. 15: 720) protocol as a part of SMRT analysis version 2.3, and .fastq files can be used for downstream analysis.

Once each influenza virus variant is associated with its barcode, only barcodes need to be sequenced to determine the frequency of each mutation. Sequencing of barcodes can be performed by an Illumina deep sequencing approach as previously described (Doud & Bloom, Viruses 8: 155 (2016); Haddox et al., PLoS Pathog 12(12): e1006114 (2016)). KOD Hot Start Master Mix (71842, EMD Millipore, Burlington, MA) can be used for each PCR reaction. PCR products can be cleaned with Agencourt AMPure XP beads (A63880, Beckman Coulter, Brea, CA) using a bead-to-sample ratio of 1.0 and quantified via Quant-iT PicoGreen dsDNA Assay Kit (P7589, Life Technologies). 20 µL PCR reaction can be performed to add the remainder of the Illumina sequencing adapters. The PCR reaction conditions can include: (1) 95° C., 2 min; (2) 95° C., 20 s; (3) 70° C., 1 s; (4) 60° C., 10 s; (5) 70° C., 10 s; (6) Go to 2, repeat 23 times; and (7) Hold at 4° C. Finally, samples can be pooled, purified by gel electrophoresis, and sequenced on an Illumina HiSeq or MiSeq using 2×250 bp paired-end reads.

dms_tools on the World Wide Web at jbloomlab.github.io/dms_tools/, version 1.1.dev13, can be used to filter and align the deep-sequencing reads, count the number of times each codon mutation was observed both before and after selection, and infer the influenza virus variant's site-specific amino-acid preferences using, for example, the algorithm described in Bloom et al. BMC bioinformatics. 2015; 16:168.

(x) Closing Paragraphs. Variants of the sequences disclosed and referenced herein are also included. Guidance in determining which amino acid residues can be substituted, inserted, or deleted without abolishing biological activity can be found using computer programs well known in the art, such as DNASTAR™ (Madison, Wisconsin) software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains.

In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. Co., p. 224). Naturally occurring amino acids are generally divided into conservative substitution families as follows: Group 1: Alanine (Ala), Glycine (Gly), Serine (Ser), and Threonine (Thr); Group 2: (acidic): Aspartic acid (Asp), and Glutamic acid (Glu); Group 3: (acidic; also classified as polar, negatively charged residues and their amides): Asparagine (Asn), Glutamine (Gln), Asp, and Glu; Group 4: Gln and Asn; Group 5: (basic; also classified as polar, positively charged residues): Arginine (Arg), Lysine (Lys), and Histidine (His); Group 6 (large aliphatic, nonpolar residues): Isoleucine (Ile), Leucine (Leu), Methionine (Met), Valine (Val) and Cysteine (Cys); Group 7 (uncharged polar): Tyrosine (Tyr), Gly, Asn, Gln, Cys, Ser, and Thr; Group 8 (large aromatic residues): Phenylalanine (Phe), Tryptophan (Trp), and Tyr; Group 9 (non-polar): Proline (Pro), Ala, Val, Leu, Ile, Phe, Met, and Trp; Group 11 (aliphatic): Gly, Ala, Val, Leu, and Ile; Group 10 (small aliphatic, nonpolar or slightly polar residues): Ala, Ser, Thr, Pro, and Gly; and Group 12 (sulfur-containing): Met and Cys. Additional information can be found in Creighton (1984) Proteins, W. H. Freeman and Company.

In making such changes, the hydropathic index of amino acids may be considered. The importance of the hydropathic amino acid index in conferring interactive biologic function on a protein is generally understood in the art (Kyte and Doolittle, 1982, J. Mol. Biol. 157(1), 105-32). Each amino acid has been assigned a hydropathic index on the basis of its hydrophobicity and charge characteristics (Kyte and Doolittle, 1982). These values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glutamate (−3.5); Gln (−3.5); aspartate (−3.5); Asn (−3.5); Lys (−3.9); and Arg (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: Arg (+3.0); Lys (+3.0); aspartate (+3.0±1); glutamate (+3.0±1); Ser (+0.3); Asn (+0.2); Gln (+0.2); Gly (0); Thr (−0.4); Pro (−0.5±1); Ala (−0.5); His (−0.5); Cys (−1.0); Met (−1.3); Val (−1.5); Leu (−1.8); Ile (−1.8); Tyr (−2.3); Phe (−2.5); Trp (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like. As indicated elsewhere, variants of gene sequences can include codon optimized variants, sequence polymorphisms, splice variants, and/or mutations that do not affect the function of an encoded product to a statistically-significant degree.

Variants of the protein, nucleic acid, and gene sequences disclosed herein also include sequences with at least 70% sequence identity, 80% sequence identity, 85% sequence, 90% sequence identity, 95% sequence identity, 96% sequence identity, 97% sequence identity, 98% sequence identity, or 99% sequence identity to the protein, nucleic acid, or gene sequences disclosed herein.

"% sequence identity" refers to a relationship between two or more sequences, as determined by comparing the sequences. In the art, "identity" also means the degree of sequence relatedness between protein, nucleic acid, or gene sequences as determined by the match between strings of such sequences. "Identity" (often referred to as "similarity") can be readily calculated by known methods, including those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wisconsin). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wisconsin); BLASTP, BLASTN, BLASTX (Altschul, et al., J. Mol. Biol. 215:403-410 (1990); DNASTAR (DNASTAR, Inc., Madison, Wisconsin); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. As used herein "default values" will mean any set of values or parameters, which originally load with the software when first initialized.

Variants also include nucleic acid molecules that hybridizes under stringent hybridization conditions to a sequence disclosed herein and provide the same function as the reference sequence. Exemplary stringent hybridization conditions include an overnight incubation at 42° C. in a solution including 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at 50° C. Changes in the stringency of hybridization and signal detection are primarily accomplished through the manipulation of formamide concentration (lower percentages of formamide result in lowered stringency); salt conditions, or temperature. For example, moderately high stringency conditions include an overnight incubation at 37° C. in a solution including 6×SSPE (20×SSPE=3M NaCl; 0.2M NaH2PO4; 0.02M EDTA, pH 7.4), 0.5% SDS, 30% formamide, 100 µg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC). Variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

"Specifically binds" refers to an association of a binding domain (of, for example, a CAR binding domain or a nanoparticle selected cell targeting ligand) to its cognate binding molecule with an affinity or Ka (i.e., an equilibrium association constant of a particular binding interaction with units of 1/M) equal to or greater than $10^5$ $M^{-1}$, while not significantly associating with any other molecules or components in a relevant environment sample. "Specifically binds" is also referred to as "binds" herein. Binding domains may be classified as "high affinity" or "low affinity". In particular embodiments, "high affinity" binding domains refer to those binding domains with a Ka of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, or at least $10^{13}$ $M^{-1}$. In particular embodiments, "low affinity" binding domains refer to those binding domains with a Ka of up to $10^7$ $M^{-1}$, up to $10^6$ $M^{-1}$, up to $10^5$ $M^{-1}$. Alternatively, affinity may be defined as an equilibrium dissociation constant (Kd) of a particular binding interaction with units of M (e.g., $10^{-5}$ M to $10^{-13}$ M). In certain embodiments, a binding domain may have "enhanced affinity," which refers to a selected or engineered binding domains with stronger binding to a cognate binding molecule than a wild type (or parent) binding domain. For example, enhanced affinity may be due to a Ka (equilibrium association constant) for the cognate binding molecule that is higher than the reference binding domain or due to a Kd (dissociation constant) for the cognate binding molecule that is less than that of the reference binding domain, or due to an off-rate (Koff) for the cognate binding molecule that is less than that of the reference binding domain. A variety of assays are known for detecting binding domains that specifically bind a particular cognate binding molecule as well as determining binding affinities, such as Western blot, ELISA, and BIACORE® analysis (see also, e.g., Scatchard, et al., 1949, Ann. N.Y. Acad. Sci. 51:660; and U.S. Pat. Nos. 5,283,173, 5,468,614, or the equivalent).

Unless otherwise indicated, the practice of the present disclosure can employ conventional techniques of immunology, molecular biology, microbiology, cell biology and recombinant DNA. These methods are described in the following publications. See, e.g., Sambrook, et al. Molecular Cloning: A Laboratory Manual, 2nd Edition (1989); F. M. Ausubel, et al. eds., Current Protocols in Molecular Biology, (1987); the series Methods IN Enzymology (Academic Press, Inc.); M. MacPherson, et al., PCR: A Practical Approach, IRL Press at Oxford University Press (1991); MacPherson et al., eds. PCR 2: Practical Approach, (1995); Harlow and Lane, eds. Antibodies, A Laboratory Manual, (1988); and R. I. Freshney, ed. Animal Cell Culture (1987).

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would affect viral fitness upon insertion of a nucleic acid barcode in an influenza virus genome segment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Eds. Attwood T et al., Oxford University Press, Oxford, 2006).

What is claimed is:

1. A method for barcoding an influenza virus genome segment that comprises:
   a 3' viral RNA genome packaging signal;
   an open reading frame; and
   a 5' viral RNA genome packaging signal, comprising:
   inserting a nucleic acid comprising a barcode and a copy of the 5' viral RNA genome packaging signal between the end of the open reading frame and the non-coding portion of the 5' viral RNA genome packaging signal,
   wherein the method has minimal to no effects on viral fitness,
   wherein the barcode comprises 5-100 nucleotides in length, and
   wherein the open reading frame encodes hemagglutinin (HA), neuraminidase (NA), M1 matrix protein (M1), M2 ion channel protein (M2), nuclear protein (NP), nonstructural protein 1 (NS1), nonstructural protein 1 (NS2), or a subunit of an RNA-dependent RNA polymerase complex selected from PB1, PB2, and PA.

2. The method of claim 1, further comprising inserting a nucleic acid comprising a copy of the 3' viral RNA genome packaging signal between the non-coding portion of the 3' viral RNA genome packaging signal and the beginning of the open reading frame.

3. The method of claim 1, wherein the copy of the 5' viral RNA genome packaging signal lacks a start codon.

4. The method of claim 1, wherein the copy of the 5' viral RNA genome packaging signal has at least 95% sequence identity with the 5' viral RNA genome packaging signal.

5. The method of claim 2, wherein the copy of the 3' viral RNA genome packaging signal lacks a start codon.

6. The method of claim 2, wherein the copy of the 3' viral RNA genome packaging signal has at least 95% sequence identity with the 3' viral RNA genome packaging signal.

7. The method of claim 1, wherein the barcode is 18 nucleotides in length.

* * * * *